(12) United States Patent
Ginn

(10) Patent No.: US 11,751,994 B2
(45) Date of Patent: *Sep. 12, 2023

(54) SYSTEM FOR DEPLOYING A DEVICE TO A DISTAL LOCATION ACROSS A DISEASED VESSEL

(71) Applicant: Medtronic, Inc., Minneapolis, MN (US)

(72) Inventor: Richard S. Ginn, Gilroy, CA (US)

(73) Assignee: Medtronic, Inc., Minneapolis, MN (US)

( * ) Notice: Subject to any disclaimer, the term of this patent is extended or adjusted under 35 U.S.C. 154(b) by 277 days.

This patent is subject to a terminal disclaimer.

(21) Appl. No.: 17/100,724

(22) Filed: Nov. 20, 2020

(65) Prior Publication Data
US 2021/0068953 A1  Mar. 11, 2021

Related U.S. Application Data

(63) Continuation of application No. 15/228,380, filed on Aug. 4, 2016, now Pat. No. 10,874,511, which is a
(Continued)

(51) Int. Cl.
*A61F 2/24* (2006.01)
*A61M 25/10* (2013.01)
(Continued)

(52) U.S. Cl.
CPC ............ *A61F 2/2433* (2013.01); *A61B 5/065* (2013.01); *A61B 8/06* (2013.01); *A61F 2/012* (2020.05);
(Continued)

(58) Field of Classification Search
CPC .......... A61F 2/01; A61F 2/07; A61F 2/82–95; A61F 2002/011; A61F 2002/821–91591;
(Continued)

(56) References Cited

U.S. PATENT DOCUMENTS 4,655,771 A   4/1987 Wallsten
4,723,549 A   2/1988 Wholey et al.
(Continued)

FOREIGN PATENT DOCUMENTS

AU   2012335016 A1   5/2014
AU   2012335016 B2   7/2017
(Continued)

OTHER PUBLICATIONS

"Canadian Application Serial No. 3,082,091, Office Action dated Jun. 15, 2021", 4 pgs.
(Continued)

*Primary Examiner* — Robert A Lynch
*Assistant Examiner* — Mikail A Mannan
(74) *Attorney, Agent, or Firm* — Acuity IP, LLC; Nathan S. Cassell

(57) ABSTRACT

A method for deploying a medical device such as a heart valve to a desired location in a blood vessel comprising first deploying a tubular filter adjacent to at least one tributary vessel location with a filter deployment member, disengaging said deployment member and removing it, inserting an expandable sheath into the blood vessel, passing a medical device through said sheath to deploy its removing said sheath and removing said filter.

11 Claims, 67 Drawing Sheets

Related U.S. Application Data continuation of application No. 13/673,898, filed on Nov. 9, 2012, now Pat. No. 10,959,844.

(60) Provisional application No. 61/717,575, filed on Oct. 23, 2012, provisional application No. 61/558,397, filed on Nov. 10, 2011, provisional application No. 61/558,357, filed on Nov. 10, 2011.

(51) Int. Cl.
| | | |
|---|---|---|
| *A61B 5/06* | (2006.01) | |
| *A61B 8/06* | (2006.01) | |
| *A61M 25/00* | (2006.01) | |
| *A61F 2/01* | (2006.01) | |
| *A61F 2/95* | (2013.01) | |
| *A61M 25/06* | (2006.01) | |
| *A61F 2/06* | (2013.01) | |
| *A61B 90/00* | (2016.01) | |

(52) U.S. Cl.
CPC ............ *A61F 2/014* (2020.05); *A61F 2/2436* (2013.01); *A61F 2/95* (2013.01); *A61M 25/0023* (2013.01); *A61M 25/10* (2013.01); *A61M 25/1002* (2013.01); *A61B 2090/3966* (2016.02); *A61F 2/011* (2020.05); *A61F 2002/018* (2013.01); *A61F 2002/061* (2013.01); *A61F 2210/0057* (2013.01); *A61F 2210/0061* (2013.01); *A61F 2230/0021* (2013.01); *A61F 2250/001* (2013.01); *A61F 2250/0039* (2013.01); *A61M 25/0662* (2013.01); *A61M 2025/0024* (2013.01)

(58) Field of Classification Search
CPC .... A61F 2/2427; A61F 2/2439; A61F 2/2436; A61F 2/962; A61F 2/966; A61F 2/97
See application file for complete search history.

(56) References Cited

U.S. PATENT DOCUMENTS

| | | | |
|---|---|---|---|
| 4,954,126 | A | 9/1990 | Wallsten |
| 5,061,275 | A | 10/1991 | Wallsten et al. |
| 5,064,414 | A | 11/1991 | Revane |
| 5,221,261 | A | 6/1993 | Termin et al. |
| 5,290,295 | A | 3/1994 | Querals et al. |
| 5,415,664 | A | 5/1995 | Pinchuk |
| 5,527,282 | A | 6/1996 | Segal |
| 5,863,366 | A | 1/1999 | Snow |
| 5,911,702 | A | 6/1999 | Romley et al. |
| 5,941,896 | A | 8/1999 | Kerr |
| 5,997,508 | A | 12/1999 | Lunn et al. |
| 6,090,072 | A | 7/2000 | Kratoska et al. |
| 6,179,851 | B1 | 1/2001 | Barbut et al. |
| 6,692,462 | B2 | 2/2004 | Mackenzie et al. |
| 6,706,033 | B1 | 3/2004 | Martinez et al. |
| 7,014,647 | B2 | 3/2006 | Brady et al. |
| 7,766,820 | B2 | 8/2010 | Core |
| 8,206,280 | B2 | 6/2012 | Evans et al. |
| 8,591,539 | B2 | 11/2013 | Gellman |
| 9,370,438 | B2 | 6/2016 | Ginn |
| 9,545,298 | B2 | 1/2017 | Ginn et al. |
| 9,555,214 | B2 | 1/2017 | Ren et al. |
| 10,179,048 | B2 | 1/2019 | Marchand et al. |
| 10,729,544 | B2 | 8/2020 | Ginn et al. |
| 10,874,511 | B2 | 12/2020 | Ginn et al. |
| 10,959,844 | B2 | 3/2021 | Ginn |
| 2001/0041909 | A1 | 11/2001 | Tsugita et al. |
| 2001/0053929 | A1 | 12/2001 | Vonesh et al. |
| 2002/0016564 | A1 | 2/2002 | Courtney et al. |
| 2002/0035394 | A1 | 3/2002 | Fierens et al. |
| 2002/0077596 | A1 | 6/2002 | Mckenzie et al. |
| 2002/0077598 | A1 | 6/2002 | Yap et al. |
| 2002/0099431 | A1 | 7/2002 | Armstrong et al. |
| 2002/0138129 | A1 | 9/2002 | Armstrong et al. |
| 2003/0050658 | A1 | 3/2003 | Trask et al. |
| 2003/0144670 | A1 | 7/2003 | Pavcnik et al. |
| 2004/0153117 | A1 | 8/2004 | Clubb et al. |
| 2004/0215167 | A1 | 10/2004 | Belson |
| 2004/0260331 | A1 | 12/2004 | D'aquanni et al. |
| 2005/0021125 | A1 | 1/2005 | Stack et al. |
| 2005/0137696 | A1 | 6/2005 | Salahieh et al. |
| 2005/0149113 | A1 | 7/2005 | Douk et al. |
| 2005/0216053 | A1 | 9/2005 | Douk et al. |
| 2006/0052750 | A1 | 3/2006 | Lenker et al. |
| 2006/0135981 | A1 | 6/2006 | Lenker et al. |
| 2006/0149363 | A1 | 7/2006 | Kujawski |
| 2006/0271093 | A1 | 11/2006 | Holman et al. |
| 2006/0282154 | A1 | 12/2006 | Oepen et al. |
| 2007/0016280 | A1 | 1/2007 | Yacoby et al. |
| 2007/0244501 | A1 | 10/2007 | Horn et al. |
| 2008/0033521 | A1 | 2/2008 | Jorgensen et al. |
| 2008/0167705 | A1 | 7/2008 | Agnew |
| 2008/0188928 | A1 | 8/2008 | Salahieh et al. |
| 2008/0195137 | A1 | 8/2008 | Alleyne et al. |
| 2008/0243068 | A1 | 10/2008 | Ramzipoor |
| 2009/0005675 | A1 | 1/2009 | Grunwald et al. |
| 2009/0024202 | A1 | 1/2009 | Dave et al. |
| 2009/0137900 | A1 | 5/2009 | Bonner et al. |
| 2009/0182278 | A1 | 7/2009 | Eversull |
| 2009/0182360 | A1 | 7/2009 | Makower |
| 2009/0240202 | A1 | 9/2009 | Drasler et al. |
| 2009/0254169 | A1 | 10/2009 | Spenser et al. |
| 2009/0287182 | A1 | 11/2009 | Bishop et al. |
| 2010/0094392 | A1 | 4/2010 | Nguyen et al. |
| 2010/0100167 | A1 | 4/2010 | Bortlein et al. |
| 2010/0174355 | A1 | 7/2010 | Boyle et al. |
| 2010/0217304 | A1 | 8/2010 | Angel et al. |
| 2010/0234932 | A1 | 9/2010 | Arbefeuille et al. |
| 2010/0268264 | A1 | 10/2010 | Bonnette et al. |
| 2010/0305604 | A1 | 12/2010 | Pah |
| 2010/0312268 | A1 | 12/2010 | Belson |
| 2011/0015716 | A1 | 1/2011 | Silverman |
| 2011/0022076 | A1 | 1/2011 | Lashinski |
| 2011/0125258 | A1 | 5/2011 | Centola |
| 2011/0213459 | A1 | 9/2011 | Garrison et al. |
| 2011/0257592 | A1 | 10/2011 | Ventura et al. |
| 2012/0010151 | A1 | 4/2012 | Lenker et al. |
| 2012/0083877 | A1 | 4/2012 | Nguyen et al. |
| 2012/0172781 | A1 | 7/2012 | Wang |
| 2012/0172965 | A1 | 7/2012 | Kratzberg et al. |
| 2012/0209375 | A1 | 8/2012 | Madrid et al. |
| 2013/0131787 | A1 | 5/2013 | Ginn |
| 2013/0138201 | A1 | 5/2013 | Ginn |
| 2014/0336695 | A1 | 11/2014 | Naor et al. |
| 2014/0336752 | A1 | 11/2014 | Ginn et al. |
| 2016/0128723 | A1 | 5/2016 | Ginn et al. |
| 2016/0338828 | A1 | 11/2016 | Ginn |
| 2017/0014232 | A1 | 1/2017 | Ginn et al. |
| 2020/0360140 | A1 | 11/2020 | Ginn et al. |

FOREIGN PATENT DOCUMENTS

| | | |
|---|---|---|
| CA | 2855387 A1 | 5/2013 |
| CA | 3082091 C | 1/2023 |
| CN | 1204242 A | 1/1999 |
| CN | 104039381 A | 9/2014 |
| EP | 2663355 A1 | 11/2013 |
| EP | 2776114 A1 | 9/2014 |
| EP | 2776114 B1 | 10/2018 |
| EP | 3449969 A1 | 3/2019 |
| EP | 3449969 B1 | 2/2023 |
| FR | 2776114 A1 | 9/1999 |
| FR | 2776114 B1 | 10/2007 |
| JP | H09501594 A | 2/1997 |
| JP | H11501227 A | 2/1999 |
| JP | H11509130 A | 8/1999 |
| JP | 2001517973 A | 10/2001 |
| JP | 2002336261 A | 11/2002 |
| JP | 2003131159 A | 5/2003 |
| JP | 2003309379 A | 10/2003 |
| JP | 2004049545 A | 2/2004 |

(56) References Cited

FOREIGN PATENT DOCUMENTS

| | | |
|---|---|---|
| JP | 2004533290 A | 11/2004 |
| JP | 2005095242 A | 4/2005 |
| JP | 2005173366 A | 6/2005 |
| JP | 2006500970 A | 1/2006 |
| JP | 2008512181 A | 4/2008 |
| JP | 2008149619 A | 7/2008 |
| JP | 2009529401 A | 8/2009 |
| JP | 2009543655 A | 12/2009 |
| JP | 2011517592 A | 6/2011 |
| JP | 2012247510 A | 12/2012 |
| JP | 2013034867 A | 2/2013 |
| JP | 2013105107 A | 5/2013 |
| JP | 2015500681 A | 1/2015 |
| WO | WO-9505207 A2 | 2/1995 |
| WO | WO-9619941 A1 | 7/1996 |
| WO | WO-9721403 A1 | 6/1997 |
| WO | WO-9809678 A1 | 3/1998 |
| WO | WO-9924102 A1 | 5/1999 |
| WO | WO-0191844 A1 | 12/2001 |
| WO | WO-02056955 A1 | 7/2002 |
| WO | WO-03090834 A2 | 11/2003 |
| WO | WO-2005027751 A1 | 3/2005 |
| WO | WO-2007106755 A1 | 9/2007 |
| WO | WO-2009131612 A1 | 10/2009 |
| WO | 2010/045297 A2 | 4/2010 |
| WO | 2010/105195 A2 | 9/2010 |
| WO | WO-2011096975 A1 | 8/2011 |
| WO | WO-2013037505 A1 | 3/2013 |
| WO | WO-2013071179 A1 | 5/2013 |

OTHER PUBLICATIONS

"Canadian Application Serial No. 3,082,091, Response filed Oct. 12, 2021 to Office Action dated Jun. 15, 2021", 15 pgs.
"European Application Serial No. 18201608.9, Communication Pursuant to Article 94(3) EPC dated Mar. 31, 2021", 5 pgs.
"European Application Serial No. 18201808.9, Response filed Oct. 11, 2021 to Communication Pursuant to Article 94(3) EPC dated Mar. 31, 2021", 50 pgs.
"Japanese Application Serial No. 2020-038658, Notification of Reasons for Refusal dated Sep. 27, 2021", w/ English translation, 8 pgs.
EP Application No. 20200790.2, Extended European Search Report, dated Feb. 5, 2021, 7 pages.
"U.S. Appl. No. 13/673,898, Advisory Action dated Jul. 31, 2017", 3 pgs.
"U.S. Appl. No. 13/673,898, Advisory Action dated Aug. 5, 2016", 5 pgs.
"U.S. Appl. No. 13/673,898, Amendment filed Feb. 25, 2020", 8 pgs.
"U.S. Appl. No. 13/673,898, Appeal Brief filed Jul. 19, 2017", 19 pgs.
"U.S. Appl. No. 13/673,898, Appeal Brief filed Aug. 9, 2017", 2 pgs.
"U.S. Appl. No. 13/673,898, Appeal Decision dated Dec. 27, 2019", 26 pgs.
"U.S. Appl. No. 13/673,898, Examiner's Answer to Appeal Brief dated Dec. 19, 2017", 12 pgs.
"U.S. Appl. No. 13/673,898, Final Office Action dated Apr. 20, 2017", 20 pgs.
"U.S. Appl. No. 13/673,898, Final Office Action dated May 25, 2016", 10 pgs.
"U.S. Appl. No. 13/673,898, Non Final Office Action dated Apr. 3, 2020", 6 pgs.
"U.S. Appl. No. 13/673,898, Non Final Office Action dated Sep. 14, 2015", 11 pgs.
"U.S. Appl. No. 13/673,898, Non Final Office Action dated Nov. 16, 2016", 16 pgs.
"U.S. Appl. No. 13/673,898, Notice of Allowance dated Sep. 18, 2020" pp. 1-8.

"U.S. Appl. No. 13/673,898, Notice of Non-Complaint Appeal Brief dated Aug. 2, 2017", 2 pgs.
"U.S. Appl. No. 13/673,898, Reply Brief filed Jan. 30, 2018", 9 pgs.
"U.S. Appl. No. 13/673,898, Response filed Feb. 5, 2016 to Non Final Office Action dated Sep. 14, 2015", 8 pgs.
"U.S. Appl. No. 13/673,898, Response filed Jun. 2, 2017 to Final Office Action dated Apr. 20, 2017", 6 pgs.
"U.S. Appl. No. 13/673,898, Response filed Jun. 14, 2016 to Final Office Action dated May 25, 2016", 10 pgs.
"U.S. Appl. No. 13/673,898, Response filed Jun. 30, 2020 to Non Final Office Action dated Apr. 3, 2020", 8 pgs.
"U.S. Appl. No. 13/673,898, Response filed Aug. 7, 2015 to Restriction Requirement dated Mar. 20, 2015", 5 pgs.
"U.S. Appl. No. 13/673,898, Response filed Aug. 8, 2016 to Advisory Action dated Aug. 5, 2016", 10 pgs.
"U.S. Appl. No. 13/673,898, Response filed Dec. 22, 2016 to Non Final Office Action dated Nov. 16, 2016", 11 pgs.
"U.S. Appl. No. 13/673,898, Restriction Requirement dated Mar. 20, 2015", 6 pgs.
"U.S. Appl. No. 13/673,911, Advisory Action dated Feb. 16, 2016", 3 pgs.
"U.S. Appl. No. 13/673,911, Final Office Action dated Dec. 18, 2015", 6 pgs.
"U.S. Appl. No. 13/673,911, Non Final Office Action dated Apr. 6, 2015", 11 pgs.
"U.S. Appl. No. 13/673,911, Notice of Allowance dated Mar. 11, 2016", 9 pgs.
"U.S. Appl. No. 13/673,911, Response filed Jan. 28, 2016 to Final Office Action dated Dec. 18, 2015", 8 pgs.
"U.S. Appl. No. 13/673,911, Response filed Mar. 1, 2016 to Advisory Action dated Feb. 16, 2016", 7 pgs.
"U.S. Appl. No. 13/673,911, Response filed Sep. 8, 2015 to Non Final Office Action dated Apr. 4, 2015", 7 pgs.
"U.S. Appl. No. 14/274,563, 312 Amendment filed Aug. 9, 2016", 16 pgs.
"U.S. Appl. No. 14/274,563, 312 Amendment filed Aug. 12, 2016", 3 pgs.
"U.S. Appl. No. 14/274,563, Advisory Action dated Jun. 3, 2016", 3 pgs.
"U.S. Appl. No. 14/274,563, Final Office Action dated Mar. 28, 2016", 19 pgs.
"U.S. Appl. No. 14/274,563, Non Final Office Action dated Jun. 3, 2015", 15 pgs.
"U.S. Appl. No. 14/274,563, Non Final Office Action dated Sep. 8, 2014", 7 pgs.
"U.S. Appl. No. 14/274,563, Notice of Allowance dated Aug. 8, 2016", 11 pgs.
"U.S. Appl. No. 14/274,563, PTO Response to Rule 312 Communication dated Sep. 26, 2016", 2 pgs.
"U.S. Appl. No. 14/274,563, Response filed Feb. 9, 2015 to Non Final Office Action dated Sep. 8, 2014", 13 pgs.
"U.S. Appl. No. 14/274,563, Response filed Apr. 29, 2016 to Final Office Action dated Mar. 28, 2016", 9 pgs.
"U.S. Appl. No. 14/274,563, Response filed Jun. 15, 2016 to Advisory Action dated Jun. 3, 2016", 9 pgs.
"U.S. Appl. No. 14/274,563, Response filed Oct. 20, 2015 to Non Final Office Action dated Jun. 3, 2015", 11 pgs.
"U.S. Appl. No. 14/934,767, Advisory Action dated May 23, 2019", 3 pgs.
"U.S. Appl. No. 14/934,767, Examiner Interview Summary dated May 14, 2018", 3 pgs.
"U.S. Appl. No. 14/934,767, Final Office Action dated Jan. 31, 2020", 21 pgs.
"U.S. Appl. No. 14/934,767, Final Office Action dated Apr. 25, 2019", 26 pgs.
"U.S. Appl. No. 14/934,767, Non Final Office Action dated May 3, 2018", 18 pgs.
"U.S. Appl. No. 14/934,767, Non Final Office Action dated Aug. 20, 2019", 17 pgs.
"U.S. Appl. No. 14/934,767, Response filed Mar. 5, 2018 to Restriction Requirement dated Jan. 8, 2018", 2 pgs.
"U.S. Appl. No. 14/934,767, Response filed May 10, 2019 to Final Office Action dated Apr. 25, 2019", 12 pgs.

(56) References Cited

OTHER PUBLICATIONS

"U.S. Appl. No. 14/934,767, Response filed Jul. 24, 2018 to Non Final Office Action dated May 3, 2018", 11 pgs.
"U.S. Appl. No. 14/934,767, Response filed Nov. 11, 2019 to Non Final Office Action dated Aug. 20, 2019", 11 pgs.
"U.S. Appl. No. 14/934,767, Restriction Requirement dated Jan. 8, 2018", 7 pgs.
"U.S. Appl. No. 15/228,380, Final Office Action dated Feb. 21, 2020", 10 pgs.
"U.S. Appl. No. 15/228,380, Final Office Action dated Nov. 14, 2018", 8 pgs.
"U.S. Appl. No. 15/228,380, Non Final Office Action dated Apr. 20, 2018", 7 pgs.
"U.S. Appl. No. 15/228,380, Non Final Office Action dated Jun. 26, 2019", 8 pgs.
"U.S. Appl. No. 15/228,380, Notice of Allowance dated Aug. 21, 2020", 8 pgs.
"U.S. Appl. No. 15/228,380, Response filed Feb. 14, 2019 to Final Office Action dated Nov. 14, 2018", 6 pgs.
"U.S. Appl. No. 15/228,380, Response Filed May 21, 2020 to Final Office Action dated Feb. 21, 2020", 9 pgs.
"U.S. Appl. No. 15/228,380, Response filed Jun. 26, 2018 to Non Final Office Action dated Apr. 20, 2018", 7 pgs.
"U.S. Appl. No. 15/228,380, Response filed Oct. 24, 2019 to Non Final Office Action dated Jun. 26, 2019", 7 pgs.
"U.S. Appl. No. 15/232,318, Examiner Interview Summary dated Nov. 20, 2018", 3 pgs.
"U.S. Appl. No. 15/232,318, Final Office Action dated Oct. 18, 2019", 10 pgs.
"U.S. Appl. No. 15/232,318, Final Office Action dated Nov. 1, 2018", 12 pgs.
"U.S. Appl. No. 15/232,318, Non Final Office Action dated Apr. 4, 2019", 10 pgs.
"U.S. Appl. No. 15/232,318, Non Final Office Action dated Apr. 6, 2018", 13 pgs.
"U.S. Appl. No. 15/232,318, Notice of Allowance dated Feb. 18, 2020", 7 pgs.
"U.S. Appl. No. 15/232,318, Preliminary Amendment filed Aug. 12, 2016", 3 pgs.
"U.S. Appl. No. 15/232,318, Response filed Jan. 20, 2020 to Final Office Action dated Oct. 18, 2019", 8 pgs.
"U.S. Appl. No. 15/232,318, Response filed Feb. 1, 2019 to Final Office Action dated Nov. 1, 2018", 10 pgs.
"U.S. Appl. No. 15/232,318, Response filed Jun. 19, 2018 to Non Final Office Action dated Apr. 6, 2018", 9 pgs.
"U.S. Appl. No. 15/232,318, Response filed Jul. 5, 2019 to Non Final Office Action dated Apr. 4, 2019", 10 pgs.
"Australian Application Serial No. 2012335016, First Examiner Report dated Jul. 17, 2016", 3 pgs.
"Australian Application Serial No. 2012335016, Response filed Jan. 12, 2017 to First Examiner Report dated Jul. 17, 2016", 17 pgs.
"Australian Application Serial No. 2012335016, Response filed Apr. 12, 2017 to Second Examiner Report dated Feb. 20, 2017", 8 pgs.
"Australian Application Serial No. 2012335016, Response filed Jun. 29, 2017 to Third Examiner Report dated Jun. 12, 2017", 11 pgs.
"Australian Application Serial No. 2012335016, Second Examiner Report dated Feb. 20, 2017", 3 pgs.
"Australian Application Serial No. 2012335016, Third Examiner Report dated Jun. 12, 2017", 4 pgs.
"Canadian Application Serial No. 2,855,387, Office Action dated Jun. 12, 2018", 4 pgs.
"Canadian Application Serial No. 2,855,387, Office Action dated Mar. 8, 2019", 4 pgs.
"Canadian Application Serial No. 2,855,387, Response filed Sep. 6, 2019 to Office Action dated Mar. 8, 2019", 78 pgs.
"Canadian Application Serial No. 2,855,387, Response filed Dec. 12, 2018 to Office Action dated Jun. 12, 2018", 27 pgs.
"Canadian Application Serial No. 2,855,387, Voluntary Amendment filed Oct. 29, 2019", 14 pgs.
"Canadian Application Serial No. 3,082,091, Voluntary Amendment Filed Oct. 21, 2020", 15 pgs.
"Chinese Application Serial No. 201280066517.X, Office Action dated Oct. 26, 2015", with English translation of claims, 17 pgs.
"European Application Serial No. 12847961.5, Communication Pursuant to Article 94(3) EPC dated Mar. 29, 2016", 5 pgs.
"European Application Serial No. 12847961.5, Communication Pursuant to Article 94(3) EPC dated Aug. 17, 2017", 6 pgs.
"European Application Serial No. 12847961.5, Communication Pursuant to Article 94(3) EPC dated Nov. 15, 2016", 5 pgs.
"European Application Serial No. 12847961.5, Extended European Search Report dated May 22, 2015", 8 pgs.
"European Application Serial No. 12847961.5, Intention to Grant mailed Apr. 26, 2018", 95 pgs.
"European Application Serial No. 12847961.5, Intention to Grant mailed Sep. 17, 2018", 95 pgs.
"European Application Serial No. 12847961.5, Response filed Jan. 2, 2015 to Communication Pursuant to Rules 161(1) and 162 EPC dated Jun. 23, 2014", 11 pgs.
"European Application Serial No. 12847961.5, Response filed May 24, 2017 to Communication Pursuant to Article 94(3) EPC dated Nov. 15, 2016", 52 pgs.
"European Application Serial No. 12847961.5, Response filed Sep. 5, 2018 to Intention to Grant mailed Apr. 26, 2018", 8 pgs.
"European Application Serial No. 12847961.5, Response filed Oct. 10, 2016 to Communication Pursuant to Article 94(3) EPC dated Mar. 29, 2016", 13 pgs.
"European Application Serial No. 12847961.5, Response filed Dec. 21, 2015 to Extended European Search Report dated May 22, 2015", 12 pgs.
"European Application Serial No. 12847961.5, Response filed Dec. 29, 2017 to Communication Pursuant to Article 94(3) EPC dated Aug. 17, 2017", 52 pgs.
"European Application Serial No. 14797200.4, Extended European Search Report dated Nov. 7, 2016", 8 pgs.
"European Application Serial No. 14797200.4, Response filed Jun. 6, 2017 to Extended European Search Report dated Nov. 7, 2016", 21 pgs.
"European Application Serial No. 18201608.9, Extended European Search Report dated Feb. 1, 2019", 10 pgs.
"International Application Serial No. PCT/US2012/064540, International Preliminary Report on Patentability dated May 22, 2014", 11 pgs.
"International Application Serial No. PCT/US2012/064540, International Search Report dated Feb. 6, 2013", 2 pgs.
"International Application Serial No. PCT/US2012/064540, Written Opinion dated Feb. 6, 2013", 9 pgs.
"International Application Serial No. PCT/US2014/037580, International Preliminary Report on Patentability dated Nov. 19, 2015", 8 pgs.
"International Application Serial No. PCT/US2014/037924, International Search Report dated Oct. 17, 2014", 2 pgs.
"Israel Application Serial No. 232542, Office Action dated Sep. 4, 2018", with Concise Statement of Relevance, 5 pgs.
"Israel Application Serial No. 232542, Office Action dated Sep. 18, 2017", with Concise Statement of Relevance, 3 pgs.
"Israel Application Serial No. 232542, Response filed Jan. 18, 2018 to Office Action dated Sep. 18, 2017", with Concise Statement of Relevance, 2 pgs.
"Israel Application Serial No. 232542, Response filed Dec. 16, 2018 to Office Action dated Sep. 4, 2018", with Concise Statement of Relevance, 2 pgs.
"Israel Application Serial No. 242506, Office Action dated May 27, 2019", with English translation, 7 pgs.
"Japanese Application Serial No. 2014-541354, Notice of Reason for Rejection dated Jul. 28, 2016", w/ English Translation, 22 pgs.
"Japanese Application Serial No. 2017-005031, Notice of Reasons for Rejection dated Oct. 23, 2017", with English translation of claims, 37 pgs.
"Japanese Application Serial No. 2017-005031, Office Action dated Jan. 25, 2018", with English translation of claims, 5 pgs.
"U.S. Appl. No. 16/884,760, Final Office Action dated Feb. 16, 2023", 10 pgs.

(56) References Cited

OTHER PUBLICATIONS

"U.S. Appl. No. 16/884,760, Non Final Office Action dated Jun. 23, 2022", 4 pgs.
"U.S. Appl. No. 16/884,760, Response filed Oct. 21, 22 to Non Final Office Action dated Jun. 23, 2022", 9 pgs.
"Canadian Application Serial No. 3,082,091, Office Action dated Dec. 3, 2021", 3 pgs.
"Canadian Application Serial No. 3,082,091, Response filed Mar. 16, 2022 to Office Action dated Dec. 3, 2021", 7 pgs.
"U.S. Appl. No. 16/884,760, Advisory Action dated Jun. 27, 2023", 3 pgs.
"U.S. Appl. No. 16/884,760, Response filed May 16, 23 to Final Office Action dated Feb. 16, 2023", 11 pgs.
"European Application Serial No. 23153606.1, Extended European Search Report dated Apr. 19, 2023", 9 pgs.

SYSTEM FOR DEPLOYING A DEVICE TO A DISTAL LOCATION ACROSS A DISEASED VESSEL

RELATED APPLICATION DATA

The present application is a continuation of U.S. patent application Ser. No. 15/228,380 filed Aug. 4, 2016, which is a continuation of U.S. patent application Ser. No. 13/673,898, filed Nov. 9, 2012, which claims the benefit under 35 U.S.C. § 119 to U.S. Provisional Application Ser. No. 61/558,397, filed Nov. 10, 2011; U.S. Provisional Application Ser. No. 61/558,357, filed Nov. 10, 2011; and U.S. Provisional Application Ser. No. 61/717,575, filed Oct. 23, 2012. The foregoing applications are hereby incorporated by reference into the present application in their entirety.

FIELD OF THE INVENTION

The present invention relates generally to medical interventions conducted through vessels such as the major arteries, and more particularly to access and deployment configurations for conducting percutaneous procedures such as percutaneous valve replacement.

BACKGROUND

Gaining access to the heart is a continued challenge in cardiovascular medicine. Conventional procedures for accomplishing tasks such as valve replacement generally involve a thoracotomy and/or creation of one or more access ports across the wall of the heart itself, which is relatively highly invasive and therefore undesirable. Recent progress has been made in the area of percutaneous intervention, wherein instrumentation, such as catheters, guidewires, and prostheses, are brought to the heart through the vessels connected to the heart. One of the challenges with percutaneous approaches to procedures such as valve replacement, is that patients with diseased valves often have diseased major vessels, and the instrumentation required to accomplish a procedure such as a percutaneous valve replacement is often fairly large. For example, the un-expanded delivery size of a CoreValve® aortic valve prosthesis available from Medtronic, Inc. is approximately 18 French; the un-expanded delivery size of a Sapien® valve available from Edwards Lifesciences, Inc. is between 18 and 24 French, depending upon which size is utilized. Such outer sizes do not allow for a conventional guide catheter to be inserted as a protective layer between the tools and the tissue, and therefore the standard of care has become direct insertion of the valve instrumentation through the diseased vessels to reach the target location within or adjacent to the heart. Another complicating factor with such interventions is the fact that it is likely that the aorta through which the devices will be advanced will be diseased (one recent study concluded that 61% of patients over 65 years of age with severe aortic valve stenosis also have severe aortic atherosclerosis; Osranek et al., American Journal of Cardiology, 2009; 103: 713-717). FIG. 1 illustrates a typical diseased aorta (2) with deposits (4) clinging to almost all interior surfaces. This complicated surgical paradigm has led some clinical researchers to believe that elevated stroke rates associated with such procedures may be related to the physical insertion of large interventional tools through diseased vessels and concomitant scraping or microscraping action of the tools against the diseased vessel walls, which is breaking portions of plaque loose and allowing these to flow with the bloodstream into the brain and other undesirable landing places. There is a need for a configuration wherein a relatively thin but protective sheath-like member can be put in place to guide the interventional tools and prosthesis while mitigating load concentrations and/or scraping or abrasion of the interior of the subject vessels.

The subject invention is directed to address such need.

SUMMARY

One embodiment is directed to a method for deploying a device to a distal location across a diseased vessel, comprising inserting a railed expandable sheath into a diseased vessel at a point of entry, the sheath defining a lumen there-through and comprising two or more longitudinal rail structures coupled to a sheet-like member, the sheath having a collapsed configuration, wherein the sheath has a first cross-sectional outer diameter defines a first lumen inner diameter, and an expanded configuration, wherein the sheath has a second cross-sectional outer diameter and second lumen inner diameter, such that in the collapsed configuration, the sheath is configured to be advanced across at least a portion of the diseased vessel to a position adjacent the distal location without substantial size interference between the first cross-sectional outer diameter of the sheath and an inner diameter profile of a lumen of the diseased vessel; and upon positioning the collapsed configuration to the desired position relative to the distal location, the sheath may be expanded to the expanded configuration with incremental pushing of a device longitudinally through the lumen such that loads imparted upon the sheath by the device are transferred to the rails and distributed to nearby portions of the diseased vessel in a deconcentrated and nonabrasive manner; inserting the device through the lumen to transform the sheath into the expanded configuration. The method further may comprise deploying an emboli filter into the diseased vessel at a location opposite of the sheath point of entry from the distal location. The method further may comprise deploying one or more emboli filters into the diseased vessel to capture emboli which may exit the diseased vessel to associated tributary vessels. The method further may comprise observing one or more radiopaque markers which may be coupled to one or more locations upon the sheath using fluoroscopy while inserting the railed expandable sheath, the markers being configured to be associated with a designated anatomical structure comprising the diseased vessel. The sheet-like member may comprise one or more porous regions configured to allow blood to flow from a position within the lumen to a position across the sheet-like member and outside of the sheath, and inserting may comprise positioning the one or more porous regions adjacent one or more anatomical structures. The one or more porous regions may be configured to be aligned with tributary vessels that join the diseased vessel. The method further may comprise examining a flow pattern adjacent the sheath and designated anatomical structure using Doppler ultrasonic analysis. The ultrasonic analysis may be conducted using a transcutaneous ultrasound transducer. The ultrasonic analysis may be conducted using an intravascular ultrasound transducer which may be coupled to an elongate probe configured to be placed through the lumen of the sheath. Inserting the device may comprise pressing one or more surfaces of the device against exposed portions of the rail structures of the sheath to move the rail structures away from each other into the expanded configuration as the device is advanced. The method further may comprise inserting a balloon dilatation probe into the lumen to complete the reconfiguration of the railed expandable sheath from the collapsed configuration to the expanded configuration. The railed expandable sheath may be self-expanding from the collapsed configuration to the expanded configuration, and the method further may comprise removing a removable expansion retention member configured to retain the railed expandable sheath in the collapsed configuration. The expansion retention member may comprise a corset and tensile member assembly, and the method further may comprise tensioning the tensile member proximally to release the corset and allow expansion to the expanded configuration. The method further may comprise inserting a guidewire through the diseased vessel and using the guidewire to assist with guiding the sheath by advancing the lumen over the guidewire. One or more portions of the rail structures may comprise a ferromagnetic material, and the method further may comprise passing a magnetic probe through the lumen of the expanded configuration to assist with affirmative collapsing of the sheath back to the collapsed configuration. One or more portions of the rail structures may comprise a ferromagnetic material, and the method further may comprise retaining a magnetic probe through the lumen of the expanded configuration to maintain the collapsed configuration until transformation to the expanded configuration is desired. The method further may comprise retracting the sheath out of the point of entry. Inserting the railed expandable sheath may comprise manually manipulating a proximal portion of the sheath to advance the sheath into the diseased vessel. Inserting the railed expandable sheath may comprise manually advancing an elongate probe that is coupled to the railed expandable sheath relative to the diseased vessel. The sheath may comprise two diametrically opposed rail structures coupled to the sheet-like member. The sheath may comprise three rail structures distributed circumferentially equidistantly. The sheath may comprise four rail structures distributed circumferentially equidistantly. The first lumen inner diameter may be equal to between about 0 mm and about 3 mm. The second lumen inner diameter may be equal to between about 6 mm and about 8 mm. The rail structures may comprise a material selected from the group consisting of: polyethylene, ultra-high-molecular weight polyethylene, polyethylene terephthalate, polyoxymethylene, polytetrafluoroethylene, and co-polymers thereof. The rail structures may comprise Nitinol alloy. The rail structures may be coated with a lubricious coating. The sheet-like member may comprise a material selected from the group consisting of: polyethylene, polytetrafluoroethylene, and co-polymers thereof. The diseased vessel may be an aorta. The device may be an implantable prosthesis. The implantable prosthesis may be a cardiac valve. The distal location may be a location within a heart coupled to the diseased vessel. The sheath may be placed across substantially the full length of the aorta between the point of entry and a heart coupled to the aorta. The sheath may be placed across only a portion of the length of the aorta between the point of entry and a heart coupled to the aorta. The sheath may be placed up to, but not across, the carotid artery takeoffs from the aorta. The point of entry may be in a femoral artery coupled to the aorta, and the first cross-sectional outer diameter may be configured to accommodate insertion through the femoral artery. Expanding the sheath to the expanded configuration may comprise unwinding a built up twisting configuration that has been created to maintain the collapsed configuration.

BRIEF DESCRIPTION OF THE DRAWINGS

FIGS. 5A-5K illustrate aspects of a configuration similar to that of FIGS. 3A-3Z-4, wherein a tubular branch vessel protection filter is also incorporated.

DETAILED DESCRIPTION

Figure 1A:
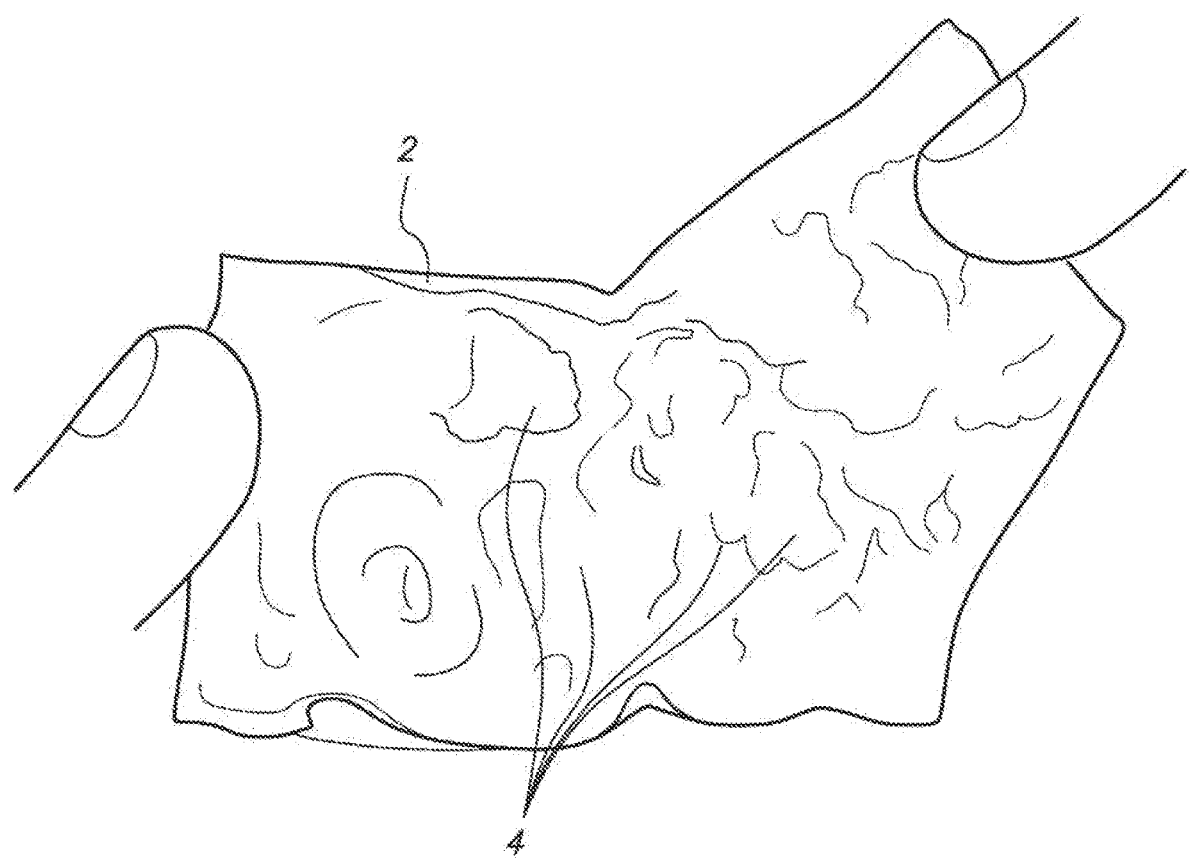
FIGS. 1A-1B illustrate various portions of a diseased aorta.
Figure 1B:
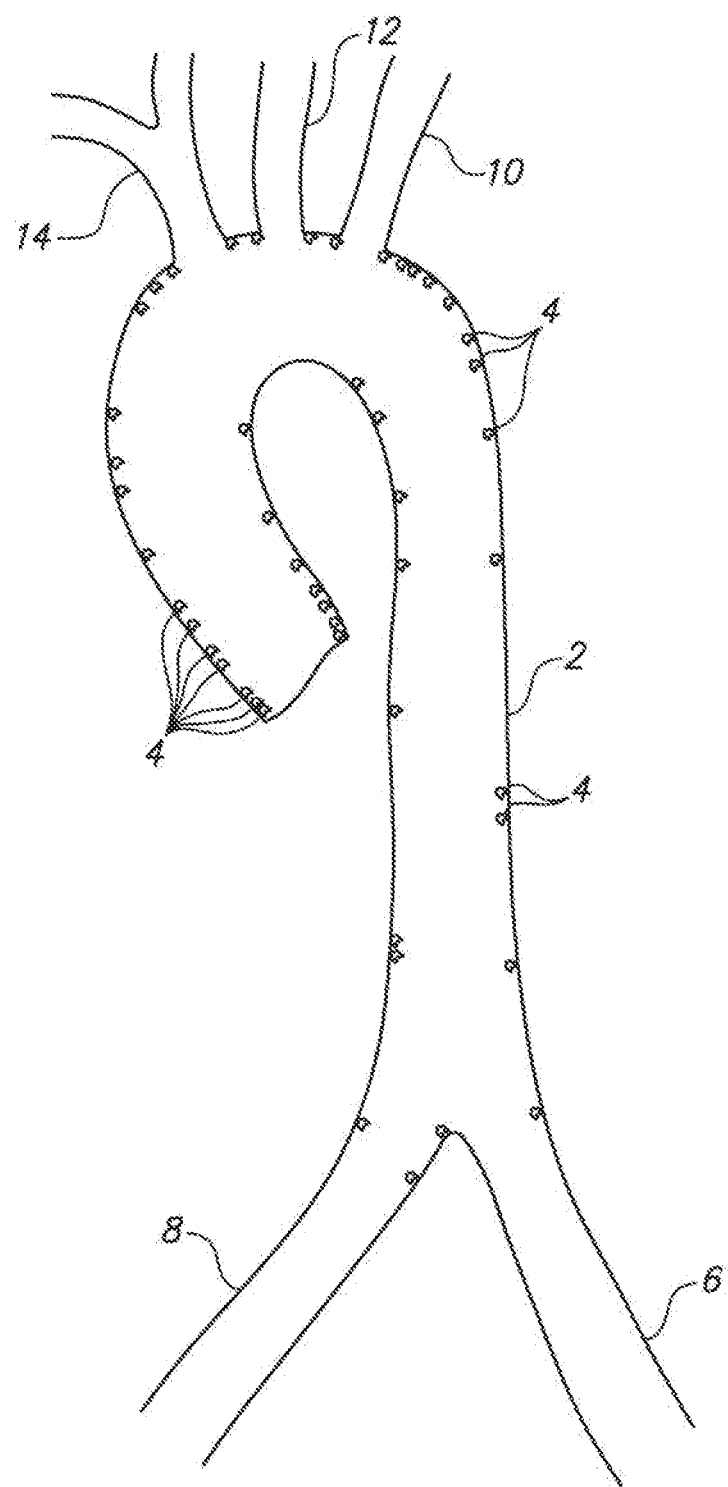
Figure 2A:
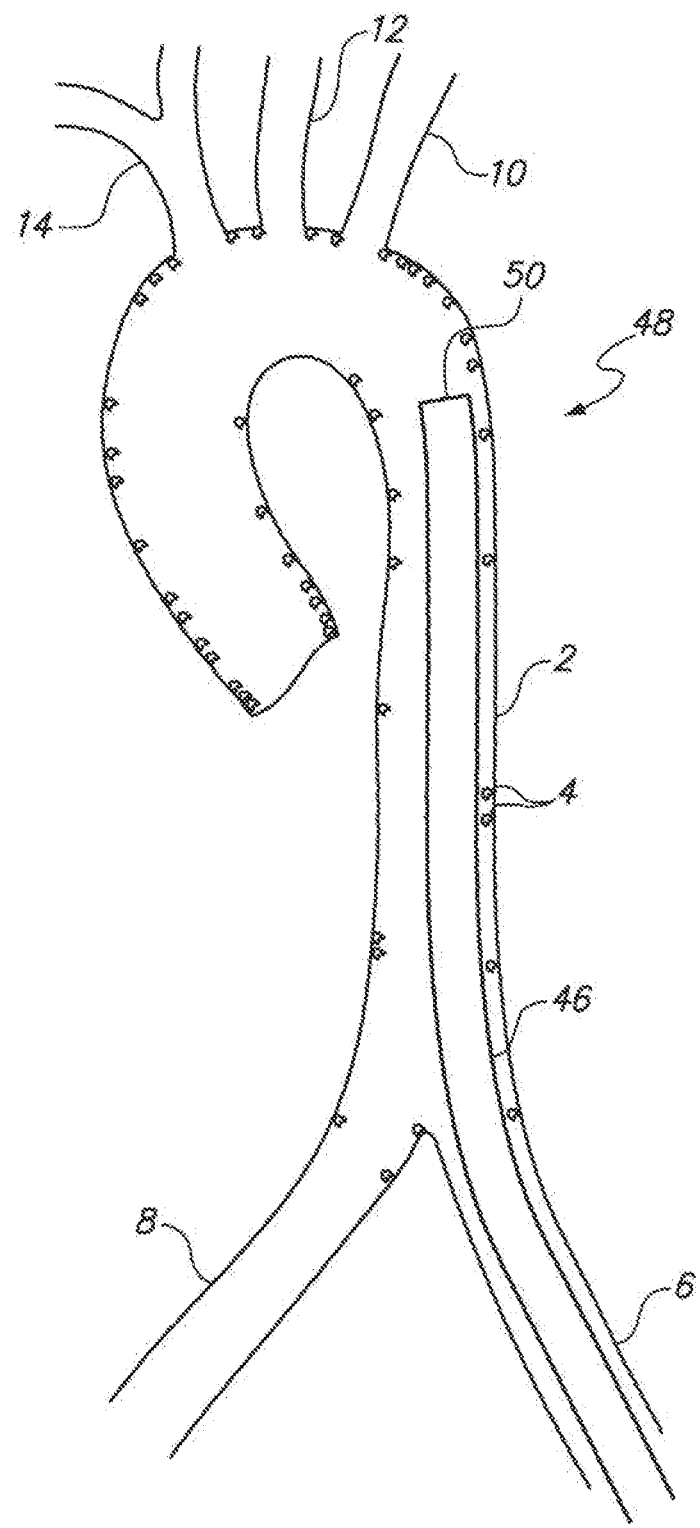
FIGS. 2A-2F illustrate aspects of a conventional interventional device deployment through a diseased aorta.
Figure 2B:
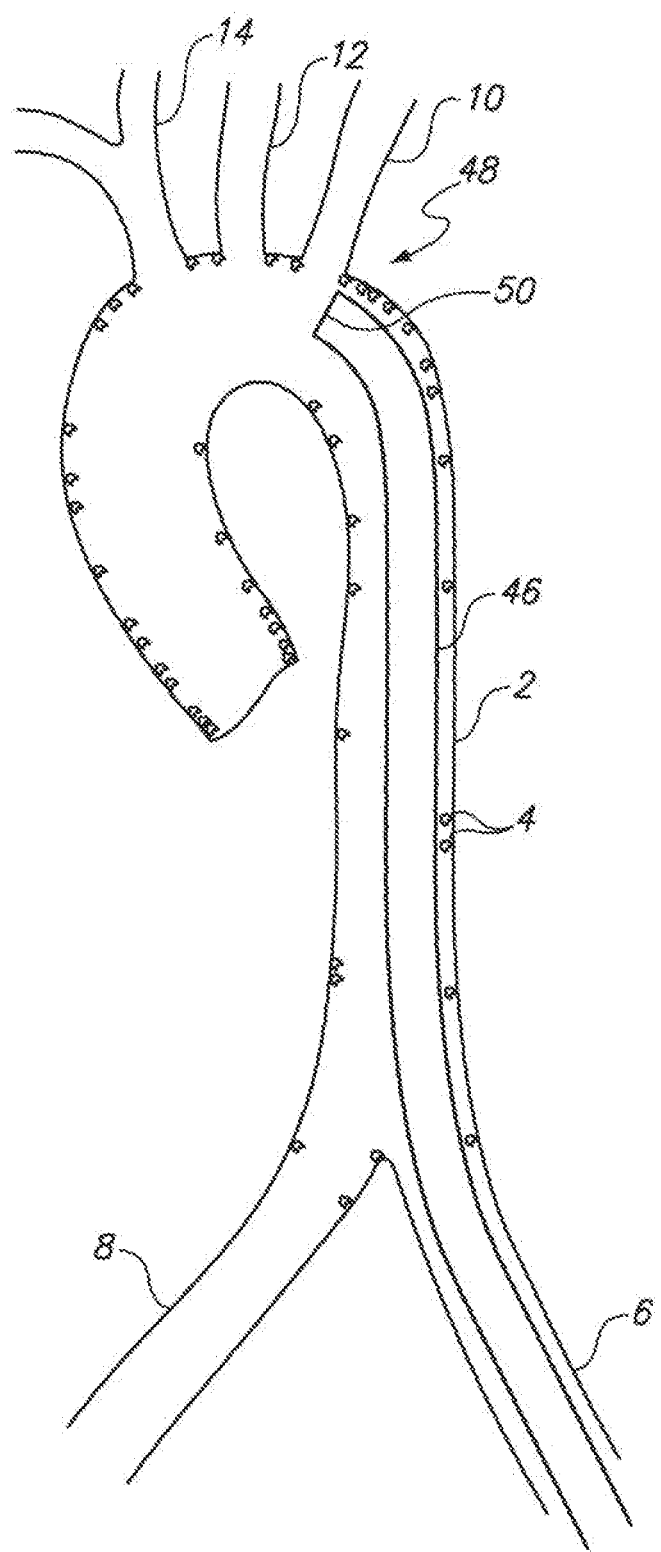
Figure 2C:
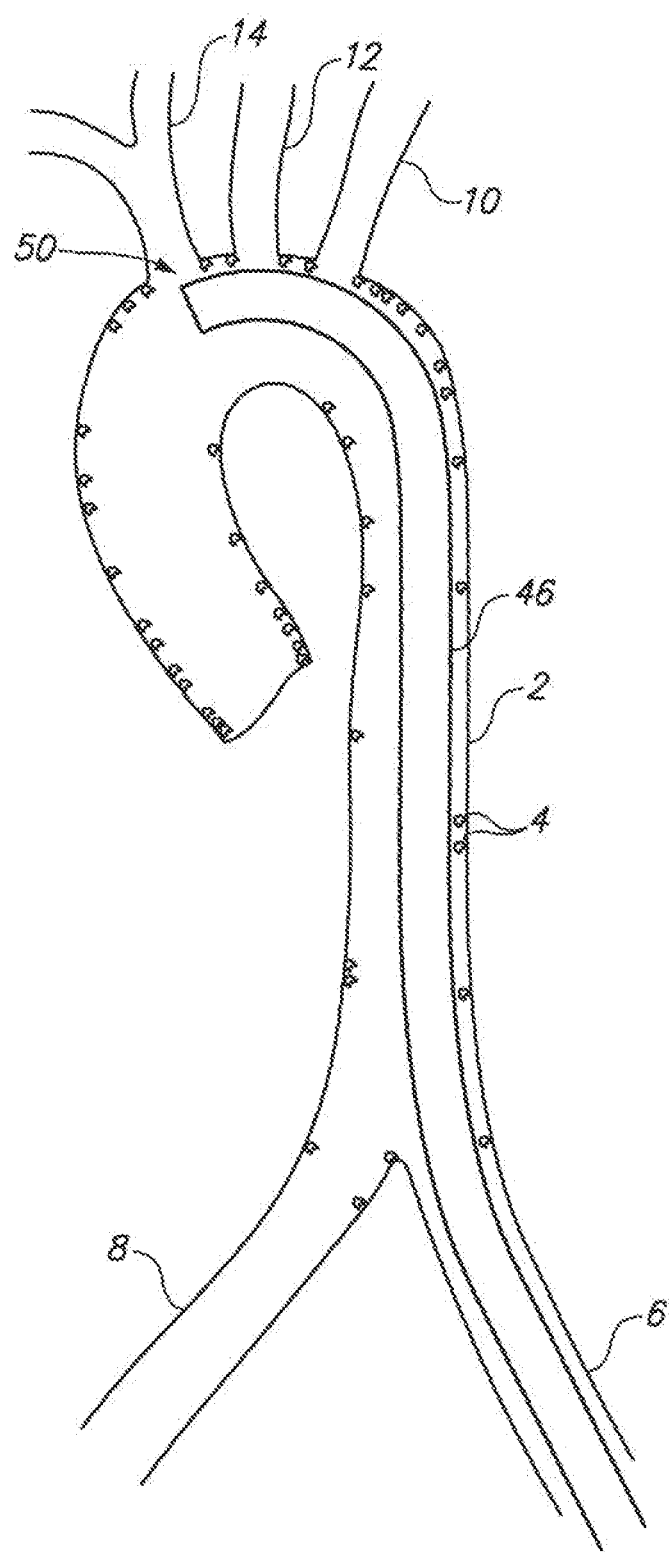
Figure 2D:
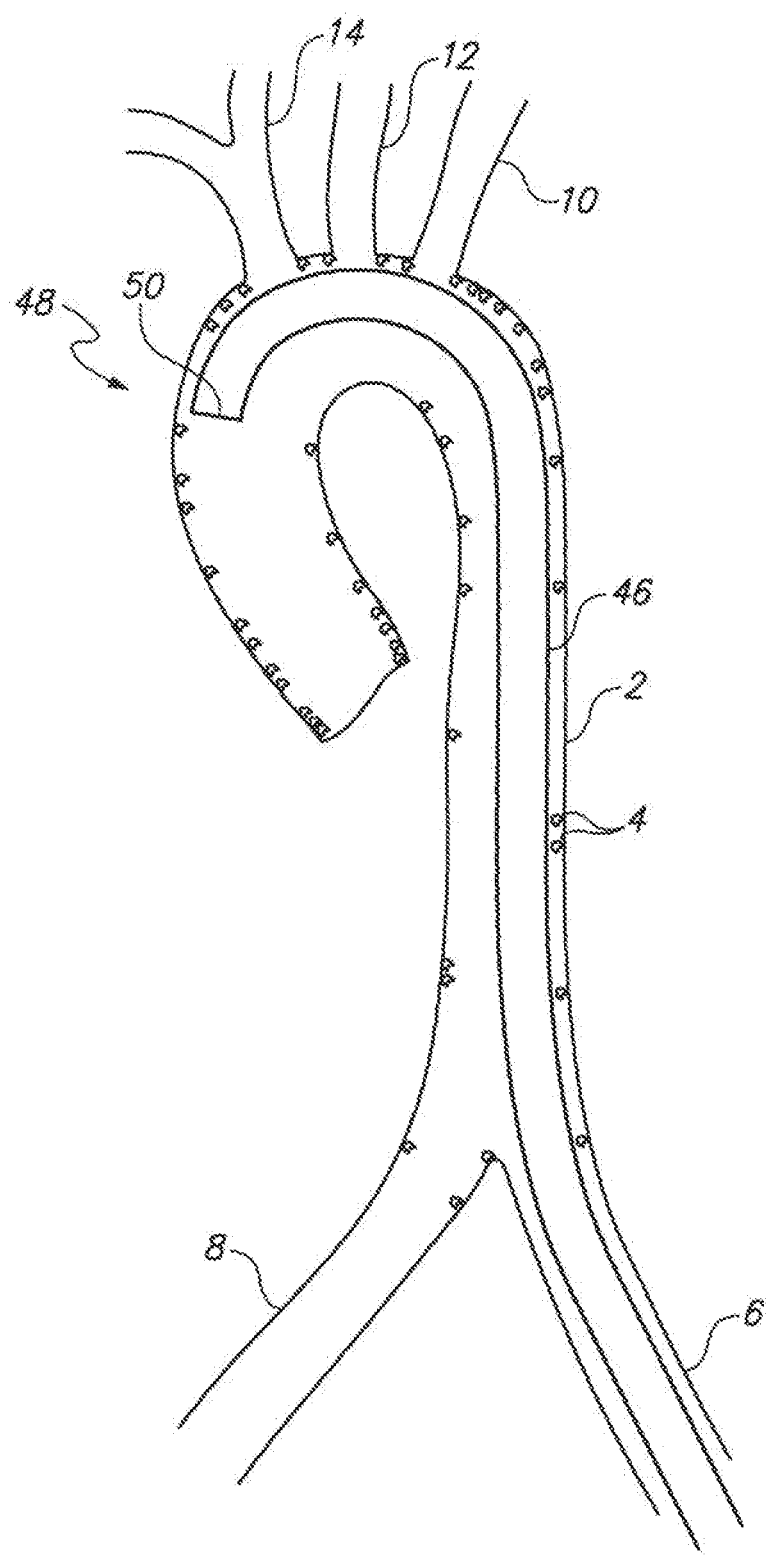
Figure 2E:
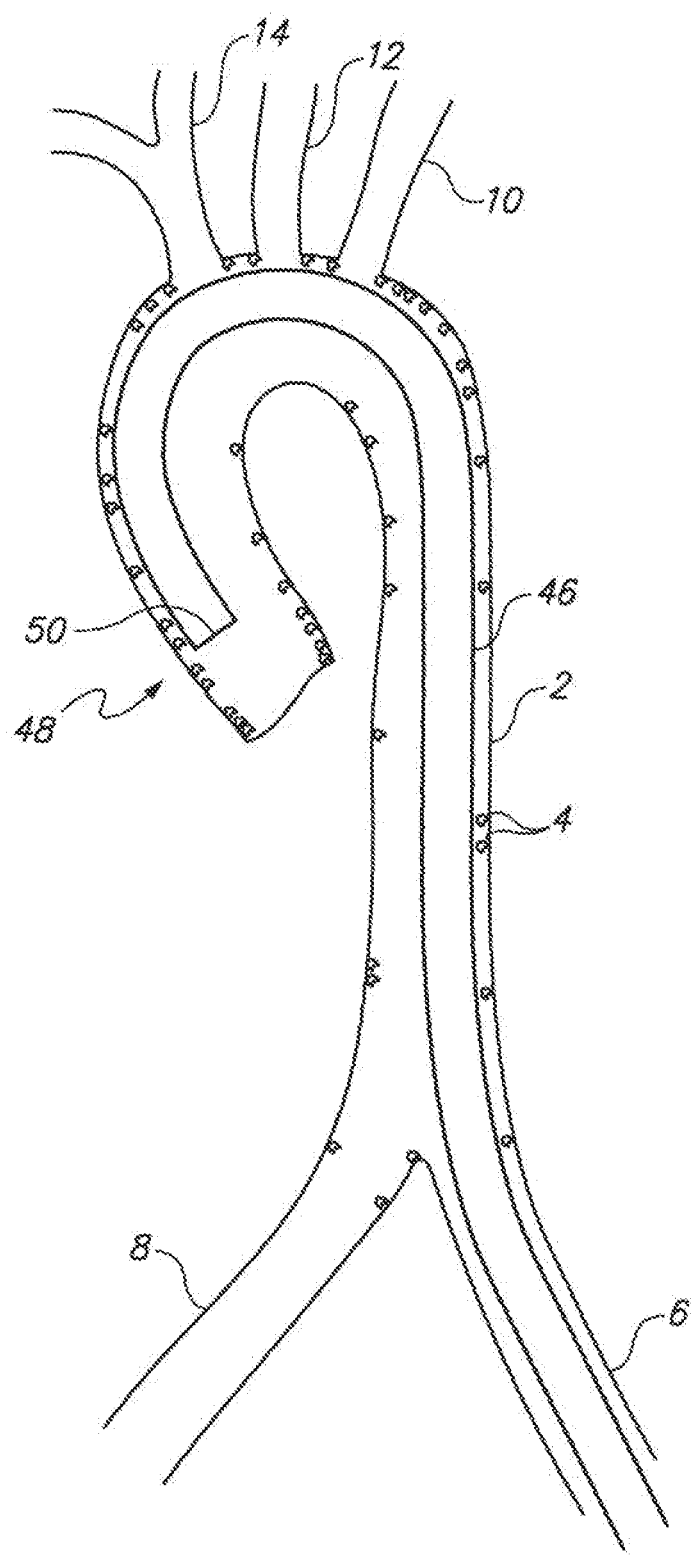
Figure 2F:
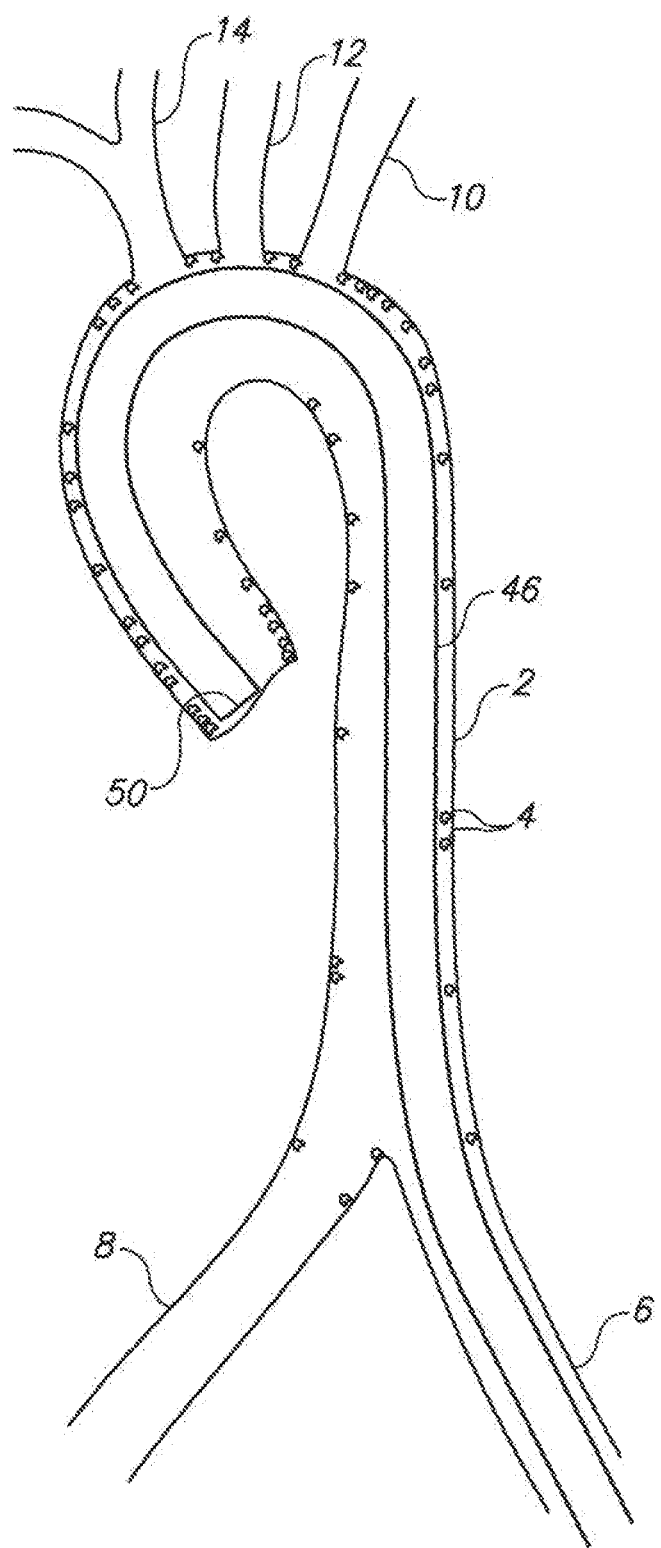

Referring to FIG. 1B, an illustrative representation of a diseased aorta (2) is shown with deposits (4) distributed in several locations, including adjacent or within the left (6) and right (8) iliac arteries, and adjacent the junctions of the aortic arch with the left subclavian (10), left common carotid (12), and innominate artery (14). Navigating a diseased aorta (2) such as that depicted is indeed a challenge with conventional intravascular diagnostic and/or interventional hardware. For example, referring to FIGS. 2A-2F, a conventional instrument deployment is illustrated to demonstrate the disease-related challenges. Referring to FIG. 2A, the elongate instrument (46) is advanced in a retrograde direction through the aorta (2) distal tip (50) first. The instrument (46) may be a valve deployment member or probe, a catheter or conduit for conducting various interventions, etc. Referring to FIG. 2B, as the instrument (46) is advanced farther toward the targeted anatomy, the distal end (50) may become a scraping interface (48) as it is urged past and against the tissue comprising the diseased aorta (2), and may accidentally and undesirably cause one or more pieces of the deposit material (4) to become loose and thereby flowing distally—perhaps into the brain or another undesirable deposit flow location. Further, the scraping dynamic between the distal tip (50) of the instrument (46) and the aortic tissue may result in the formation of one or more embolic masses, which also may find themselves undesirably drifting with the flow path toward the brain or other tissue. FIG. 2C shows that at the relatively extreme turning portions of the aortic arch, a conventional instrument may find itself located immediately adjacent or within the takeoff junctions of the joining arteries (10, 12, 14), where plaques and other deposits may be particularly mechanically vulnerable. FIGS. 2D-2F illustrate further advancement of the instrument (46) until the distal tip (50) is in the desired location for the planned diagnostic or interventional procedure. Subsequently, the instrumentation is typically retracted, causing yet another scraping interface type of interaction as the instrumentation is pulled proximally in a pathway opposite to that described in reference to FIGS. 2A-2F, and additional risks for undesirable complication related to such interaction.

Figure 3A:
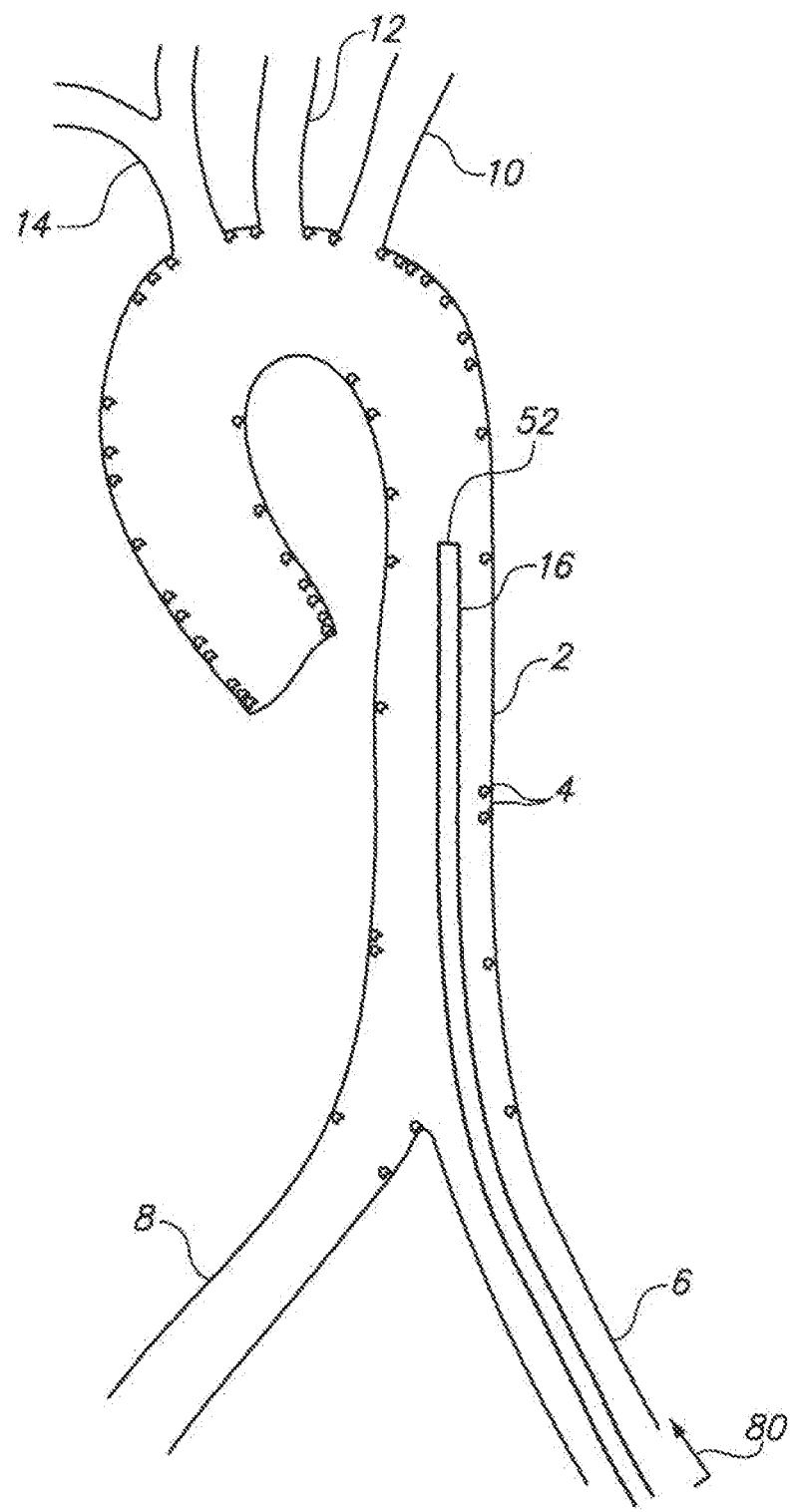
FIGS. 3A-3Z-4 illustrate various aspects of an inventive expandable railed sheath that may be used in conducting various cardiovascular procedures, such as a percutaneous aortic valve replacement procedure.
Figure 3B:
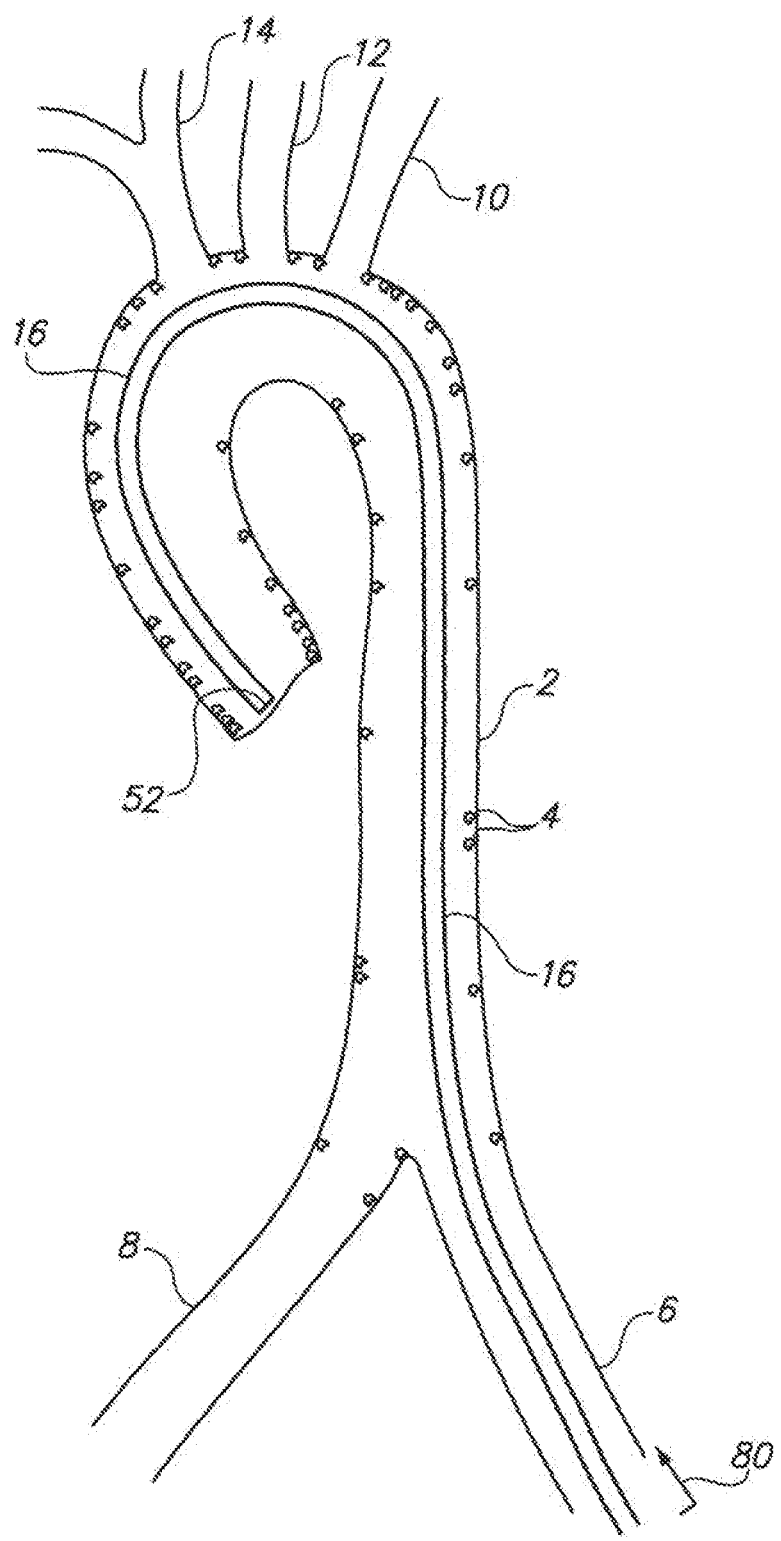
Figure 3C:
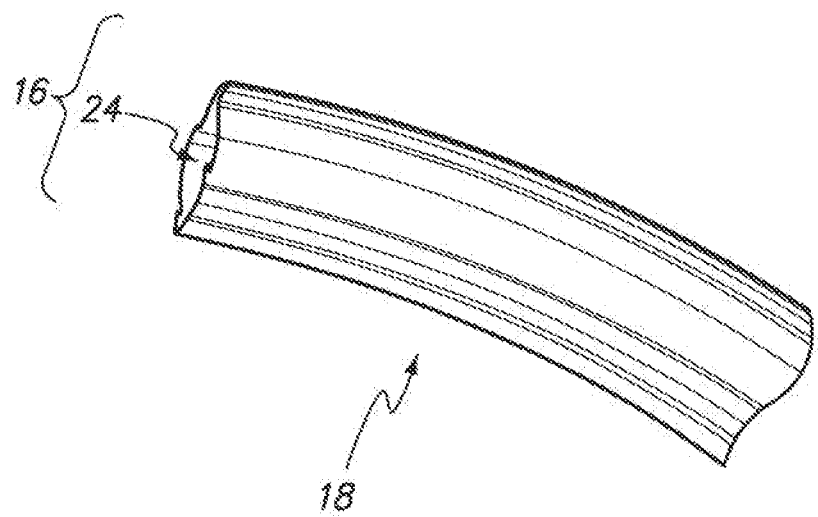
Figure 3D:
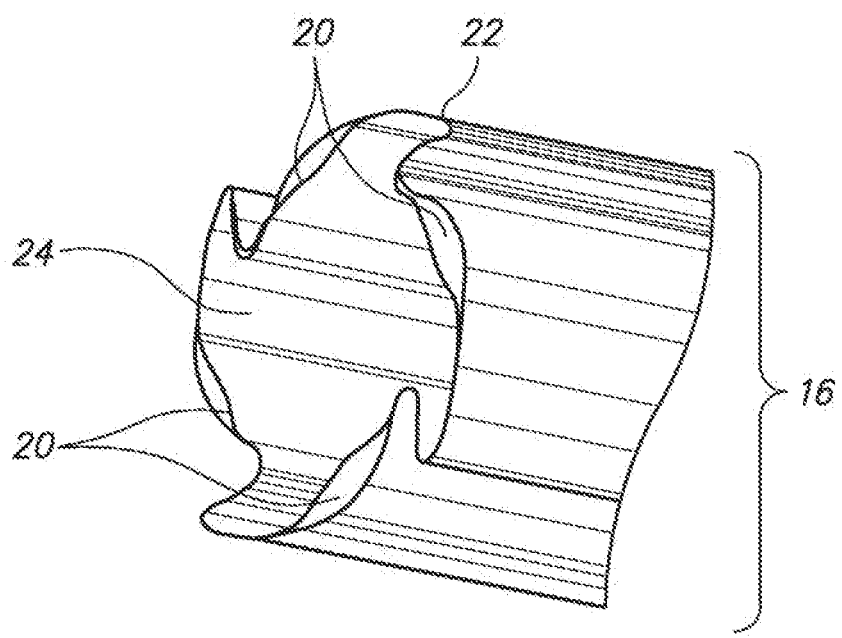
Figure 3E:
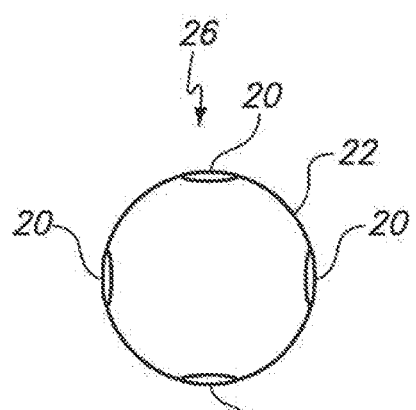
Figure 3F:
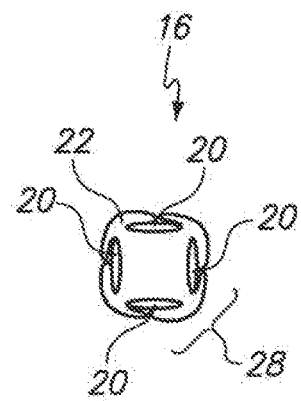
Figure 3G:
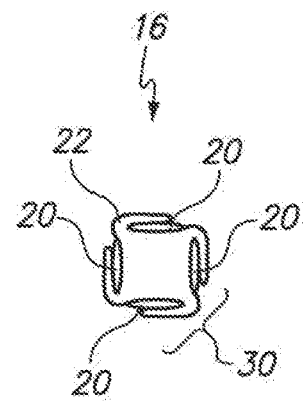
Figure 3H:
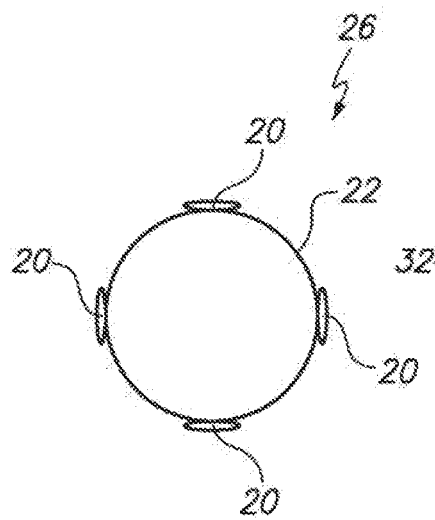
Figure 3I:
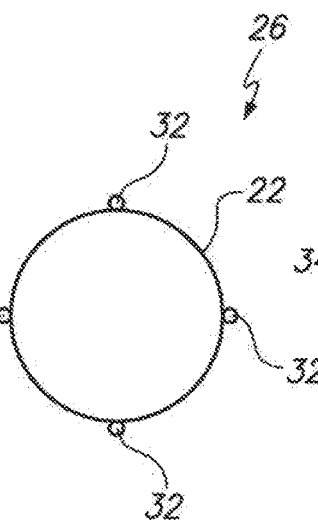
Figure 3J:
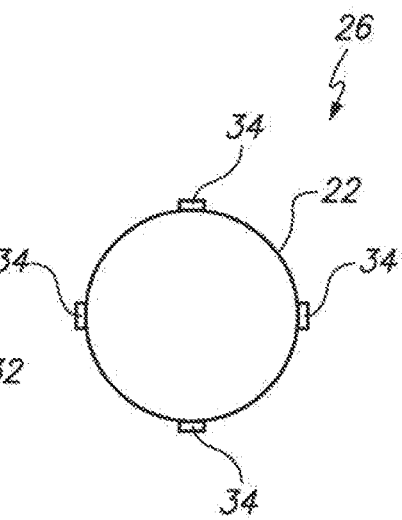
Figure 3K:
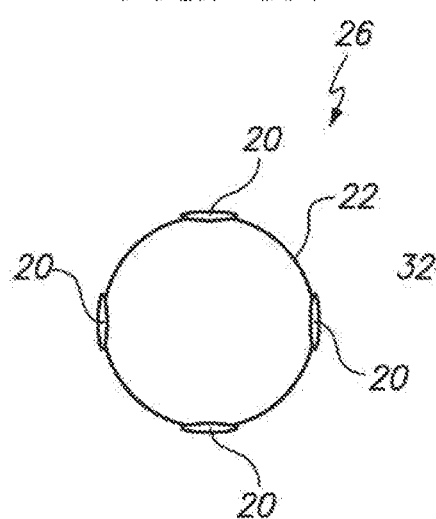
Figure 3L:
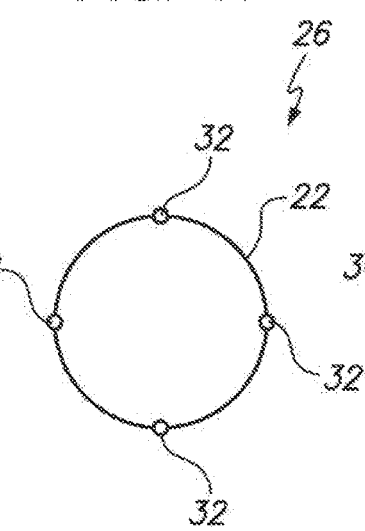
Figure 3M:
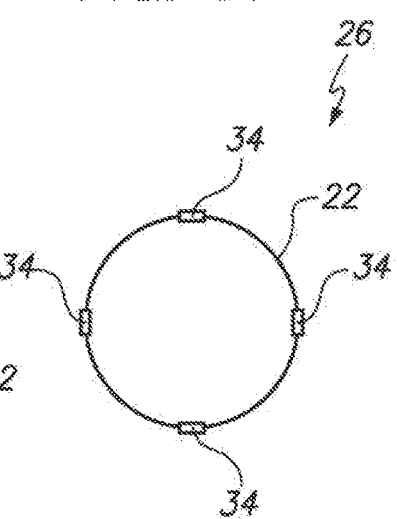
Figure 3N:
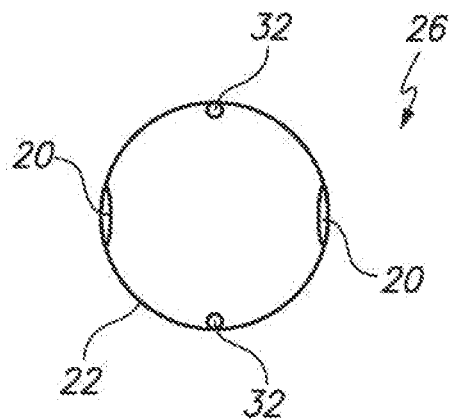
Figure 3O:
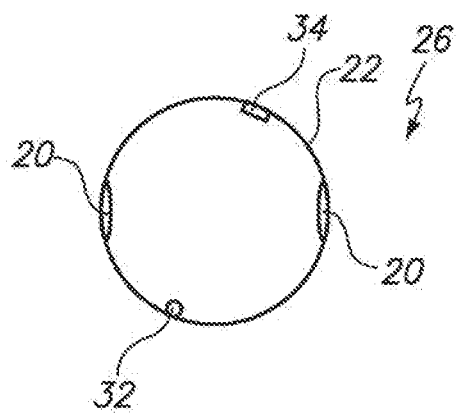
Figure 3P:
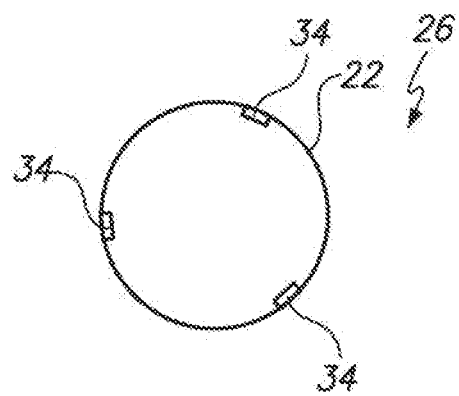
Figure 3Q:
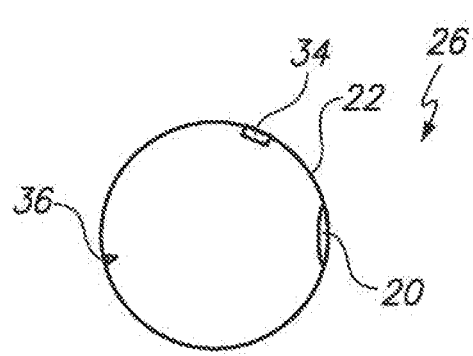
Figure 3R:
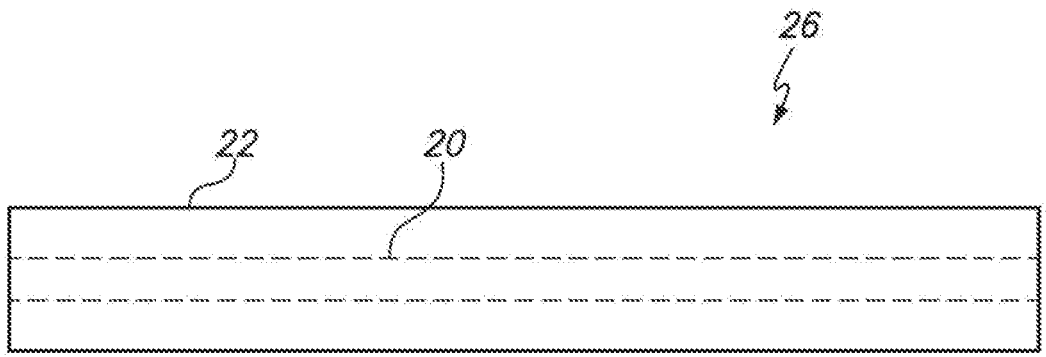
Figure 3S:
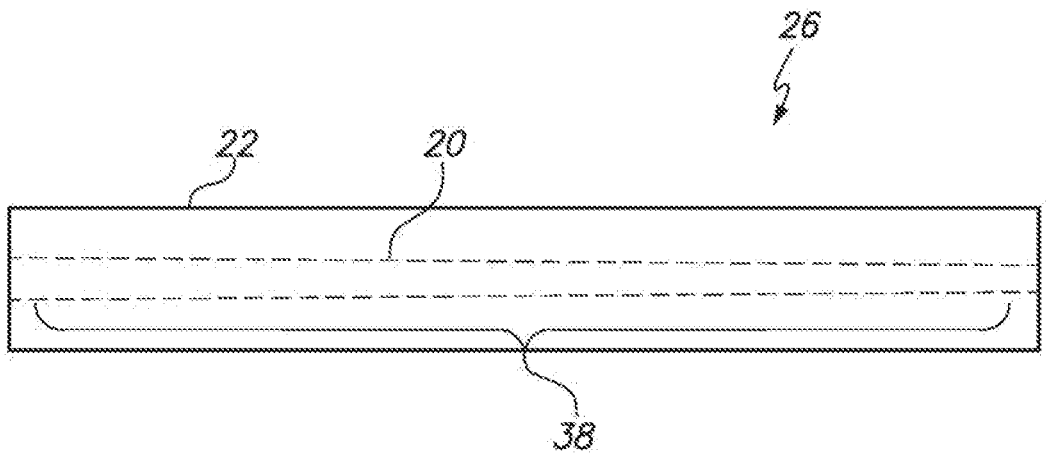
Figure 3T:
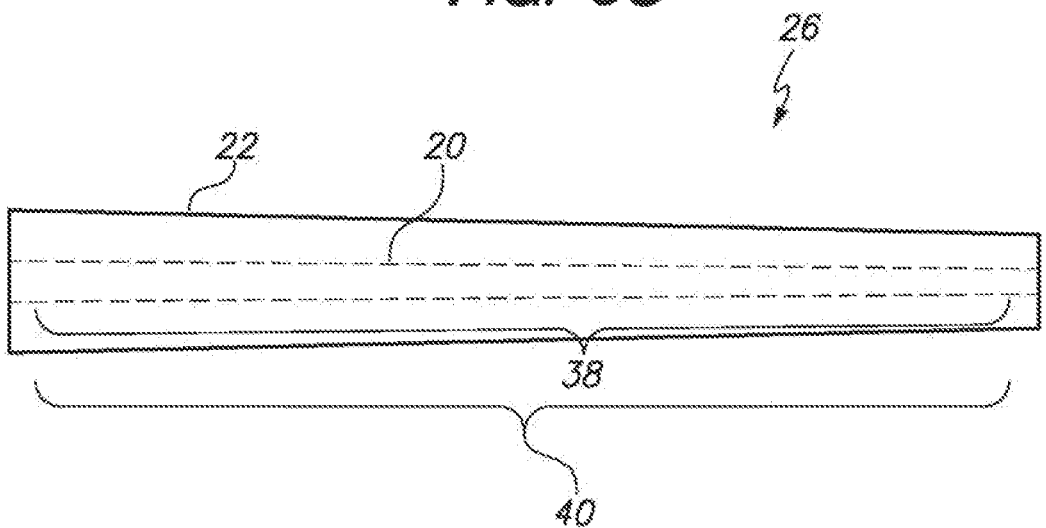
Figure 3U:
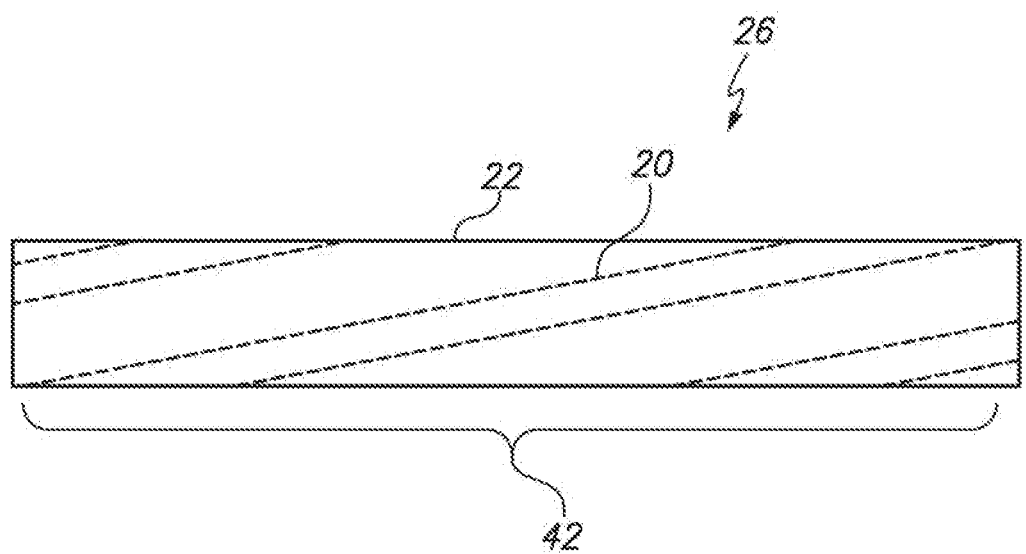
Figure 3V:
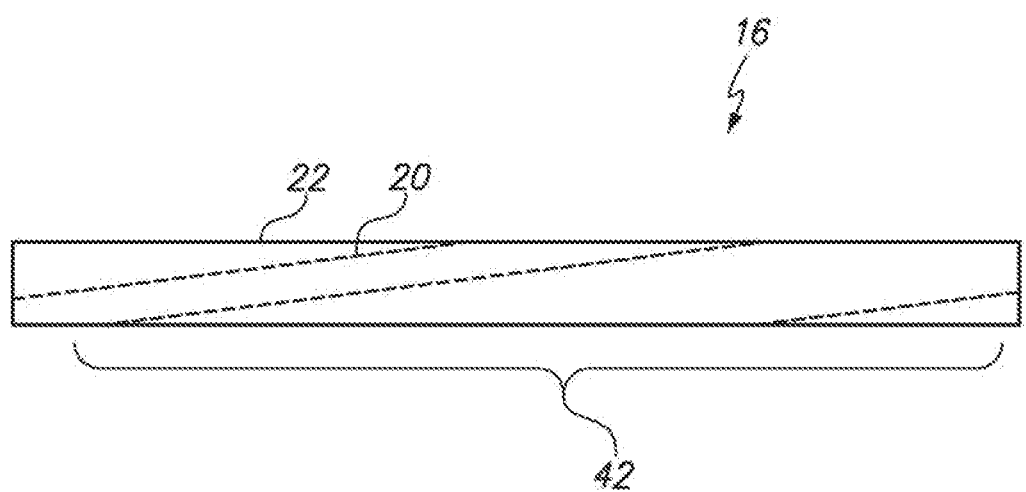
Figure 3W:
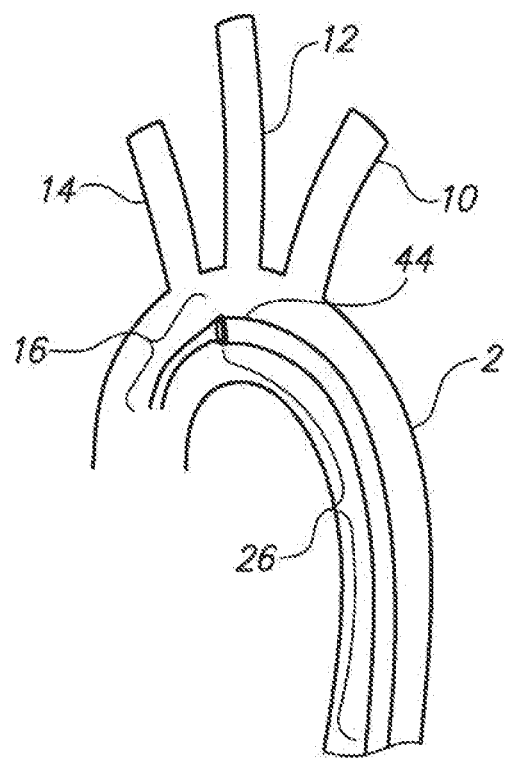
Figure 3X:
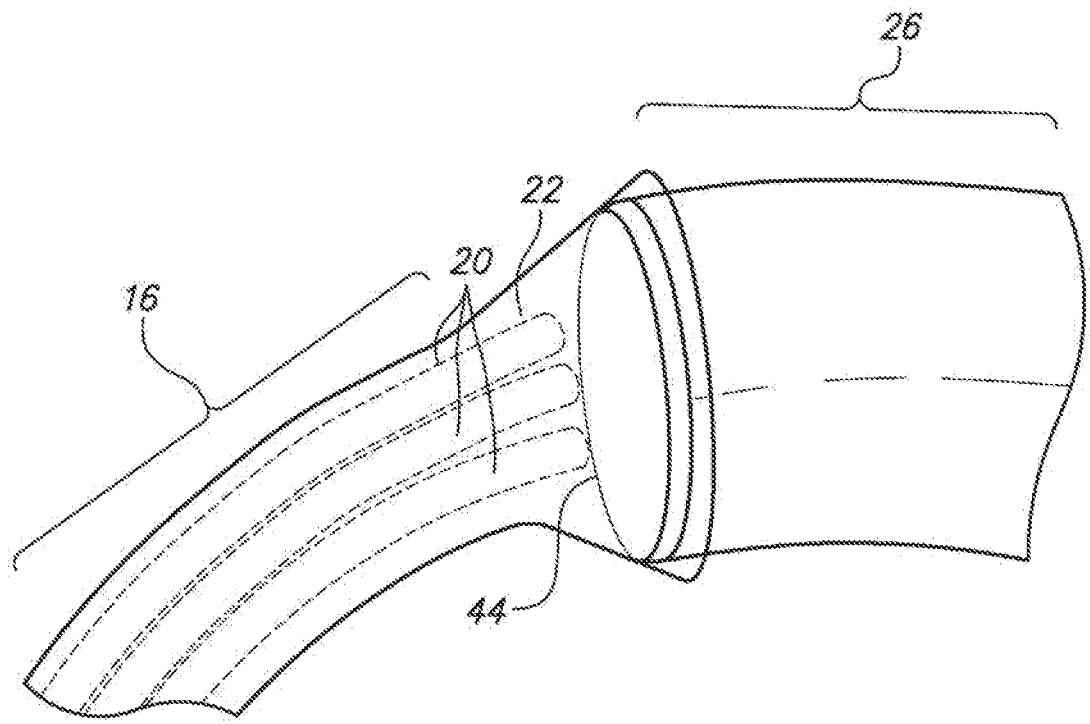
Figure 3Y:
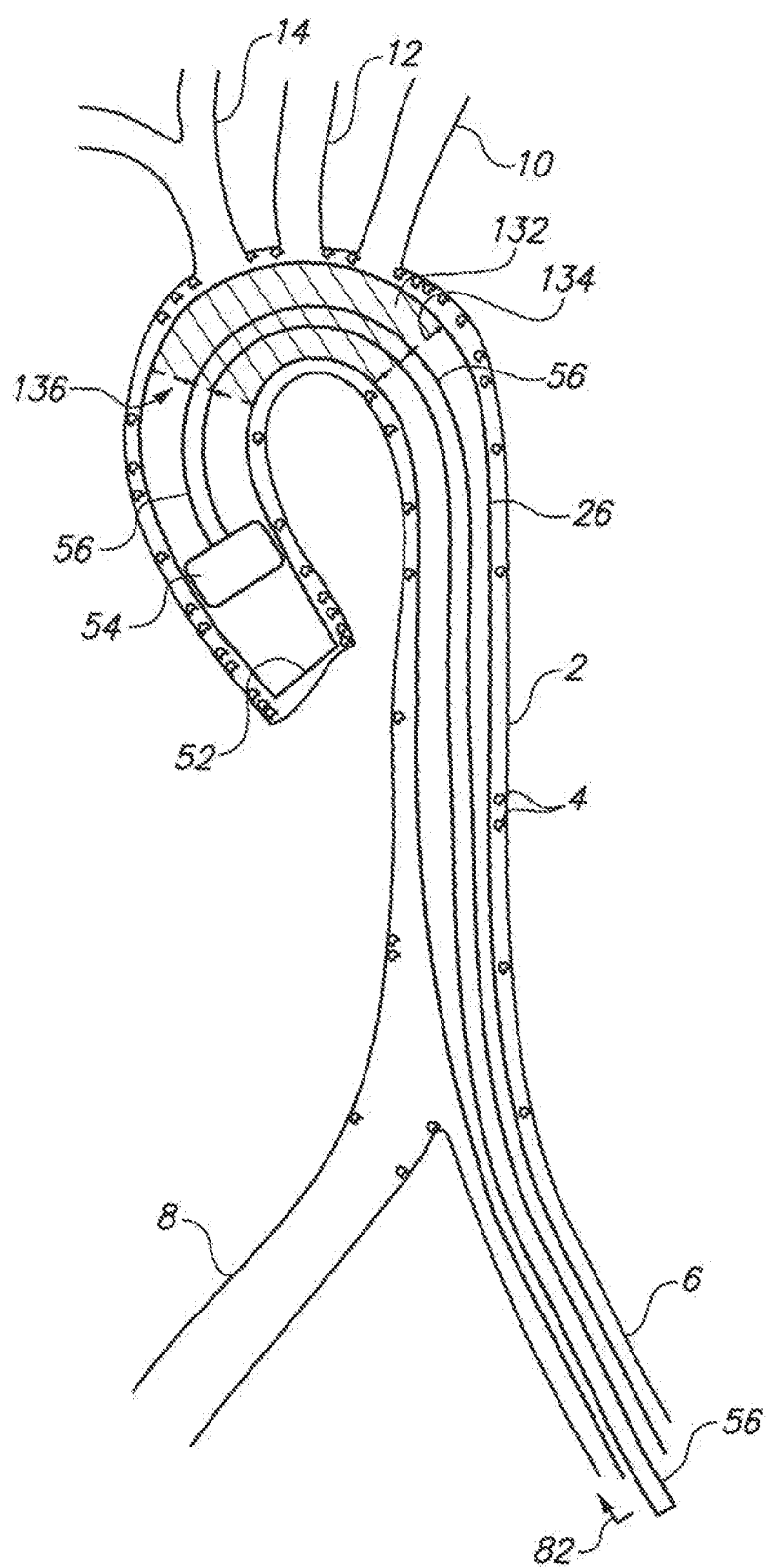
Figure 3Z:
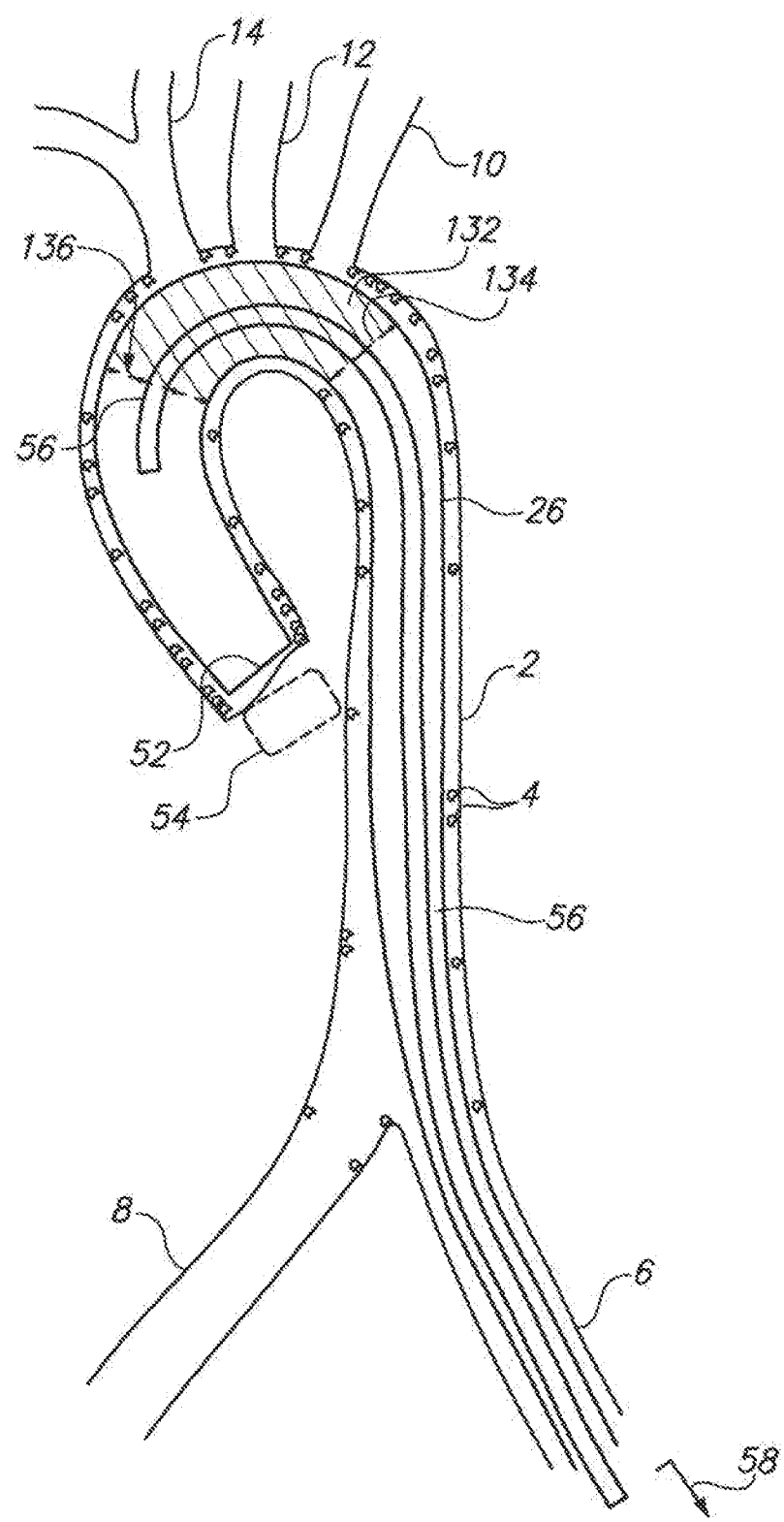
Figures 1, 3Z:
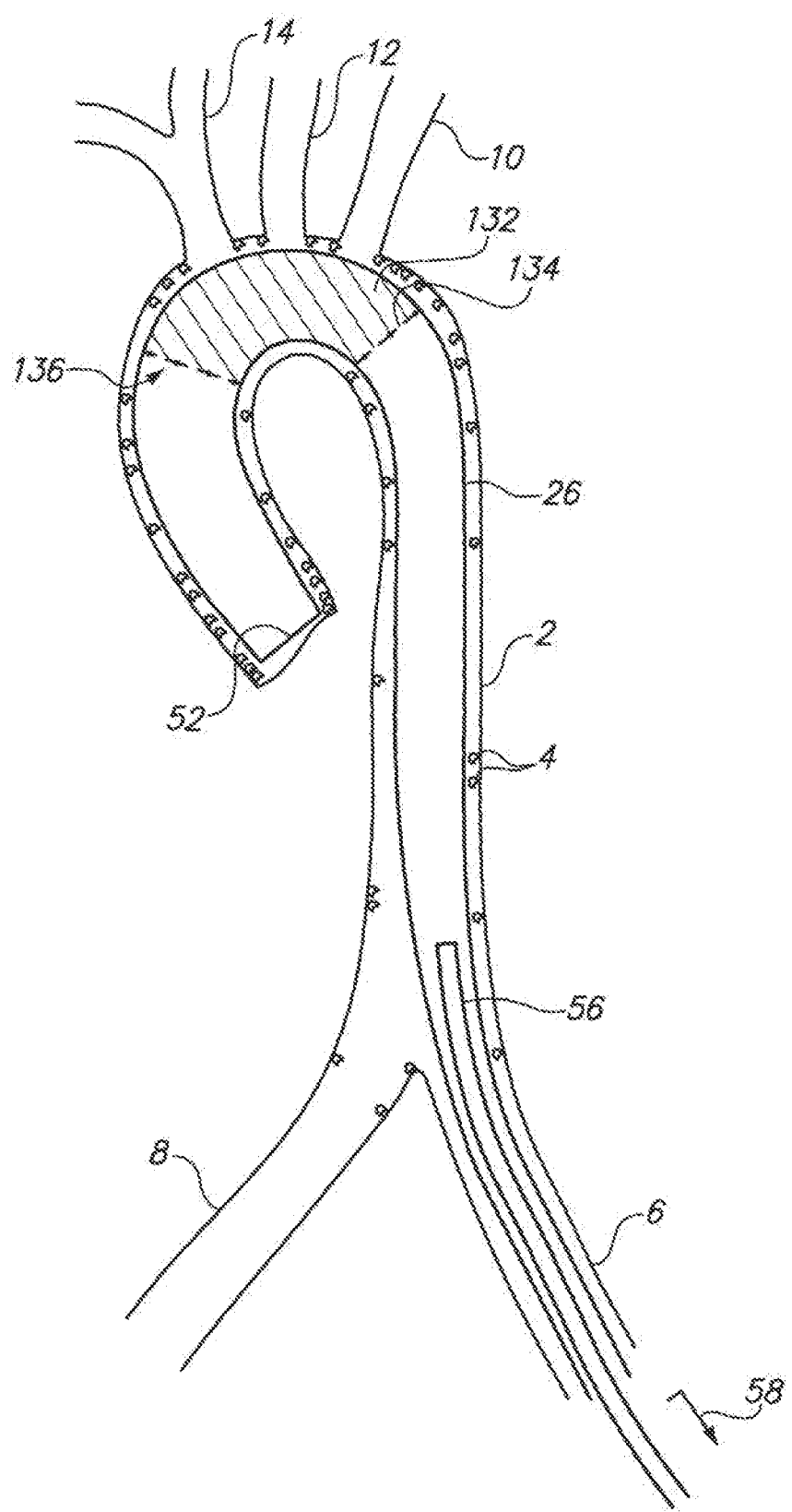
Figures 2, 3Z:
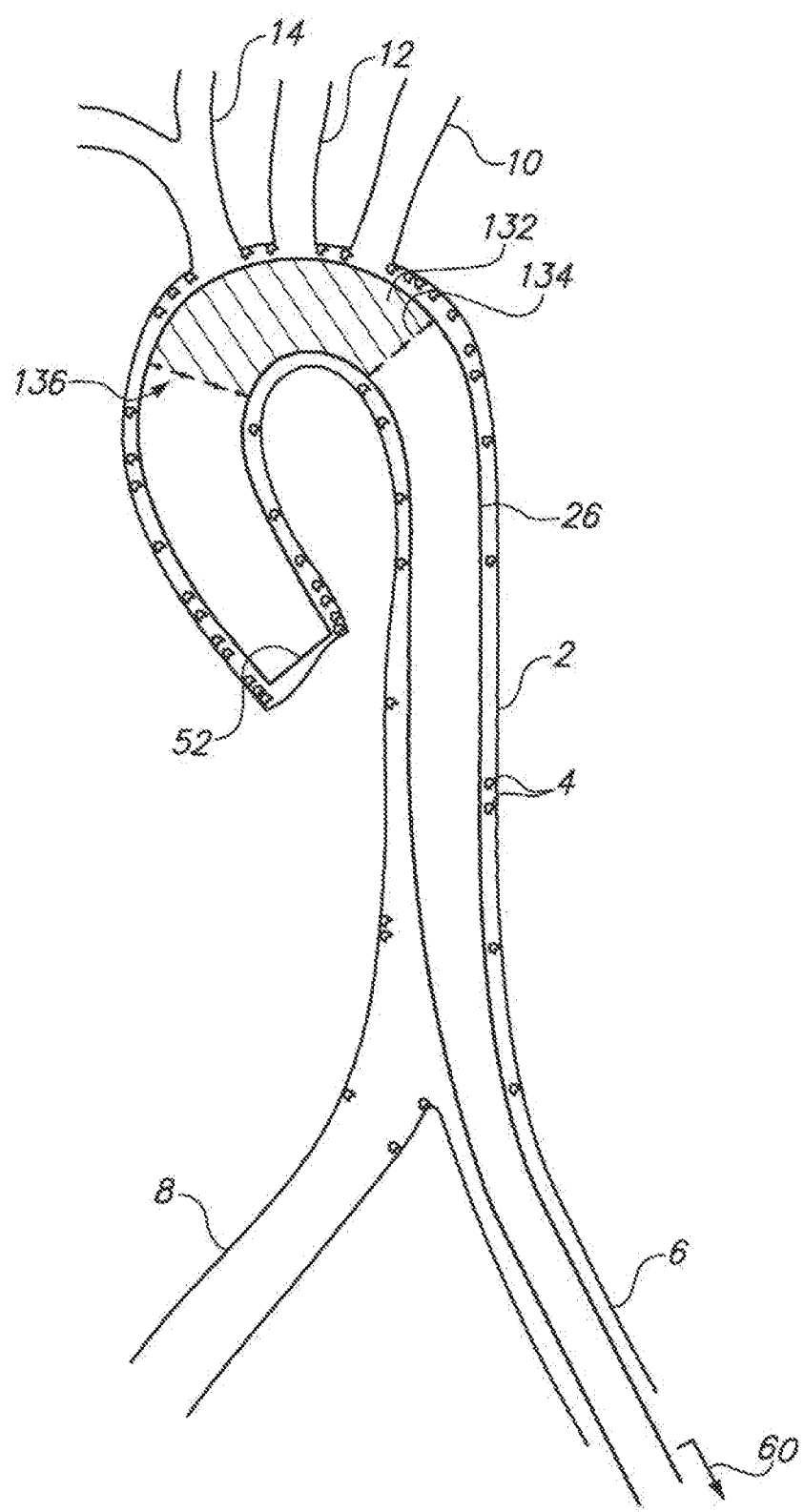
Figures 3, 3Z:
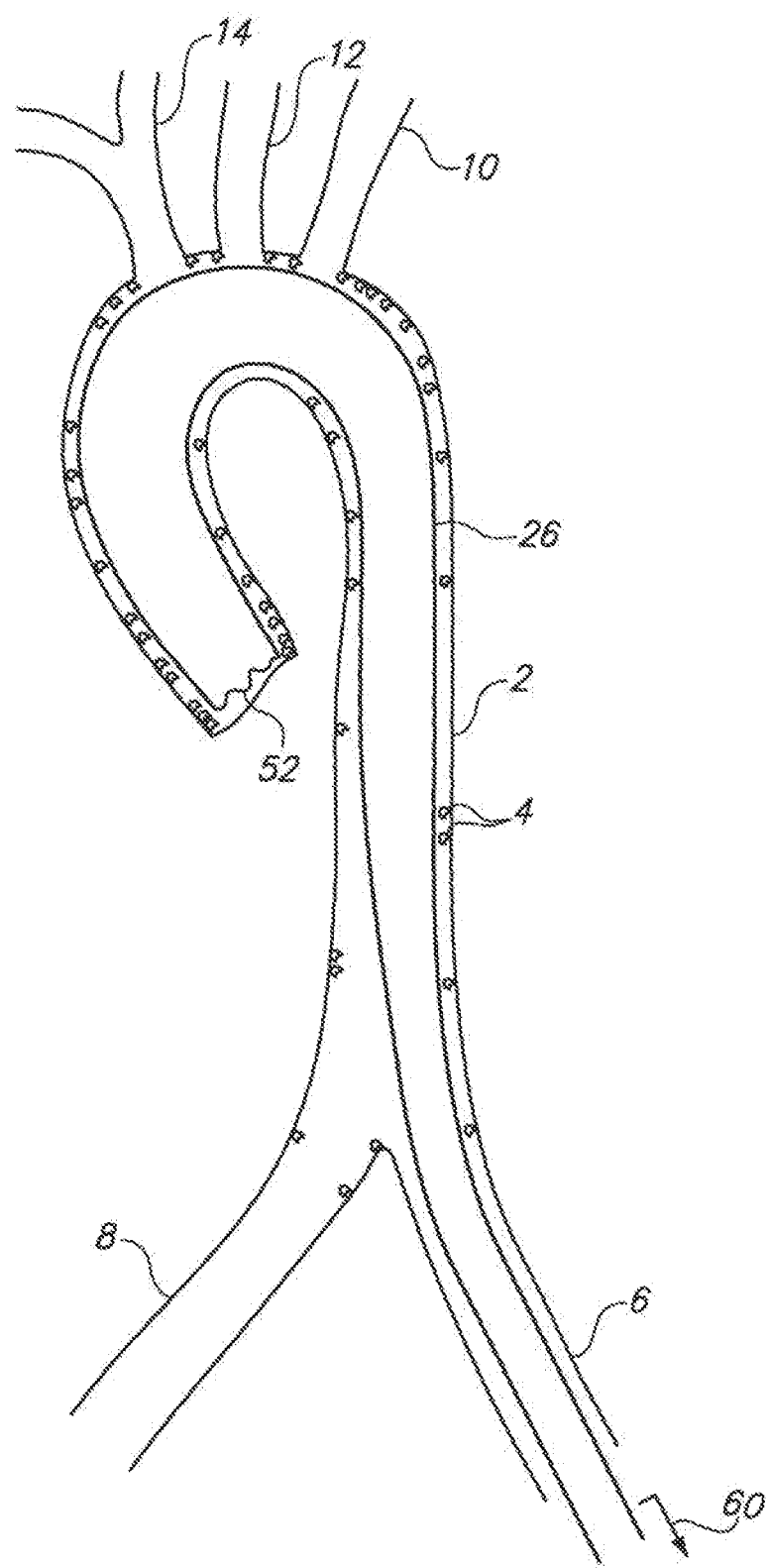
Figures 3, 3Z, 4:
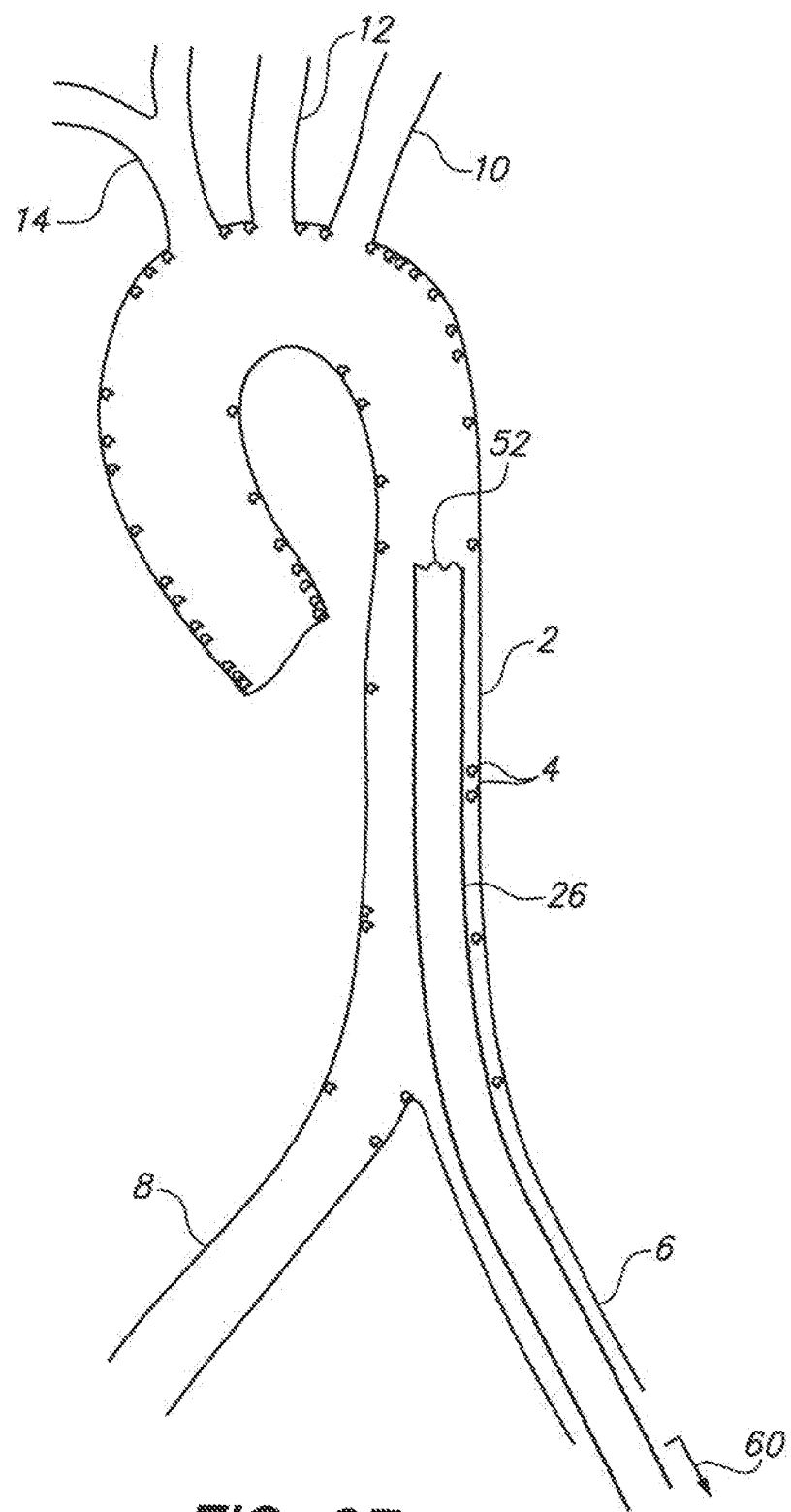

Referring to FIGS. 3A-3Z-4, various aspects of deployment steps and configurations utilizing embodiments of the inventive expandable railed sheath are illustrated. Referring to FIG. 3A, a collapsed configuration (16) of a railed sheath is being inserted (80) distal tip (52) first. This collapsed configuration (16) may be inserted over a guidewire using conventional "over-the-wire" technique to assist in guiding the collapsed sheath configuration. As compared with the insertion scenario of, for example, FIG. 2A, the collapsed configuration (16) leaves much more room in the diseased aorta (2), thereby decreasing the likelihood of a scraping type mechanical interface relationship as described in reference to FIGS. 2A-2F above. In one embodiment, the railed sheath may comprise one or more pullwires to facilitate steering by an operator as the collapsed railed sheath (16) is advanced through the diseased aorta (2) using imaging modalities such as transcutaneous ultrasound and/or fluoroscopy to assist with the interactive steering of such configuration through the diseased vessel. Referring to FIG. 3B, the distal tip (52) of the collapsed configuration (16) has reached the desired interventional location (here the aortic outflow tract of the left ventricle cavity of the heart) in a minimally invasive way taking advantage of the relatively small cross-sectional size of the collapsed configuration (16). Referring to FIGS. 3C and 3D, close up views of the collapsed configuration (16) are illustrated to show that the railed sheath indeed comprises a plurality of elongate rail structures (20; in the depicted embodiment 4 independent rail structures) coupled together by a sheet or sheet-like member (22) which, in the depicted collapsed configuration (16) is folded in between the elongate rail structures (20). A lumen (24) is defined through the railed sheath, and remains relatively small in diameter with the collapsed configuration (16).

Referring to FIGS. 3E-3Q, various configurations of railed sheath embodiments are illustrated in cross-sectional views. One key core functionality of each of the illustrative embodiments described herein is the notion of protecting surrounding vascular and other anatomy by providing an intermediate surface between relatively large items to be moved through the vasculature (i.e., such as elongate tools, collapsed prostheses, etc.) and the vasculature itself. The intermediate surface, or protective sheath, generally comprises a sheet-like member that is reinforced by a plurality of generally longitudinal rail members that are configured to de-concentrate loads applied from the inside of the sheath toward the nearby vascular anatomy—in a manner somewhat akin to the manner in which point loads from train wheels on a railroad track are de-concentrated by the rails of the railroad track and absorbed over a large surface provided by the substrate underlying the railroad track. This load de-concentration is believed to provide protection of the underlying anatomy from focused loads that could dislodge plaques or other particles, or create emboli—either from the focused load interface itself, or from any scraping or abrading interfacing that may be related to conventionally pushing a piece of hardware past the unprotected anatomy, as in FIGS. 2A-2F.

Referring to FIG. 3E, an expanded form (26) of a railed sheath embodiment is shown having four elongate rail members distributed approximately equidistantly about the circumference of the expanded form (26). The expanded form has an approximately circular outer shape and defines an approximately circular inner lumen. The elongate rail structures themselves have elliptical cross-sectional shape profiles (20) configured to atraumatically and easily accommodate sliding of another diagnostic or interventional device through the lumen during a medical procedure such as a percutaneous valve replacement. FIG. 3F illustrates one configuration of the same hardware as shown in FIG. 3E, but in the compressed or collapsed (16) format, with the sheet-like member (22) folded in both directions (i.e., partially folded onto each of the immediately adjacent rail structures 20). FIG. 3G illustrates another configuration wherein the sheet-like member (22) is folded in one direction (i.e., to find mechanical support for slack portions on the next adjacent rail structure 20 in one direction as shown). Either of the collapsed configurations illustrated in FIGS. 3F and 3G for example, may be suitable for deployment as in FIGS. 3A and 3B. Referring to FIGS. 3H-3M, various expanded configuration (26) embodiments are depicted to illustrate that a great variety of combinations and permutations of hardware subcomponentry is within the scope of the invention. Referring to FIG. 3H, four elliptical rail structures (20) are coupled to the outer aspect of a substantially tubular sheet-like member (22), for example, with polymer welding, adhesive, suturing, or other coupling configuration. The outer aspects of such configuration may be coated with a lubricious polymer to assist in the ease of sliding such a configuration past nearby tissue structures in a collapsed state; similarly, the inner aspects may be coated with a lubricious coating or surface to assist with slideable engagement between the expanded state of the railed sheath and instruments which may be passed through the working lumen during diagnostic and/or interventional procedure steps. Referring to FIG. 3I, in one embodiment, elongate rail structures of circular cross-section (32) may be utilized for a more uniform bending modulus configuration, and referring to FIG. 3J, elongate rail structures of rectangular or square cross-section (34) may be utilized to present preferred bending axes to the overall structure of the railed sheath. Referring to FIGS. 3K-3M, embodiments similar to those illustrated in FIGS. 3H-3J are depicted, with exception that the embodiments of FIGS. 3K-3M have the elongate rail structures (20, 32, 34, respectively) more tightly integrated into the outer and inner shape of the overall structure (i.e., the outer aspects of the rail structures don't protrude out as much). This may be accomplished, for example, by co-forming the rails (20, 32, 34, respectively) from the same bulk material as the sheet-like members (22), or at least partially encapsulating the rails (20, 32, 34, respectively) with the sheet-like member (22) material. Referring back to the embodiment of FIG. 3E, various embodiments may be created to have a substantially smooth outer shape in the expanded state, and to have the elongate rail structures (20) protrude more into the inner lumen of the overall structure, which may be desired for mechanically guiding various portions of the diagnostic and/or interventional hardware that may be passed through the working lumen for the medical procedure.

Referring to FIGS. 3N-3Q, various configurations are shown to illustrate that cross-sectional homogeneity is not only not necessary, but may not be preferred in some scenarios. Referring to FIG. 3N, one expanded configuration (26) is shown wherein a sheet-like member (22) couples two elliptical rail structures (20) and two circular rail structures (32). Referring to FIG. 3O, a less cross-sectionally homogeneous configuration is shown having two elliptical rail structures (20) coupled to the sheet-like member (22) diametrically across from each other, and a circular rail structure (32) diametrically opposed from a rectangular (34) rail structure at an angle so that the four depicted rail structures are not uniformly distributed about the circumference of the depicted cross-section. Referring to FIG. 3P, three rectangular rail structures (34) are equidistantly circumferentially distributed about the cross-section. Referring to FIG. 3Q, a group of triangular (36), elliptical (20), and rectangular (34) rail structures is not equidistantly circumferentially distributed about the cross-section. The various cross-sectional permutations and combinations may be selected to improve deliverability, to have selected overall shape bending moduli, and to improve utility of the working lumen for passing through diagnostic and/or interventional tools during a medical procedure.

Further, the mechanical performance of the collapsible railed sheath may be customized and modified by changing the shapes, materials, and positions/orientations of various portions longitudinally (i.e., relative to the length of the overall catheter structure). Several such configurations are illustrated in FIGS. 3R-3V. Referring to FIG. 3R, a longitudinally uniform configuration has the same cross-sectional configuration of rail structures (20) and sheet-like member (22) all along its length. Referring to FIG. 3S, an embodiment is shown wherein the outer shape of the overall structure does not change longitudinally, but wherein one or more of the rail structures (20) are tapered in shape (38) longitudinally, to provide greater overall bending modulus for the catheter at the end with the more tapered rail structures. Referring to FIG. 3T, an embodiment is depicted which has not only one or more tapered (38) rail structures (20), but also a tapered (40) overall outer shape. Such a configuration would have inner lumen size limitations, but would provide greater overall bending modulus for the catheter at the end with the more tapered rail structures and overall shape. Referring to FIGS. 3U and 3V, the rail structures may be angularly oriented relative to the longitudinal axis of the overall shape. As shown in the expanded configuration (26) of FIG. 3U, one or more of the rail structures (20) have a spiral orientation (42). FIG. 3V shows that the same embodiment as shown in FIG. 3U may be collapsed into a collapsed configuration (16), with the spiral orientation (42) of the one or more rail structures retained, but to a lesser spiraling angle relative to the longitudinal axis of the overall shape.

Referring to FIGS. 3W and 3X, the transition between collapsed configuration (16) and expanded configuration (26) may be accomplished by advancing a diagnostic and/or interventional instrument (44) through the lumen of the railed sheath. As shown in FIG. 3W, the proximal portion of the railed sheath through which the instrument (44) has been advanced are in the expanded configuration (26), while the distal portion which has not yet been reached by the instrument (44) remains in the collapsed configuration (16). In one embodiment, the rails are specifically configured to assist in maintaining the orientation of the instrument (44) relative to the railed sheath and associated tubular anatomy as the instrument (44) is advanced through the railed sheath, to ensure that a predictable orientation is maintained when the instrument (44) reaches the desired diagnostic and/or interventional tissue theater. For example, in the case of a percutaneous valve replacement procedure, it is highly desirable to make sure that the valve prosthesis gets to the desired location, such as in the aortic outflow tract, in a predictable orientation relative to the structural tissue of the outflow tract, but also that damage is not caused to the patient during the deployment; the subject configurations are designed with such priorities in mind. In another embodiment, as described in further detail below, the railed sheath may be a self-expanding sheath that is affirmatively retained in a collapsed configuration (16) until a desired time upon which it may be controllably converted to the expanded configuration (26). A corset-style collapse-retention member with a releasable (i.e., by proximal tension) tensile member may be utilized to retain the collapsed configuration, as in international PCT Publication No. WO 97/21403, which is incorporated by reference herein in its entirety.

Figure 17A:
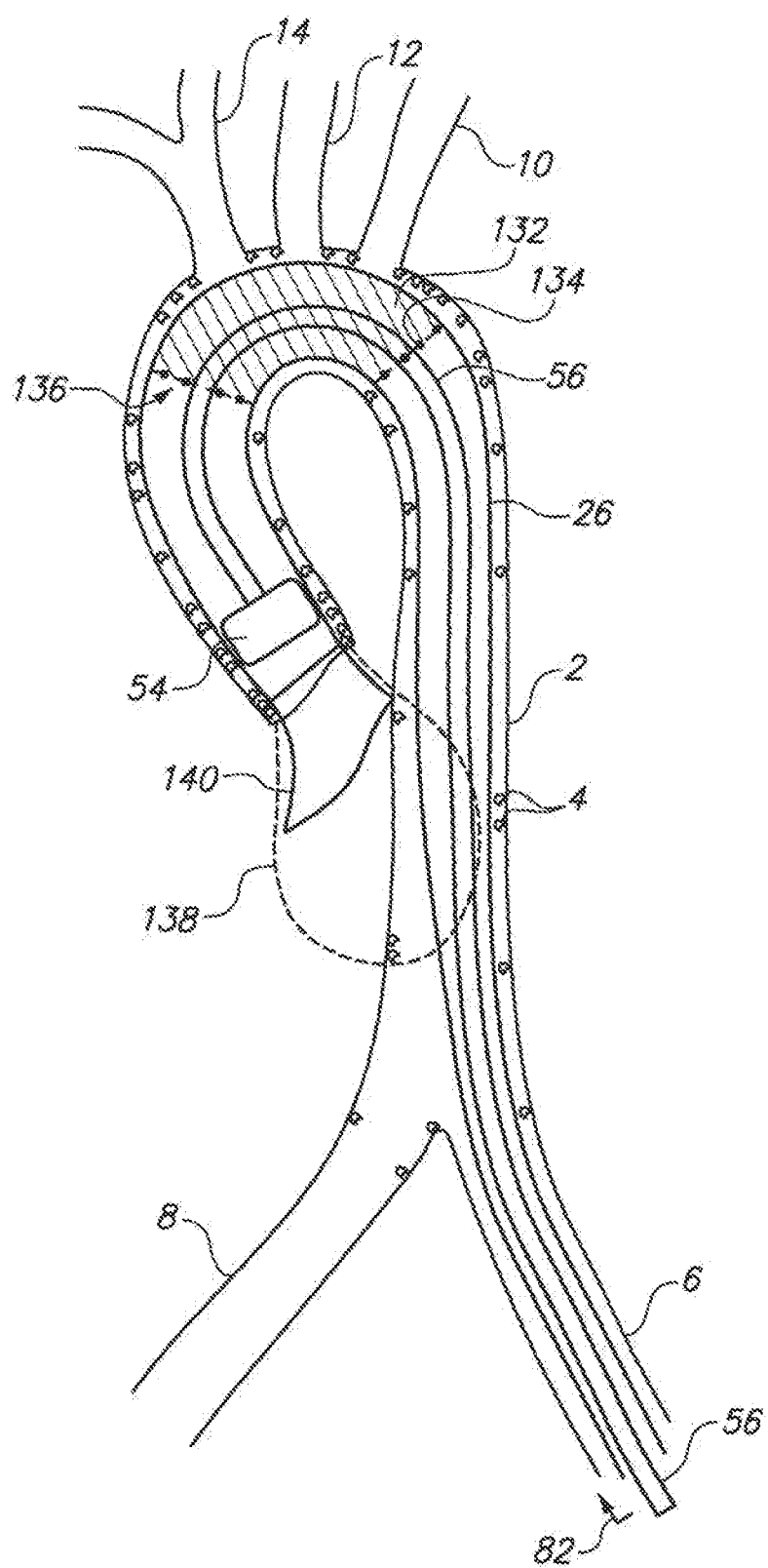
FIGS. 17A-17C illustrate aspects of an embodiment of a railed sheath having a frustoconical distal portion configured to interface with a cardiovascular cavity.
Figure 17B:
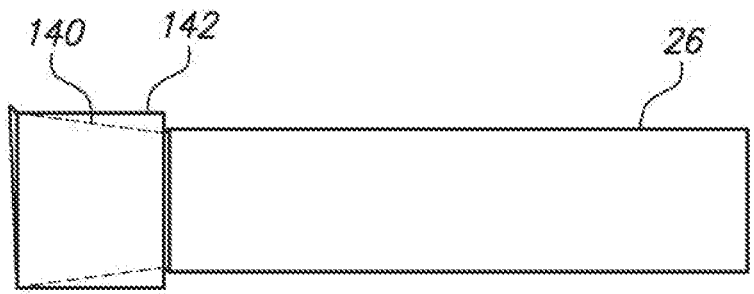
Figure 17C:
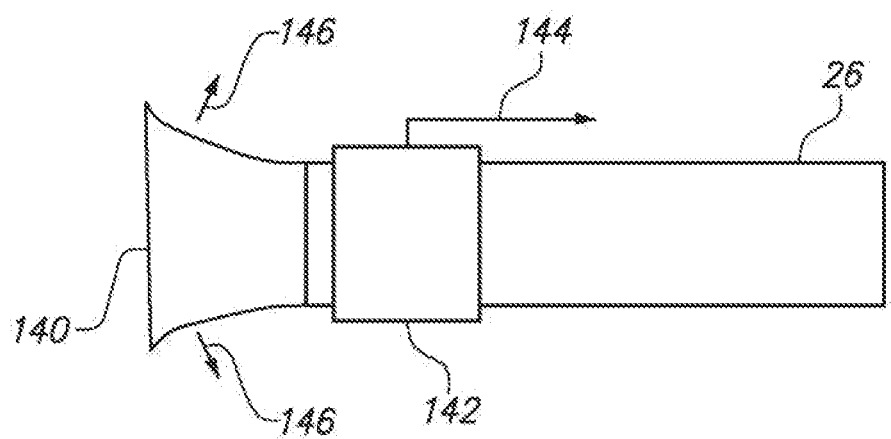

Referring to FIG. 3Y, in one embodiment, an expanded configuration of a railed sheath (26) may comprise one or more porous regions (132) configured to be positioned adjacent tributary vessels to maintain flow through such vessels when the expanded railed sheath is in place. As shown in FIG. 3Y, a porous region (132) is configured in this embodiment to ensure that flow coming into the distal tip (52) of the expanded railed sheath (26) is at least partially diverted up the associated tributary vessels (10, 12, 14) to supply the brain of the patient with blood during the procedure. The margins of the porous region may be marked with radiopaque markers to facilitate confirmation of placement of the porous region in a desired configuration relative to the anatomy, and transcutaneous and/or intravascular ultrasound and/or fluoroscopy with contrast agent may be utilized to confirm flow out of the aorta and into important tributary vessels during placement of the railed sheath. Preferably the porous region functions not only as a flow bypass, but also as a filter to capture any deposits or emboli that are being routed through the railed sheath; this may be accomplished by sizing the pores of the porous region to be large enough to pass blood plasma and red blood cells, but small enough to not pass typical emboli and deposits. Referring ahead to FIGS. 17A-17C, an embodiment similar to that of FIG. 3Y is depicted, but in this case the distal end of the railed sheath comprises a trumpet or frustoconical shape (140) configured to maximize the likelihood that emboli or deposits that exit the adjacent anatomy (here the aortic outflow tract of the left ventricle cavity of the heart 138) by providing a more contoured fit of the adjacent anatomy. Referring to FIG. 17B, during deployment, the flared distal frustoconical portion (140) may be retained in a compressed form by a movable or slideable cuff member (142), which, as shown in FIG. 17C, may be retracted (144) proximally to allow the flared distal frustoconical portion (140) to be expandable or expanded (146) into the adjacent anatomy.

In both FIGS. 17A and 3Y, an elongate insertion device (56) is shown inserting a diagnostic and/or interventional device (54), such as a collapsed aortic valve prosthesis, toward the desired anatomical location using the subject railed sheath. Referring to FIGS. 3Z and 3-Z1 with the device (56) safely deployed into the subject anatomy, the elongate insertion device (56) may be safely retracted (58) back out through the expanded configuration (26) of the railed sheath. Referring to FIG. 3-Z2, with the diagnostic and/or interventional procedure substantially completed, the railed sheath may be removed by pulling proximally (60) on the sheath and retracting it out, as shown in FIGS. 3-Z3 and 3-Z4. In another embodiment, as described in further detail below, the sheath may be forcibly converted from expanded configuration (26) to collapsed configuration (16) for removal, using, for example, an electromagnetic collapsing device. With all of the instrumentation removed, the access wound (for example, to one of the femoral arteries) may be closed and the procedure completed.

Figure 4A:
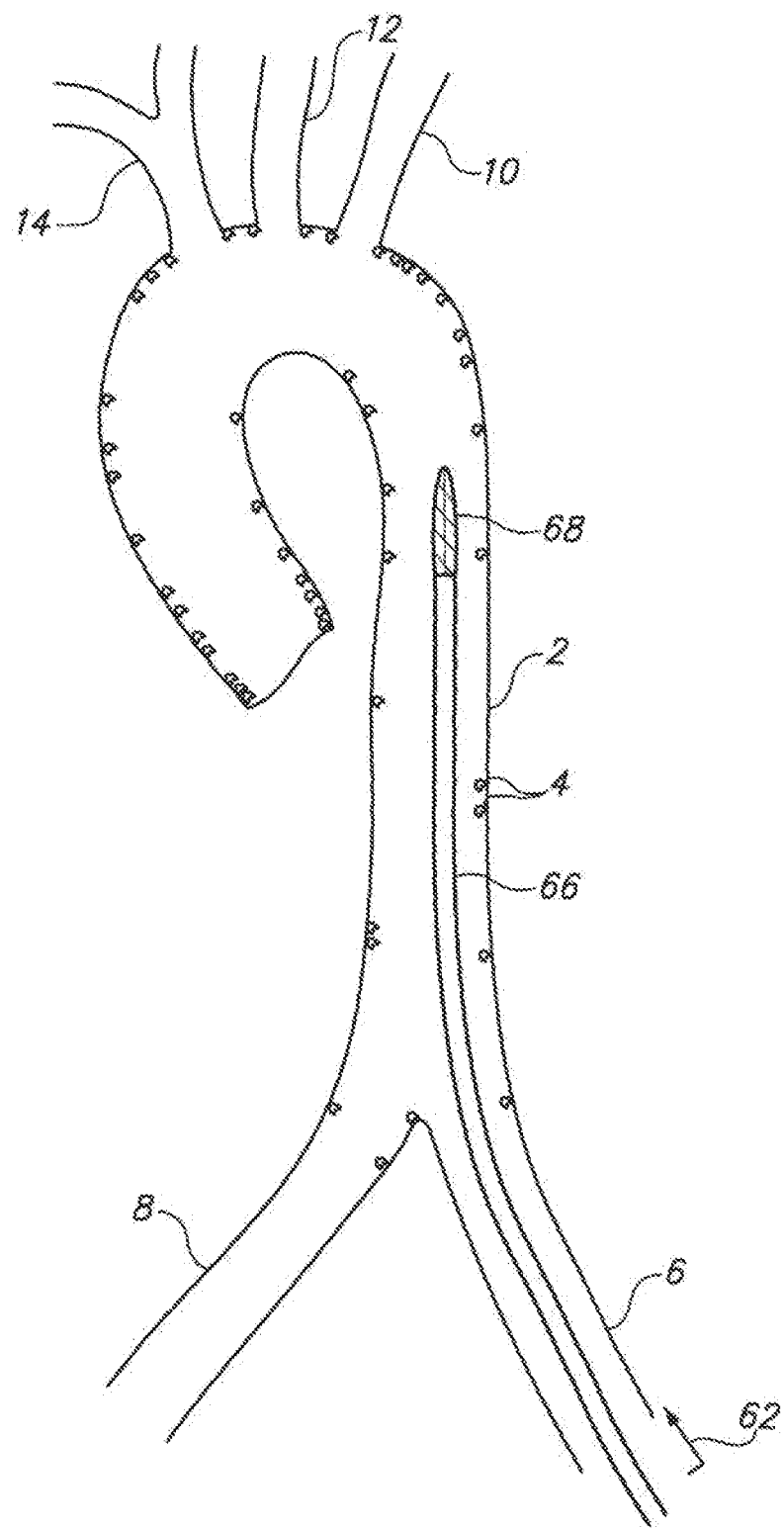
FIGS. 4A-4H illustrate aspects of a configuration similar to that of FIGS. 3A-3Z-4, wherein a branch vessel protection filter is also incorporated.
Figure 4B:
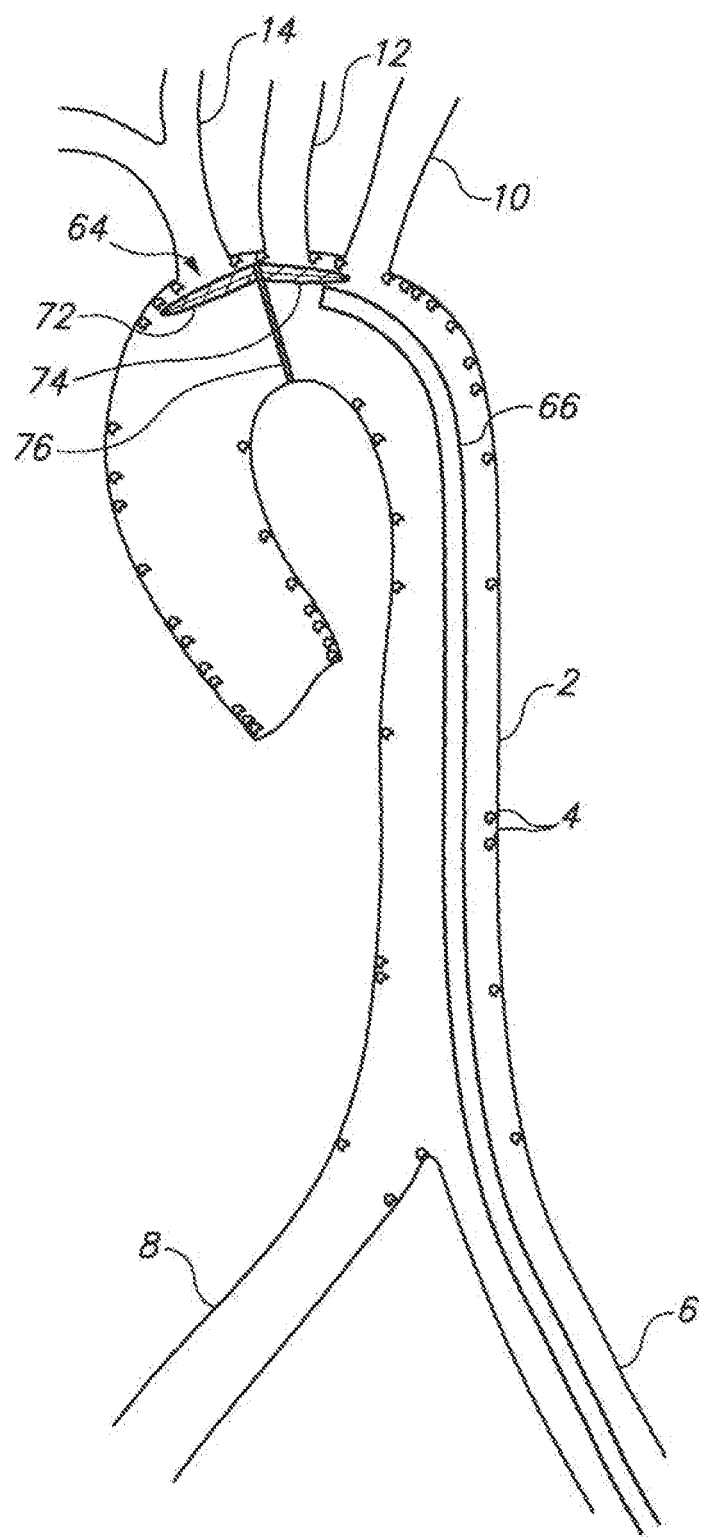
Figure 4C:
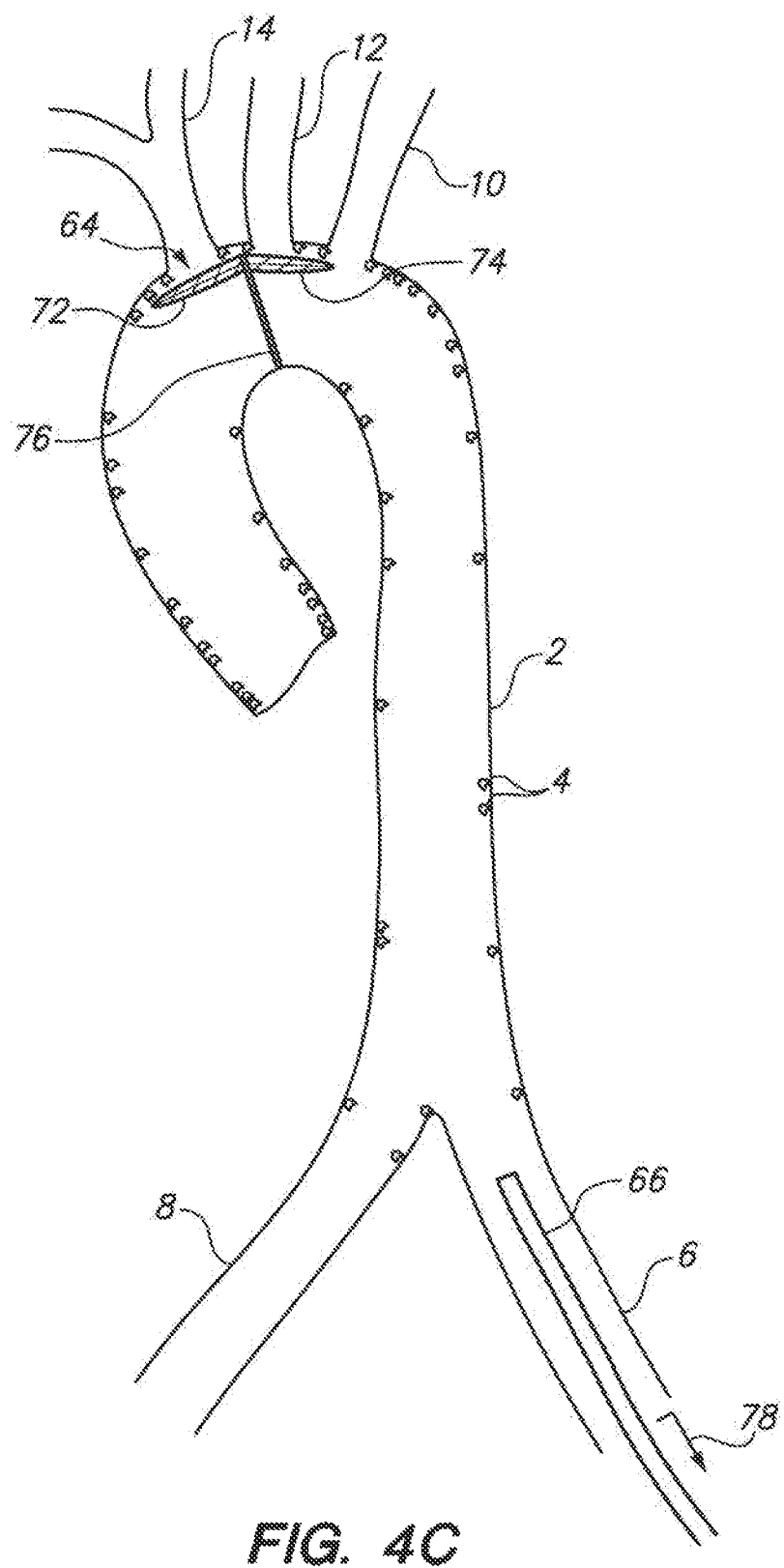
Figure 4D:
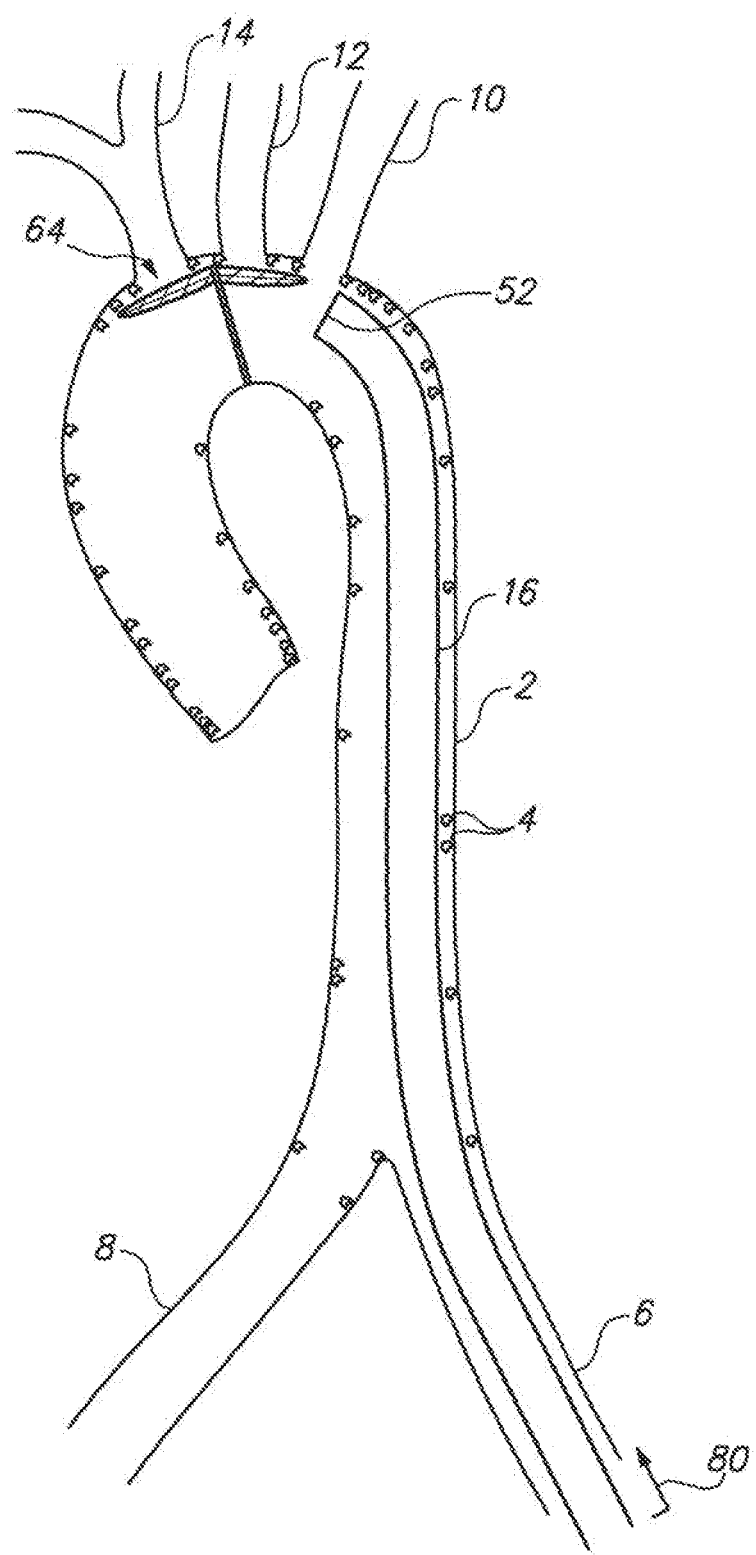
Figure 4E:
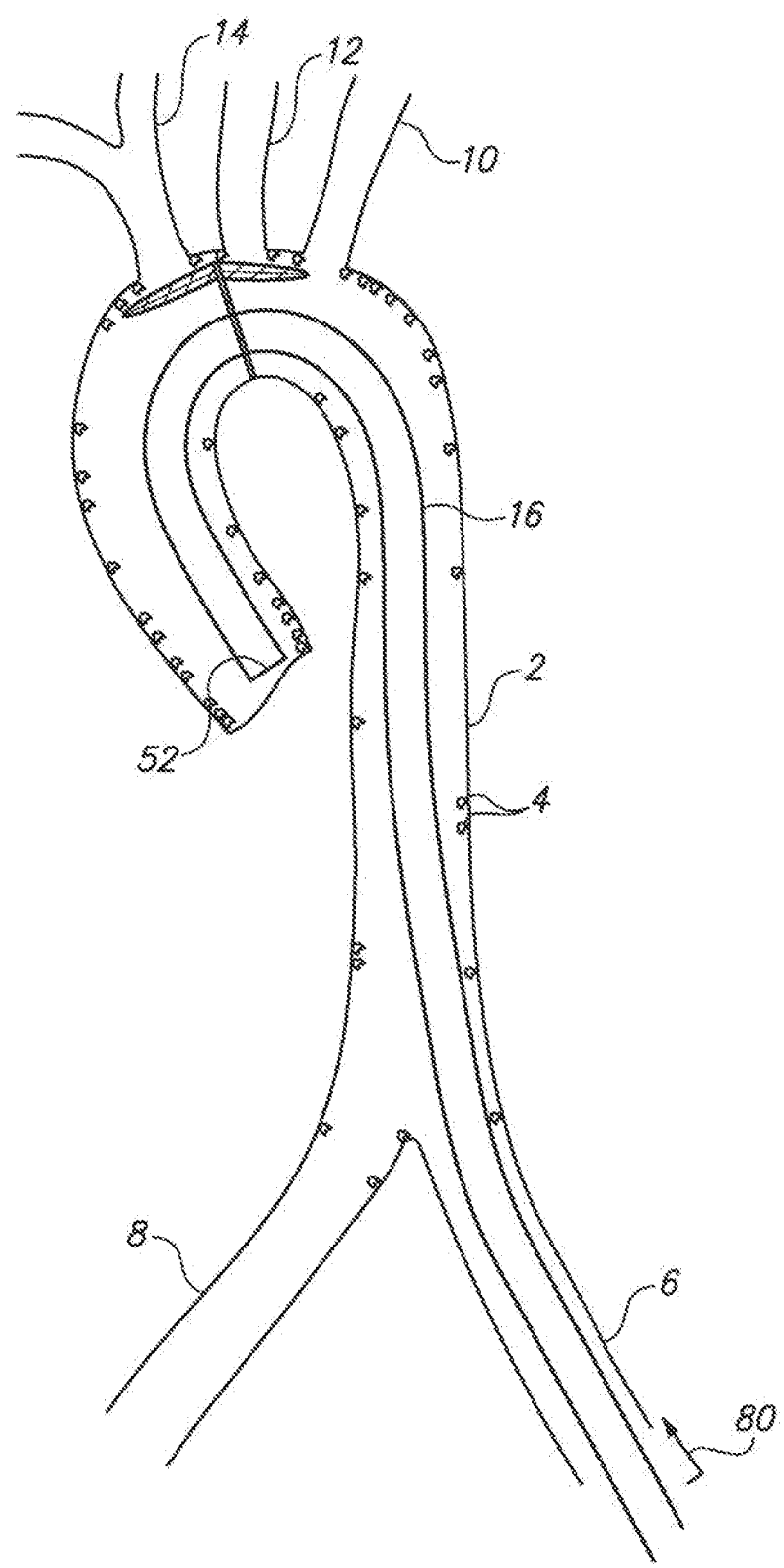
Figure 4F:
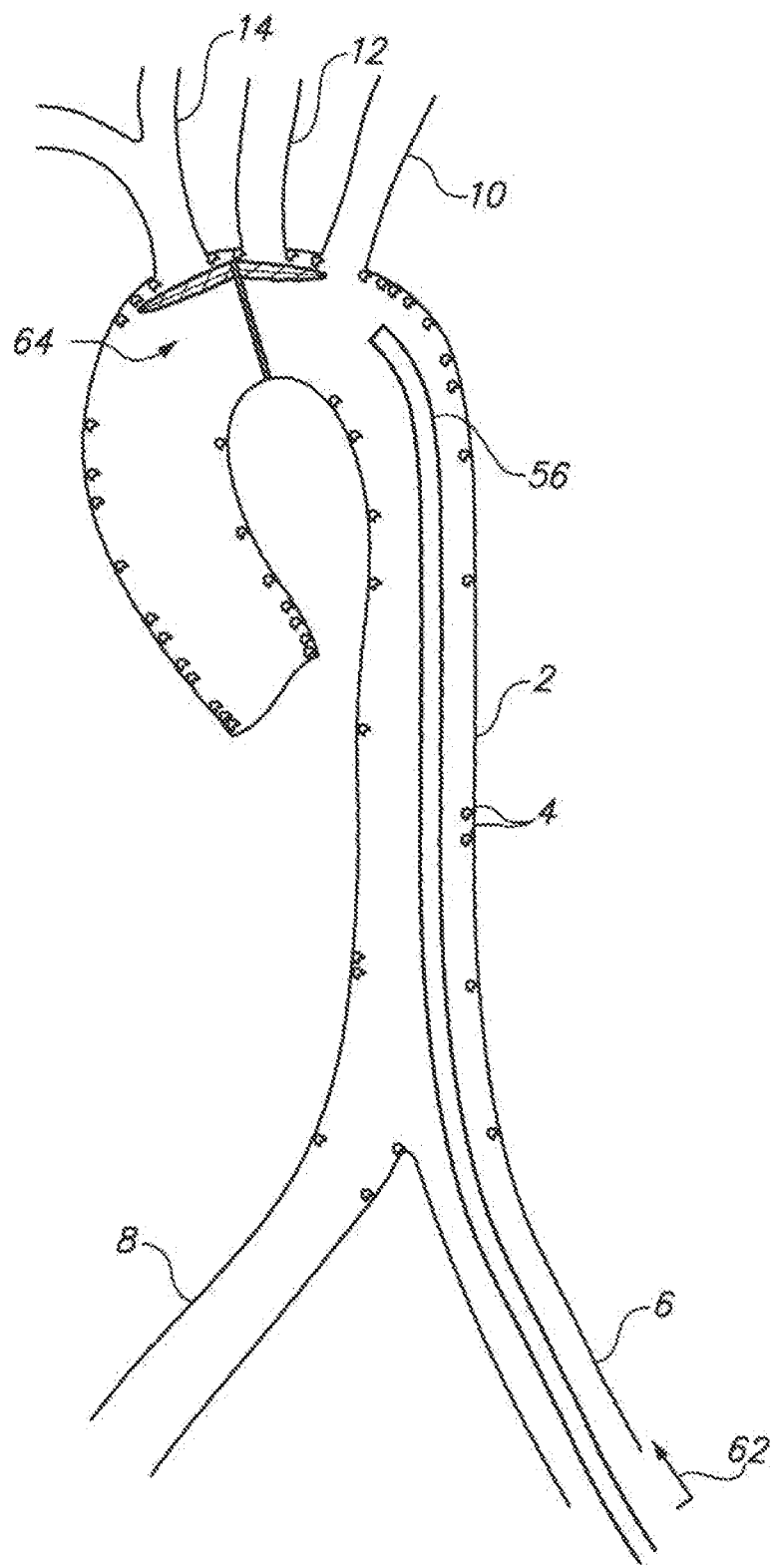
Figure 4G:
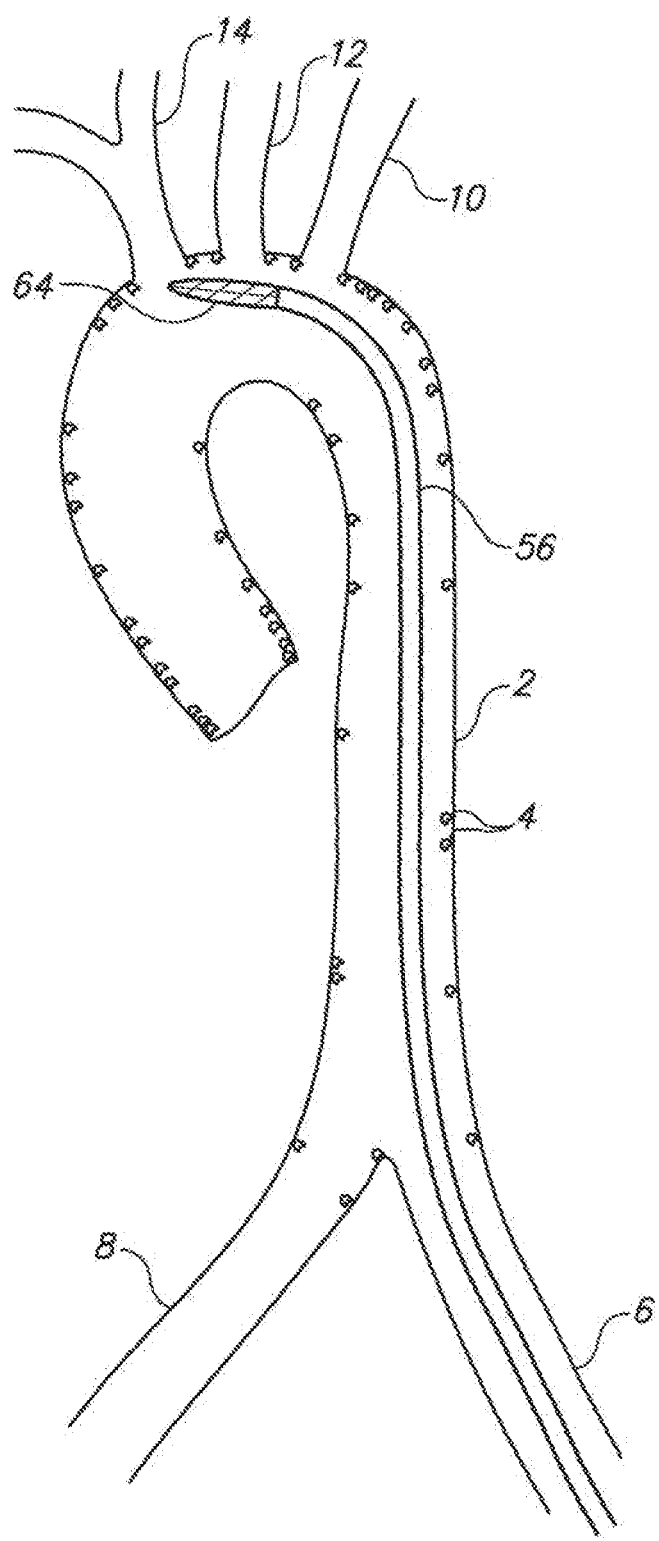
Figure 4H:
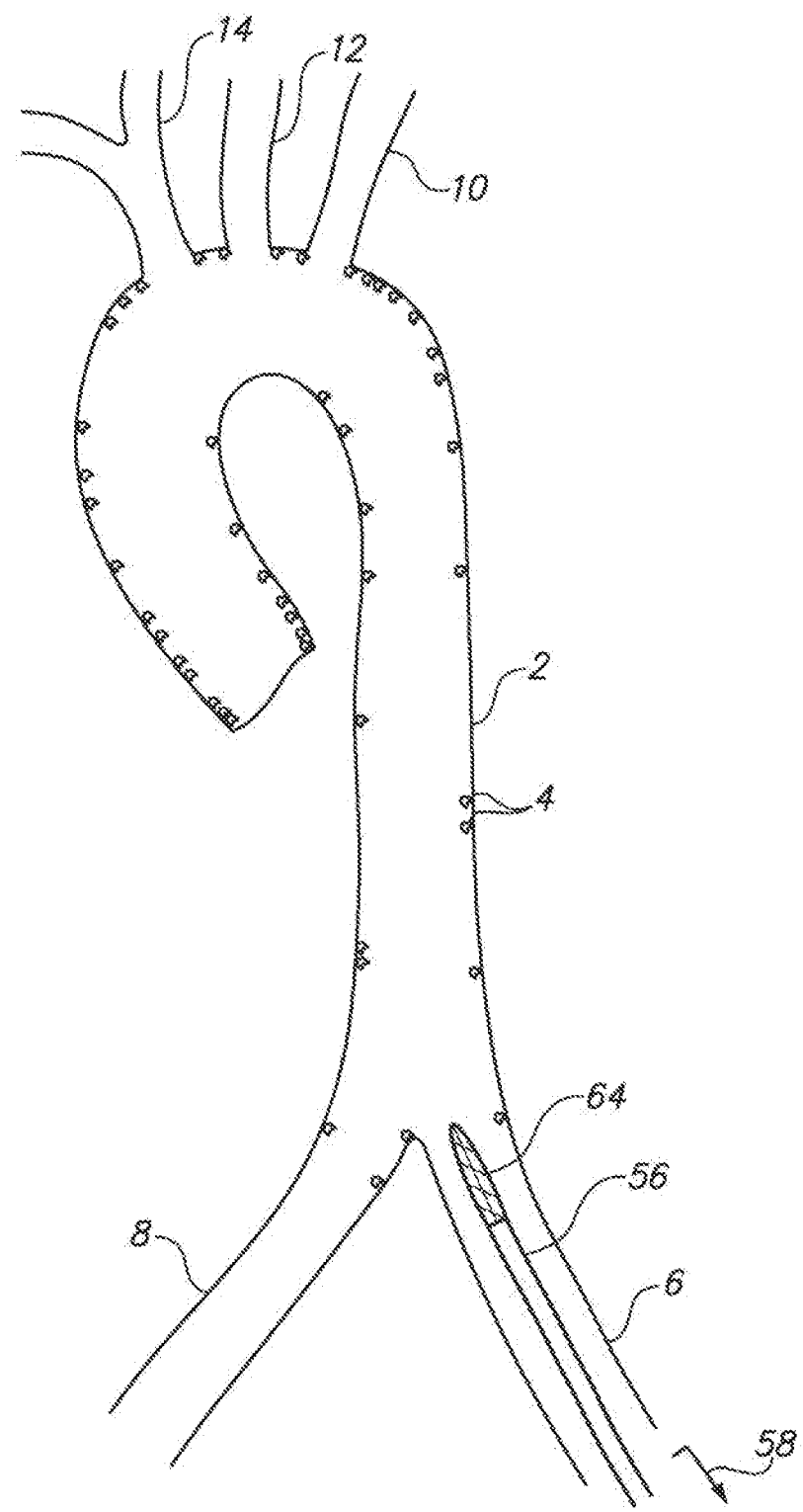

Referring to FIGS. 4A-4H, in one embodiment a separate filtering device, such as that sold under the tradename Embrella® by Edwards Lifesciences, Inc., may be utilized to assist in preventing unwanted particles or emboli from entering certain tributary vessels. Referring to FIG. 4A, a collapsed filtering device (68) may be advanced (62) with an elongate deployment member (66). Referring to FIG. 4B, the filtering device may be converted to an expanded configuration (70) wherein one or more wings (72, 74) form filtrating barriers across one or more tributary vessels (12, 14) and are temporarily retained in place by a retainer member (76). Referring to FIG. 4C, the deployment member (66) may be retracted (78), and as shown in FIG. 4I), a collapsed railed sheath configuration (16) may be advanced (80). Referring to FIG. 4E, the collapsed railed sheath configuration (16) may be utilized as in reference to FIGS. 3A to 3Z-4 above, but with the temporary filter device in place. After the railed sheath has been utilized for a diagnostic and/or interventional procedure, it may be removed, and an elongate recapture device (56) may be inserted (62) to recapture the filtration device (64), as shown in FIGS. 4F and 4G, followed by retraction (58) and completion of the case.

Figure 5A:
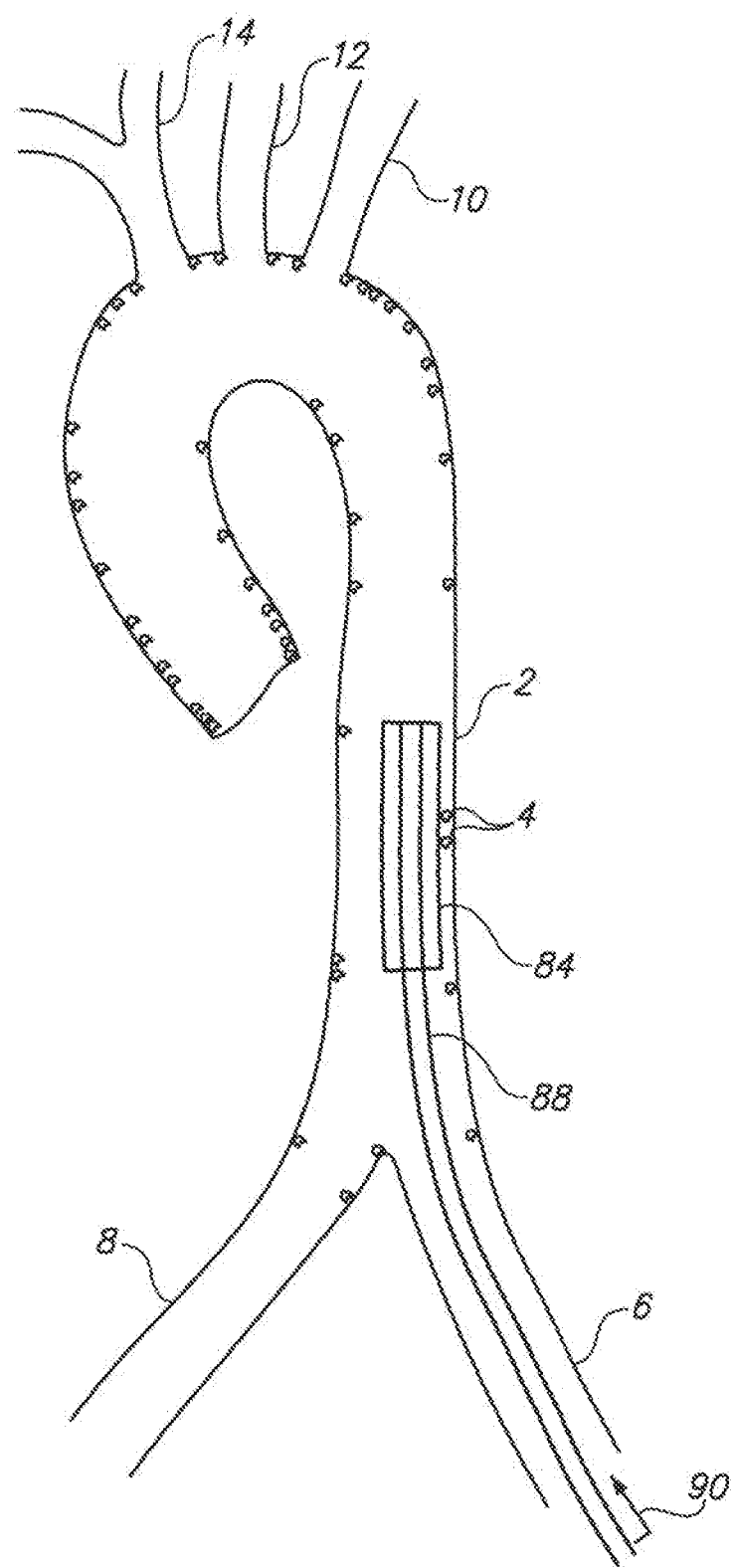
Figure 5B:
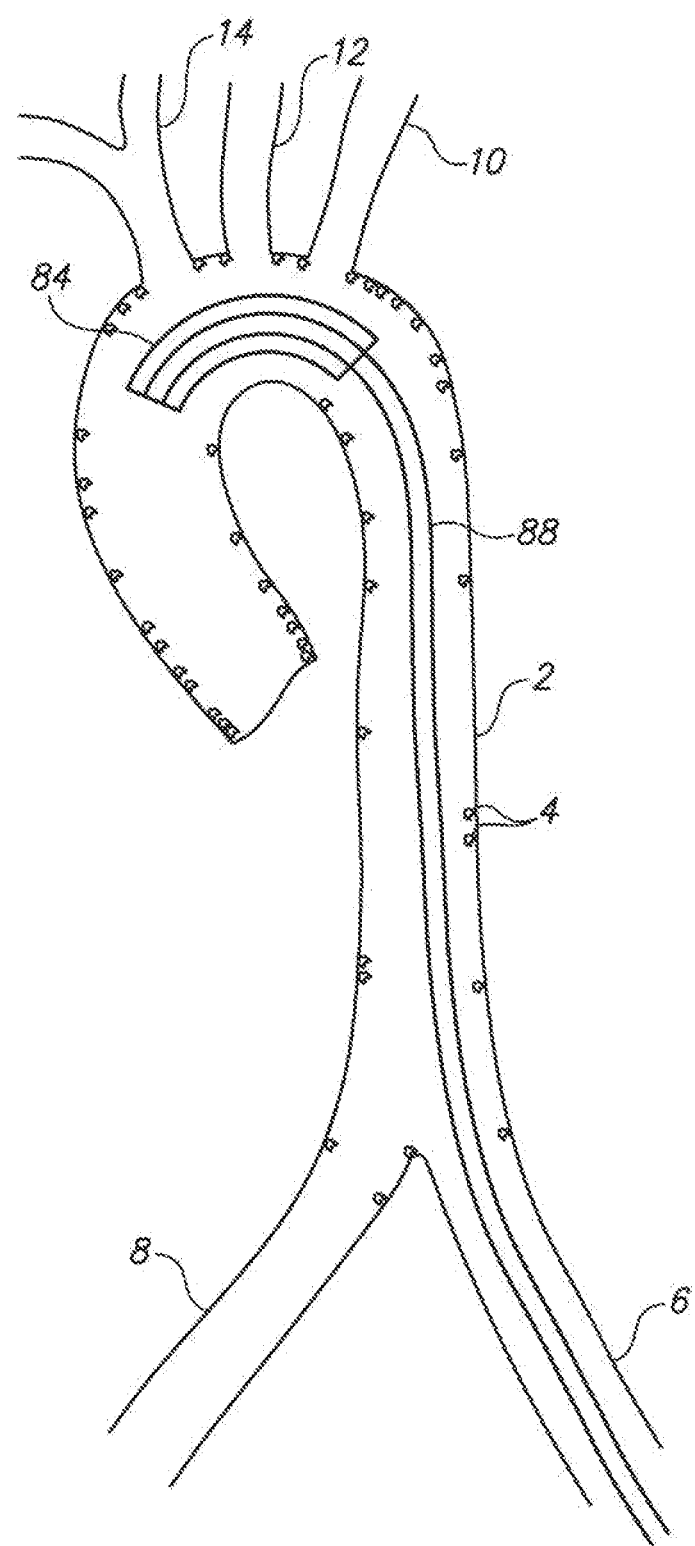
Figure 5C:
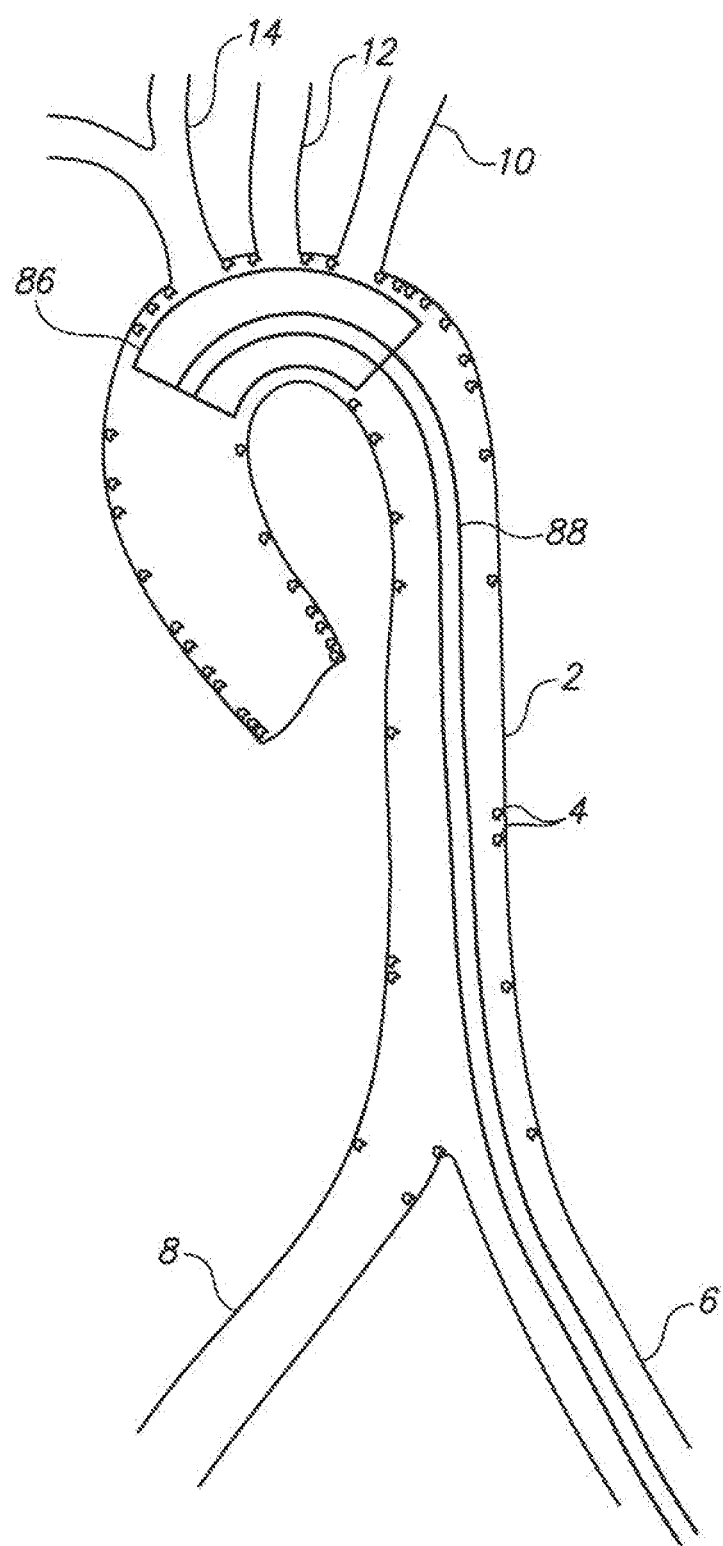
Figure 5D:
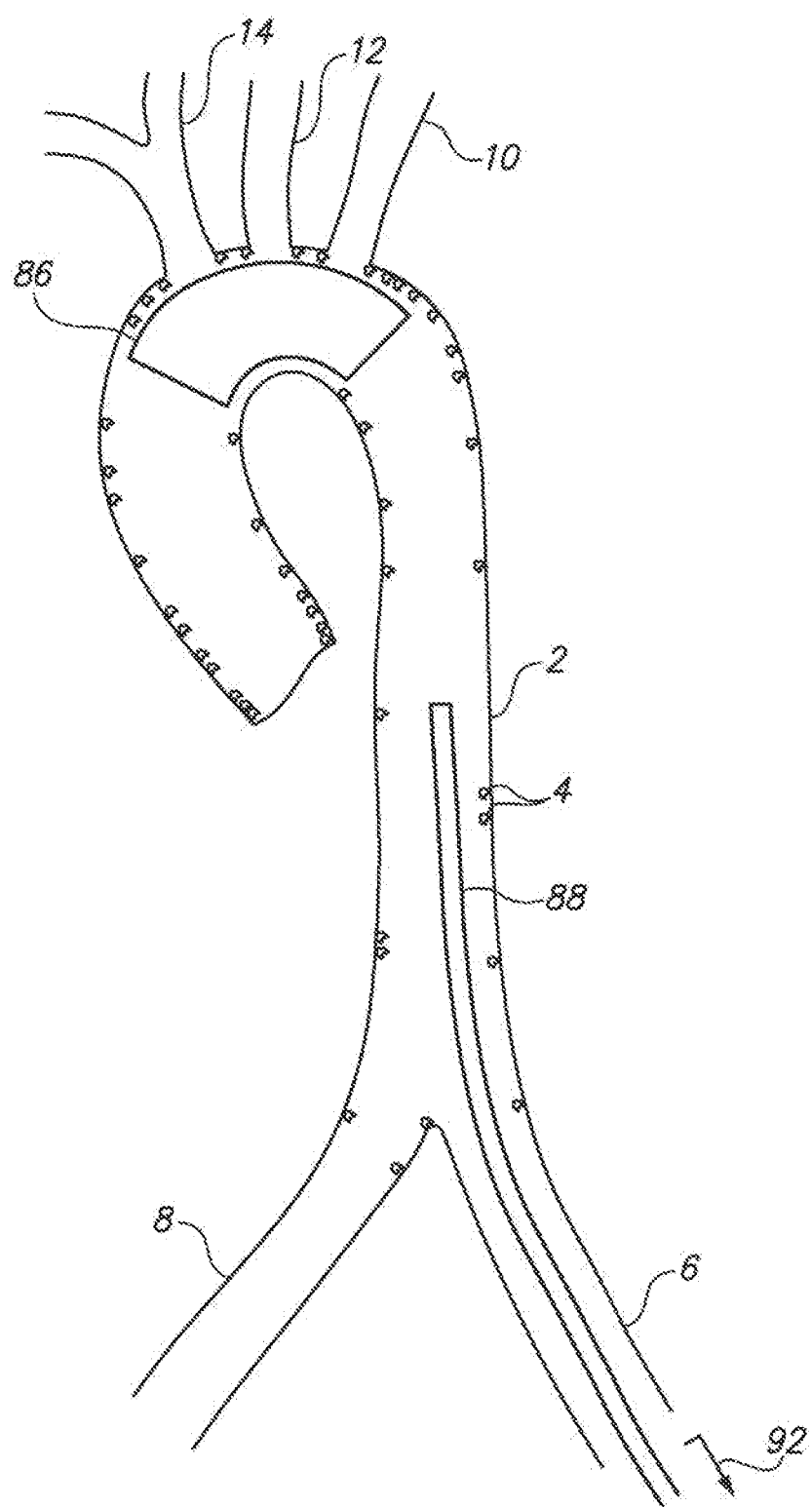
Figure 5E:
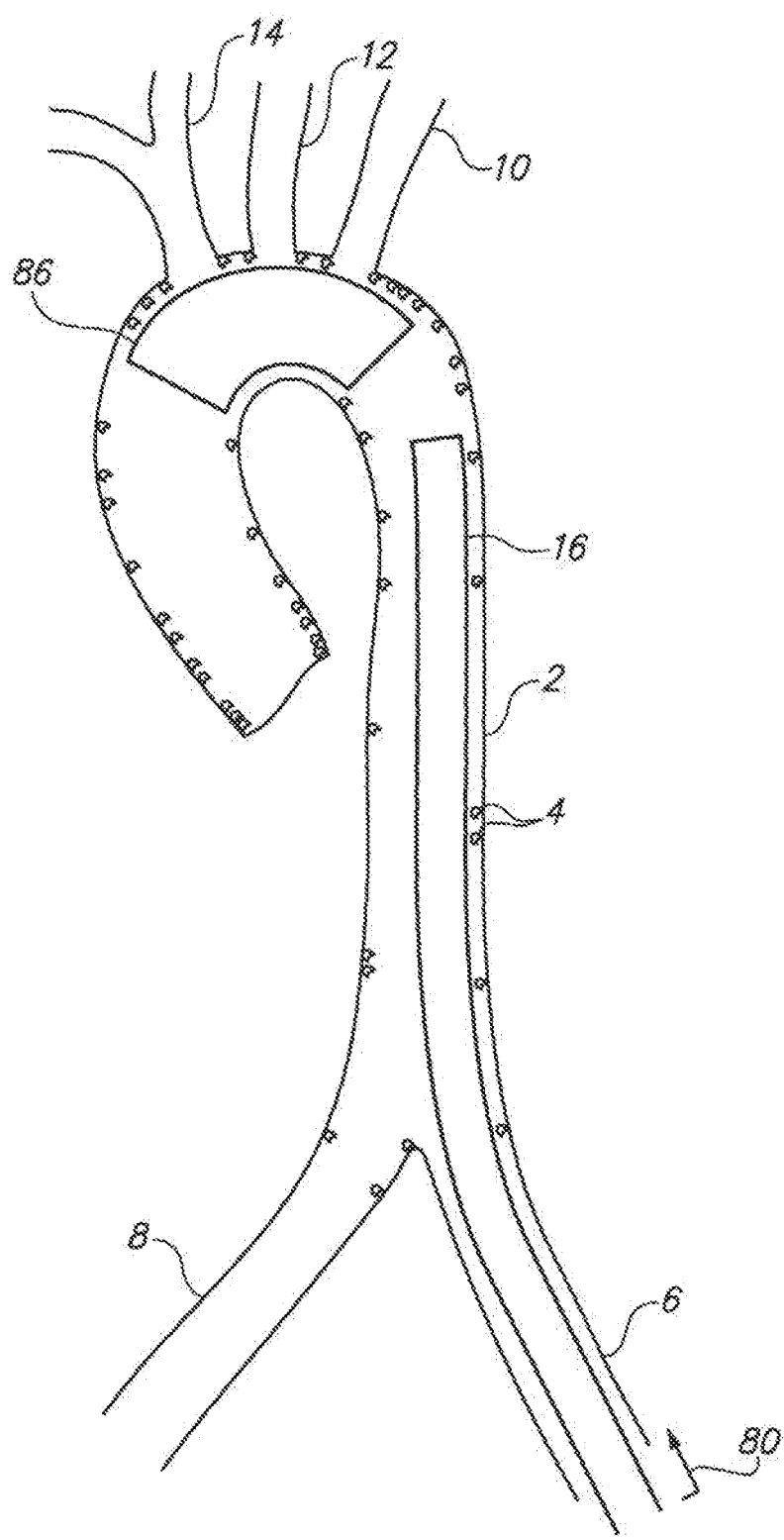
Figure 5F:
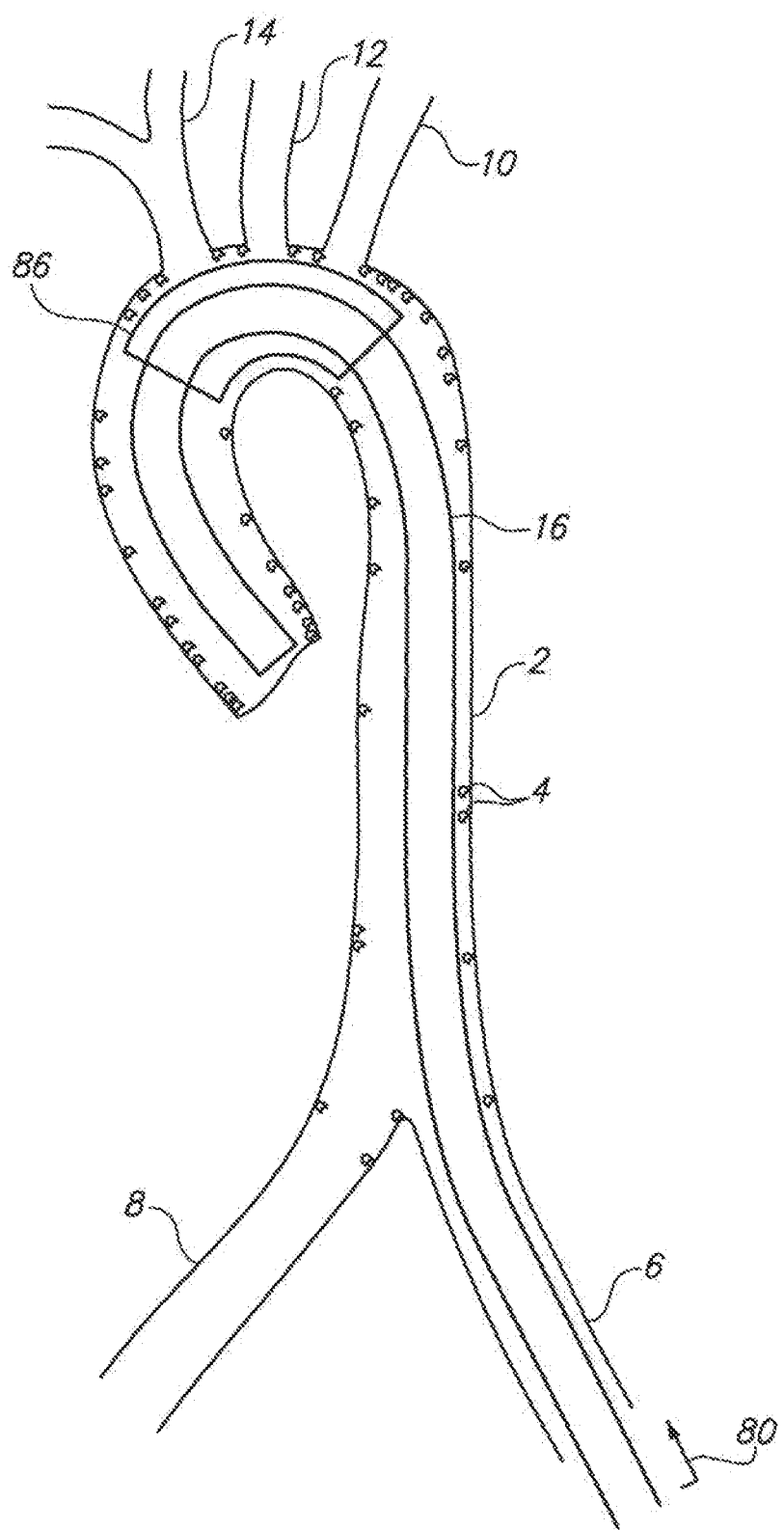
Figure 5G:
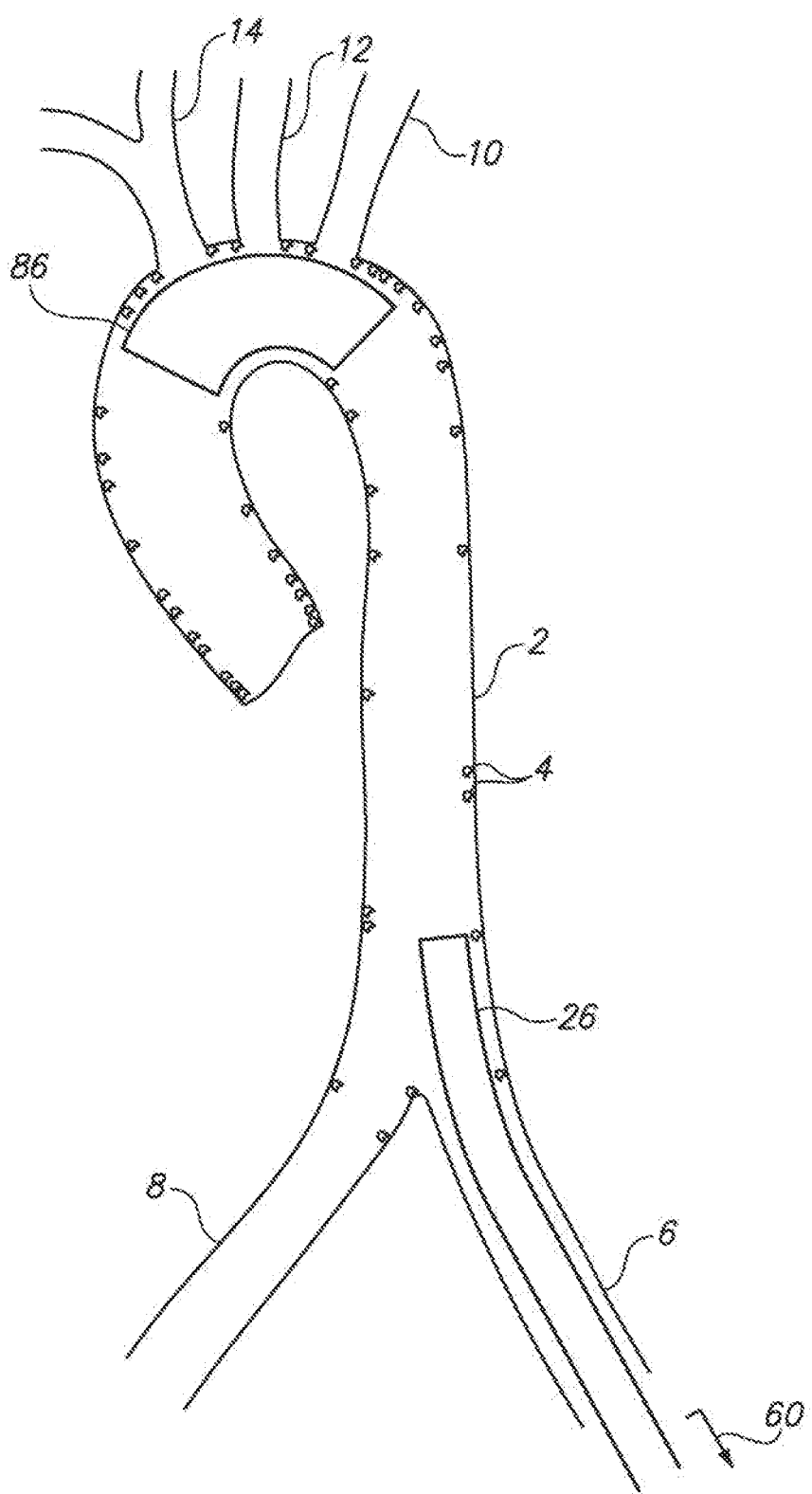
Figure 5H:
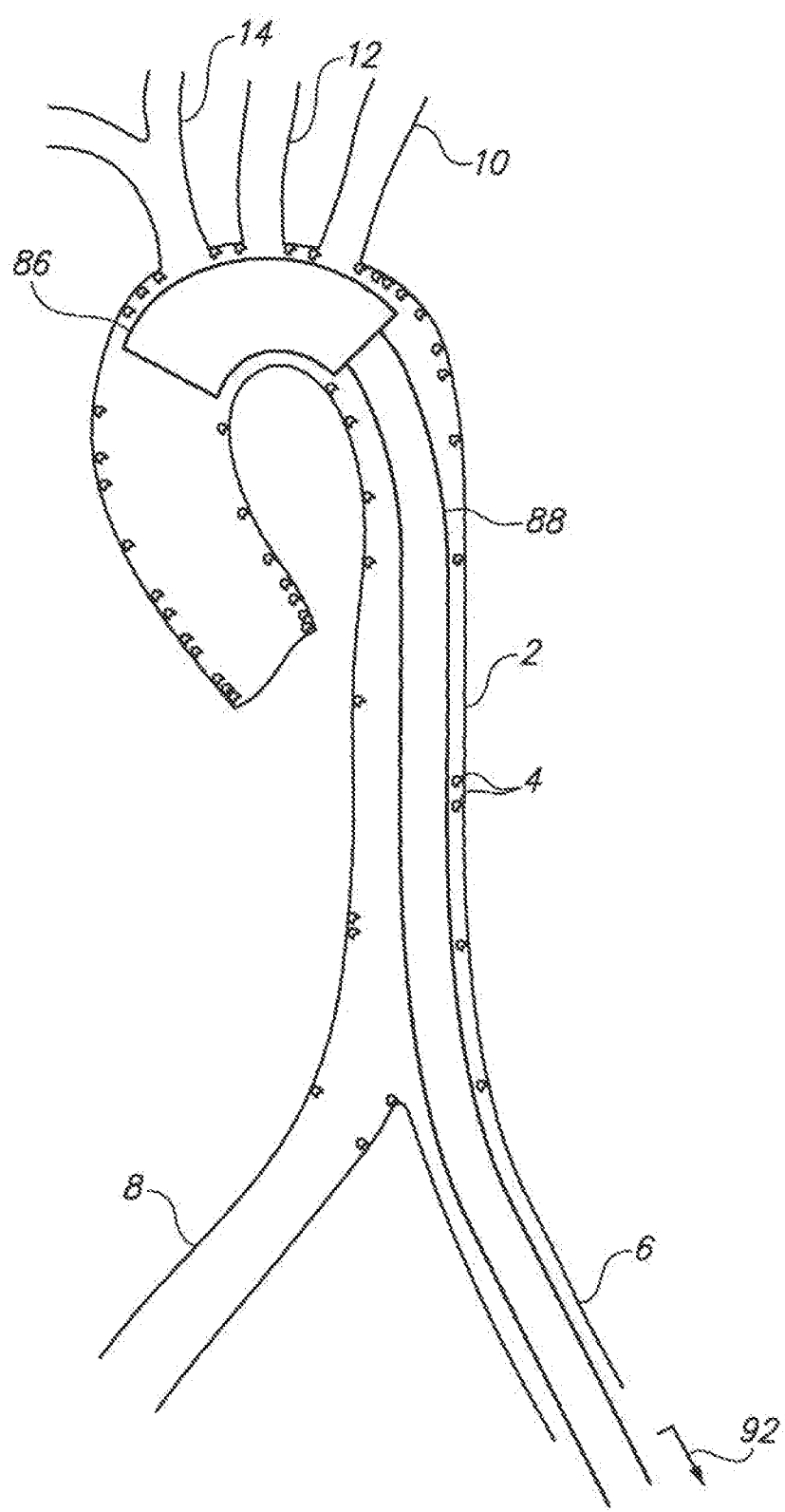
Figure 51:
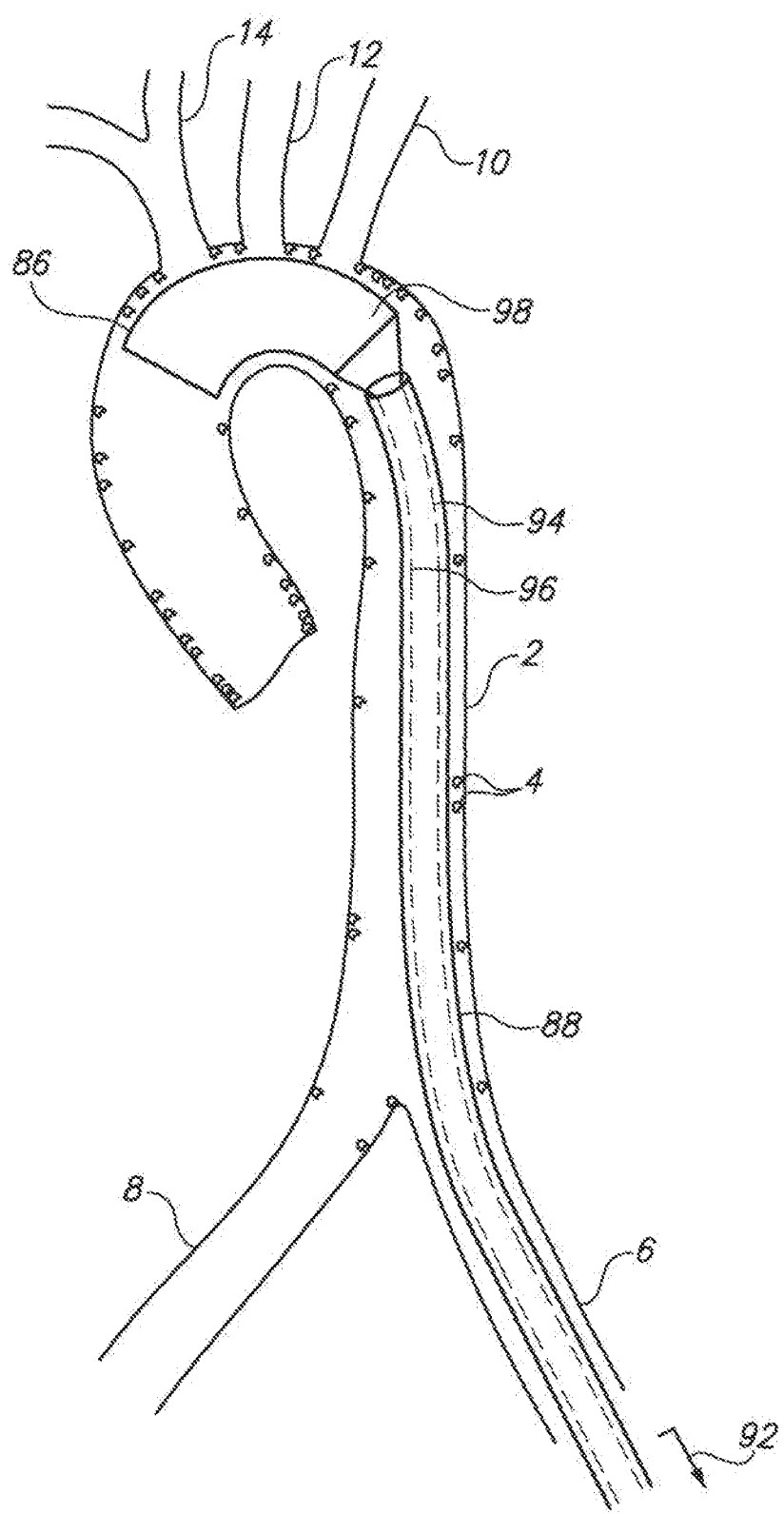
Figure 5J:
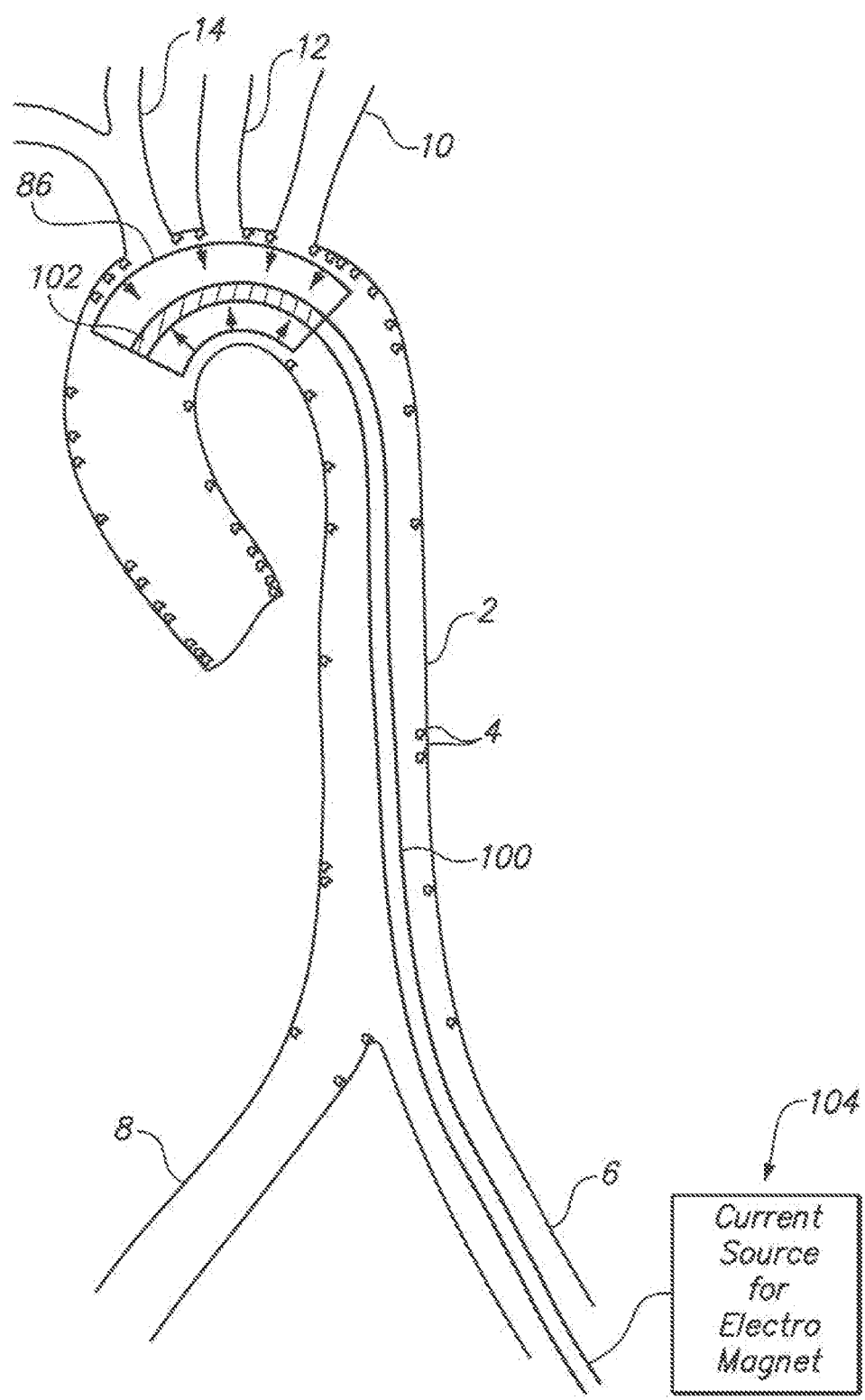
Figure 5K:
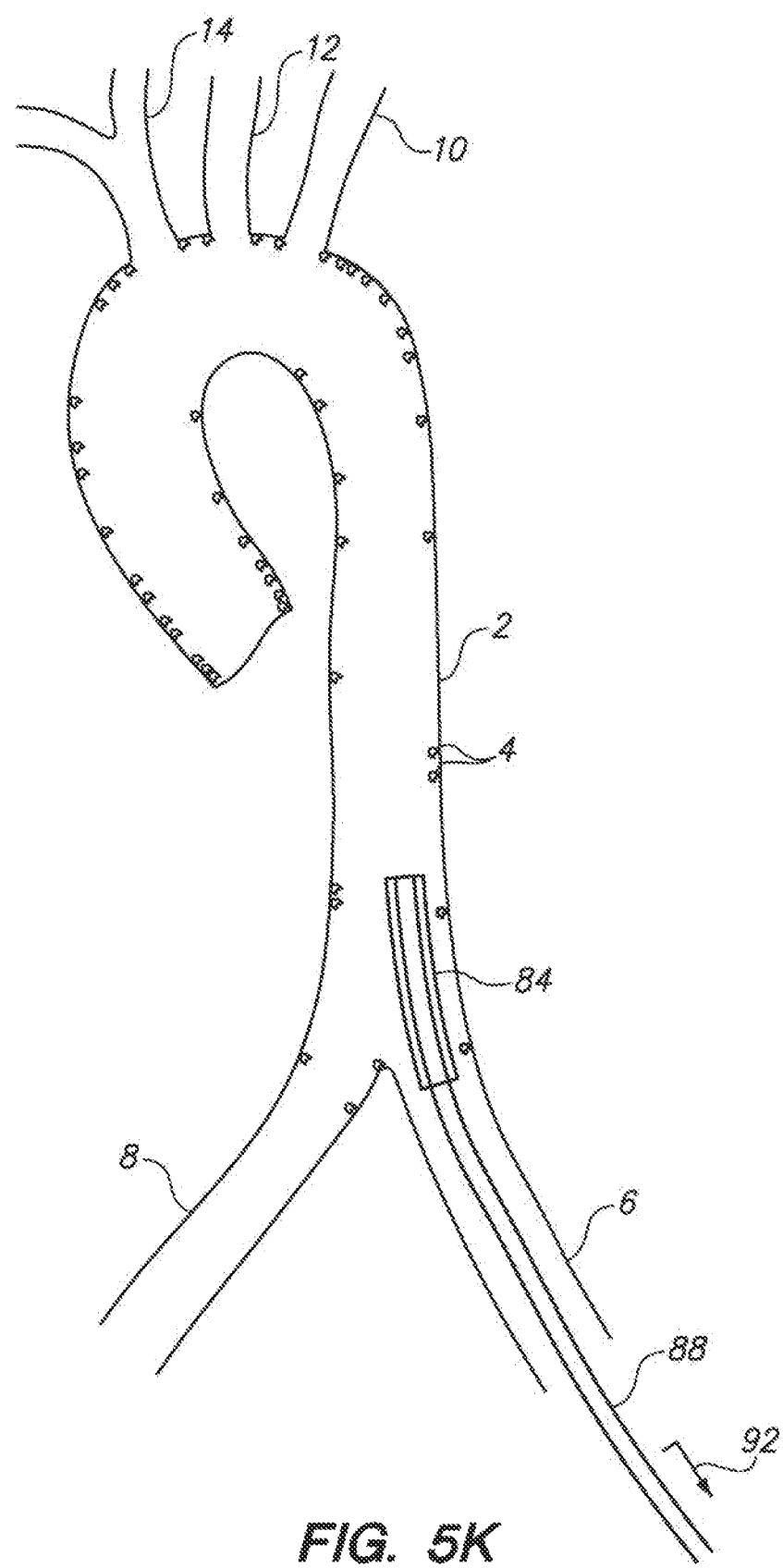

Referring to FIGS. 5A-5K, in another embodiment, a tubular filter may be deployed before installation of a railed sheath to assist with filtering protection at one or more tributary vessel junctions. Referring to FIG. 5A, an elongate deployment member (88) removably coupled to a collapsed tubular filter (84) may be advanced (90) toward the anatomic location of interest, using, for example, fluoroscopic and/or ultrasound imaging guidance, which may be assisted by radiopaque markers on the filter (84) and/or deployment member (88), and/or the injection of imaging contrast agent. Referring to FIG. 5B, with the collapsed tubular filter (84) in the desired longitudinal position, the tubular filter may be converted to the expanded configuration depicted in FIG. 5C, using, for example, a balloon expansion element of the deployment member, or a release of a constraining member that retains a self-expanding configuration of the tubular filter until expansion is desired, after which the restraint is released and expansion ensues to the expanded configuration (86) of the tubular filter, which is configured to screen emboli and/or unwanted particles from entering the associated tributary vessels (10, 12, 14 in the depicted example). The deployment member (88) may be removed (92), as shown in FIG. 5D, and a collapsed railed sheath configuration (16) may be inserted (80) through the expanded tubular filter (86), as shown in FIGS. 5E and 5F, to conduct a procedure in similar fashion as described above in reference to FIGS. 3A to 3-Z4 (in one embodiment the porosity of the porous portion (132) may be increased to maximize flow, since an additional filter is already in place; in another embodiment the porous portion (132) may simply comprise an open window section of the railed sheath). Referring to FIG. 5G, with the procedure coming to completion, the railed sheath (26) may be removed (60), and as shown in FIG. 5H, the filter deployment member (88) may be advanced to recapture the filter and pull it proximally out (92), causing it to slightly collapse and become mobile relative to the anatomy. Referring to FIG. 5I, in another embodiment, two or more pullwires (94, 96) may be coupled to the tubular filter (either intraoperatively, or preoperatively and left in place during the procedure with leads to a proximal manual access point) and utilized to forcibly dislodge the tubular filter for withdrawal by causing radial collapse of at least a proximal portion (98) of the tubular filter (86) as it is pulled toward the small aperture of the deployment member (88) through which the pullwires or tether lines (94, 96) exit to couple to the filter. Referring to FIG. 5J, in another embodiment, a distal portion of an electromagnetic deployment probe (100) may be configured to controllably attract ferromagnetic portions of the tubular filter to draw the filter back into a collapsed state when a voltage source (104) provides electromagnetic attraction toward one or more electromagnets coupled to the distal portion (102) of the electromagnetic deployment probe (100). Referring to FIG. 5K, the tubular filter may be retracted and removed.

Figure 6:
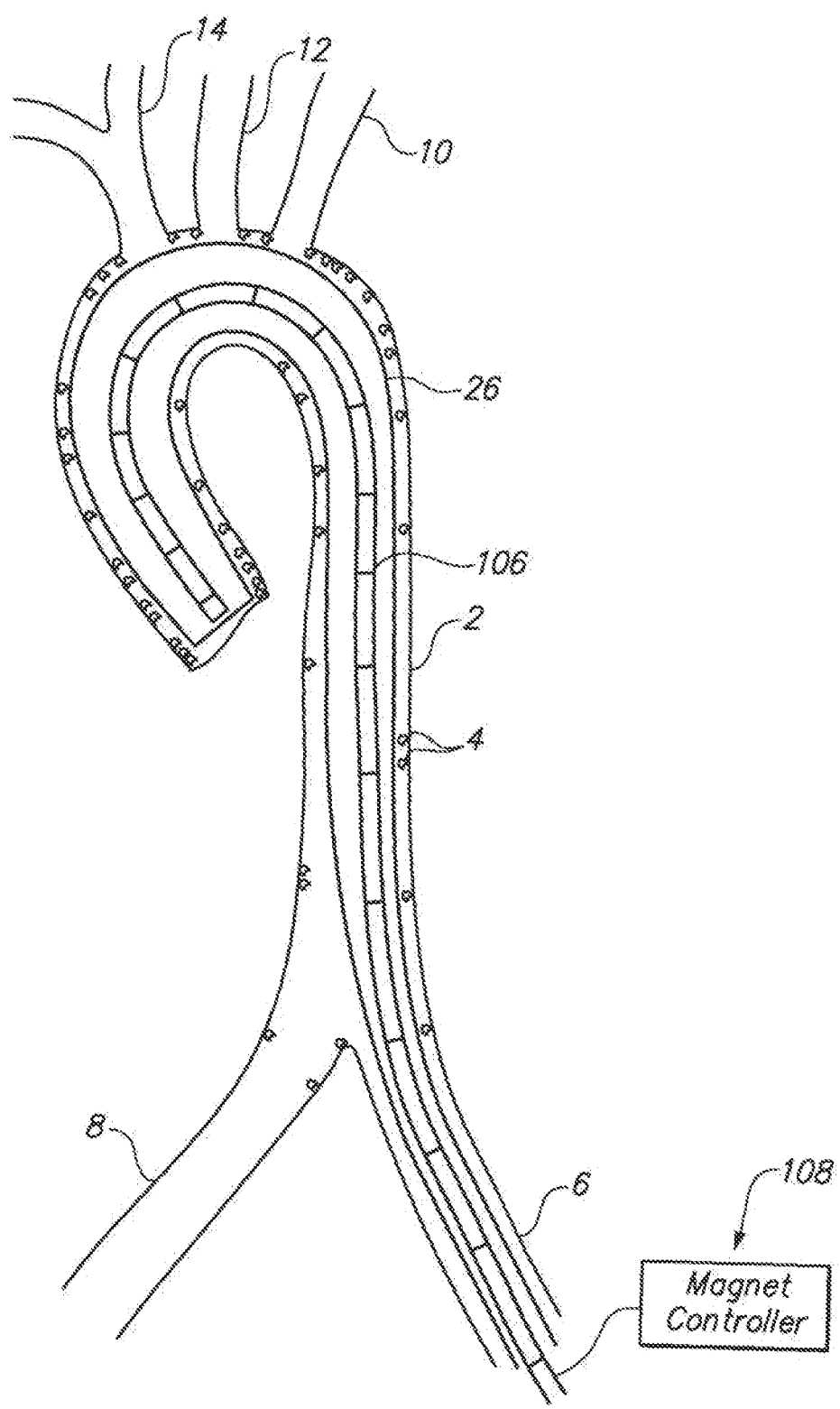
FIG. 6 illustrates a configuration wherein a magnetic probe is utilized to collapse a sheath after an intervention has been conducted through an expanded form of the sheath.

Referring to FIG. 6, a deployment probe (106) with a longer electromagnetic portion than that of FIG. 5K may be utilized to assist in the affirmative re-collapsing of a railed sheath embodiment that comprises ferromagnetic portions which may be controllably attracted toward the electromagnetic deployment probe (106) using an operatively coupled voltage controller (108). In one embodiment, the voltage controller (108) may be configured to activate all of the electromagnets on the probe (106) simultaneously to re-collapse the associated length of the railed sheath simultaneously. In another embodiment, the controller (108) may be configured to sequentially activate (and retain activation until release is desired) the various electromagnets comprising the probe to provide for a sequential longitudinal collapsing of the associated railed sheath (i.e., from the most proximal portion to the most distal portion, vice versa, etc.).

Figure 7:
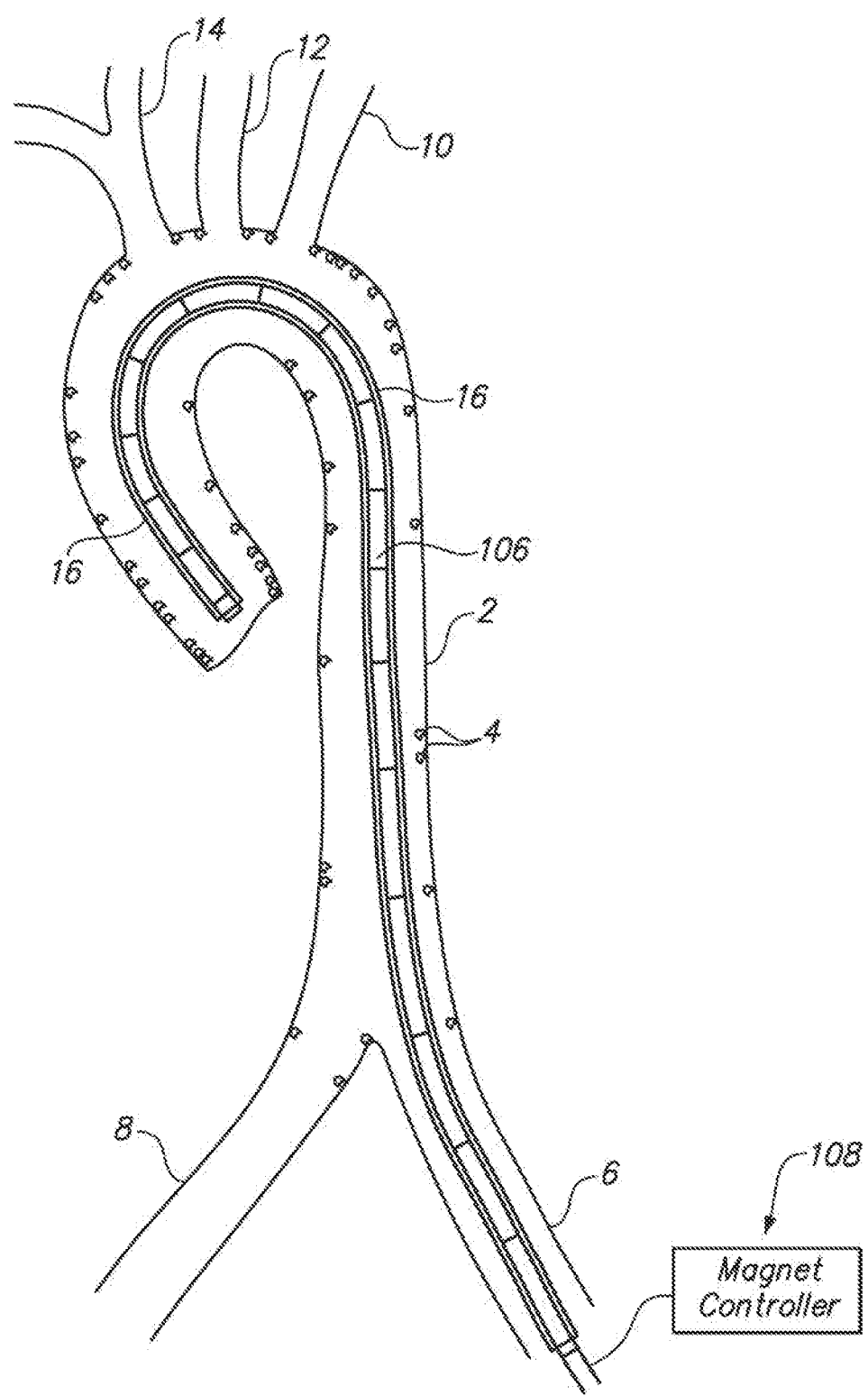
FIG. 7 illustrates a configuration wherein a magnetic probe is utilized to retain a sheath in a collapsed form until an expansion to an expanded form is desired.

Referring to FIG. 7, a deployment probe (106) similar to that depicted in FIG. 6 may be utilized to forcibly retain a collapse configuration until sequential or simultaneous expansion of all portions of the railed sheath is desired. In other words, the magnet controller (108) may be configured to retain the collapsed state of the entire exposed length of the railed sheath during insertion. When the desired longitudinal positioning has been accomplished, the magnet controller may be configured to either simultaneously or sequentially release portions of the railed sheath to allow for expansion to the expanded form (26). Completion of expansion to the expanded form (26) may be completed as a result of a self-expanding infrastructure of the railed sheath, with the help of an expandable balloon, etc.

Figure 8A:
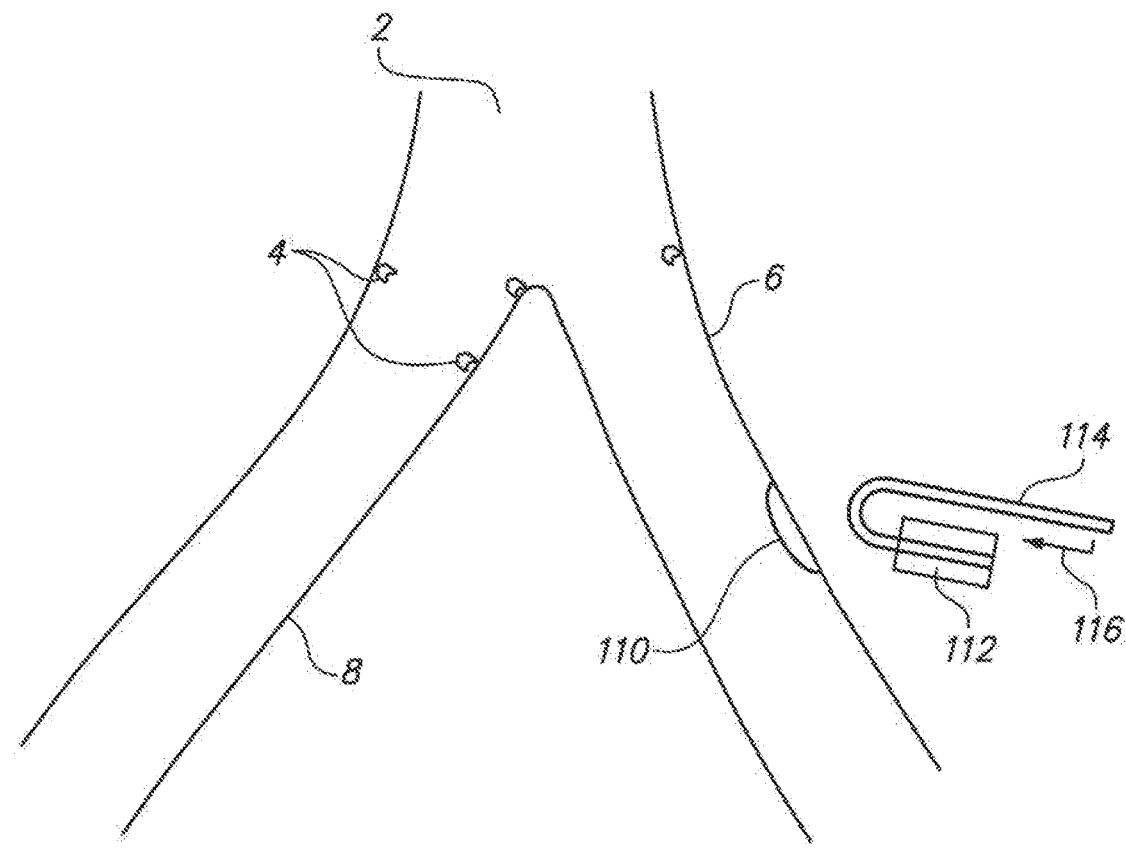
FIGS. 8A-8G illustrate aspects of a configuration similar to that of FIGS. 3A-3Z-4, wherein a distal protection filter is also incorporated.
Figure 8B:
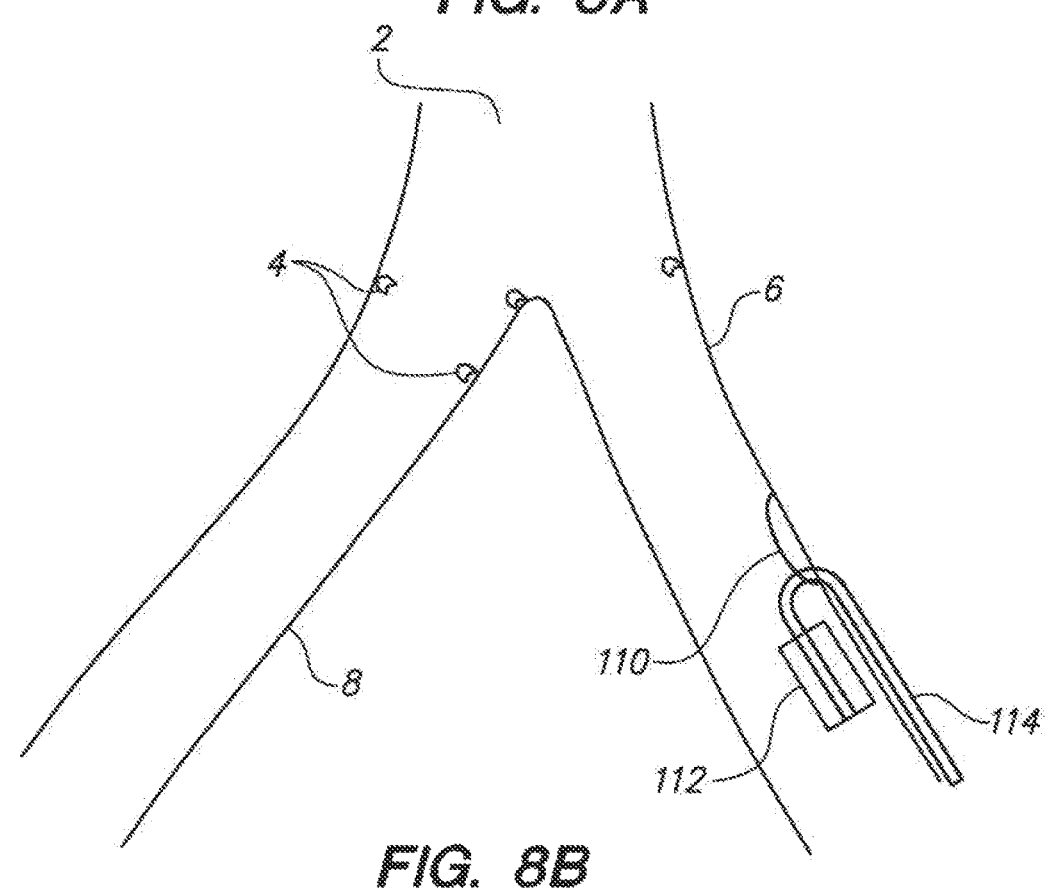
Figure 8C:
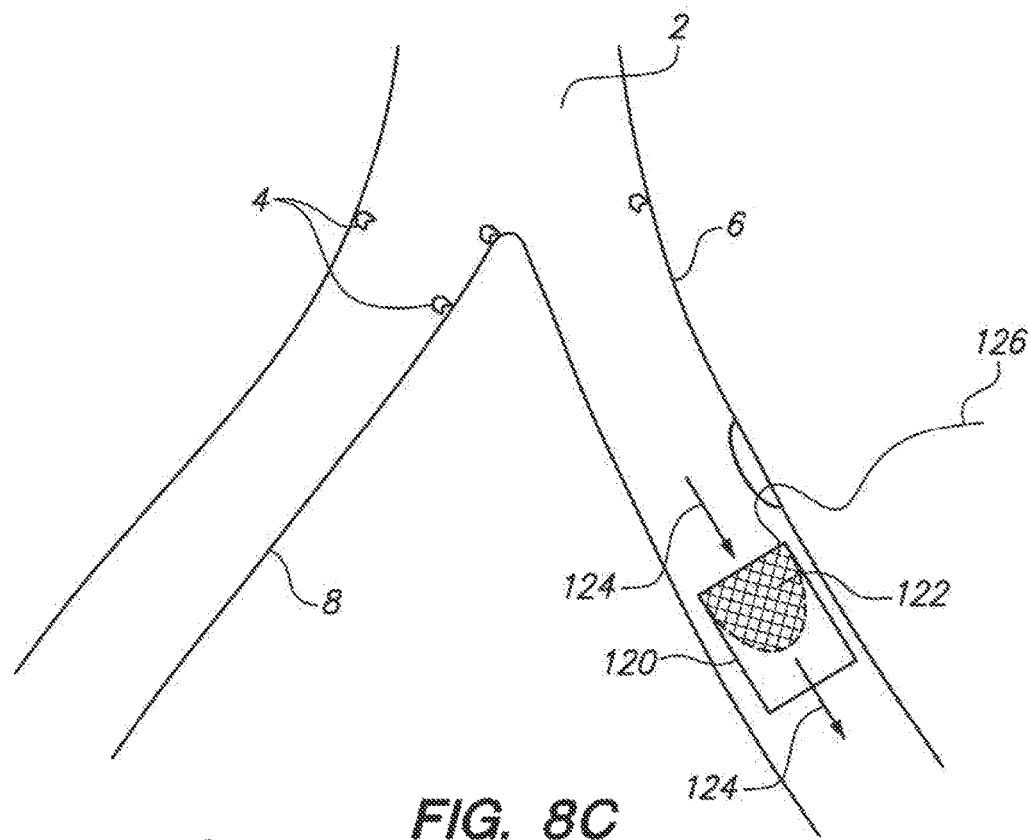
Figure 8D:
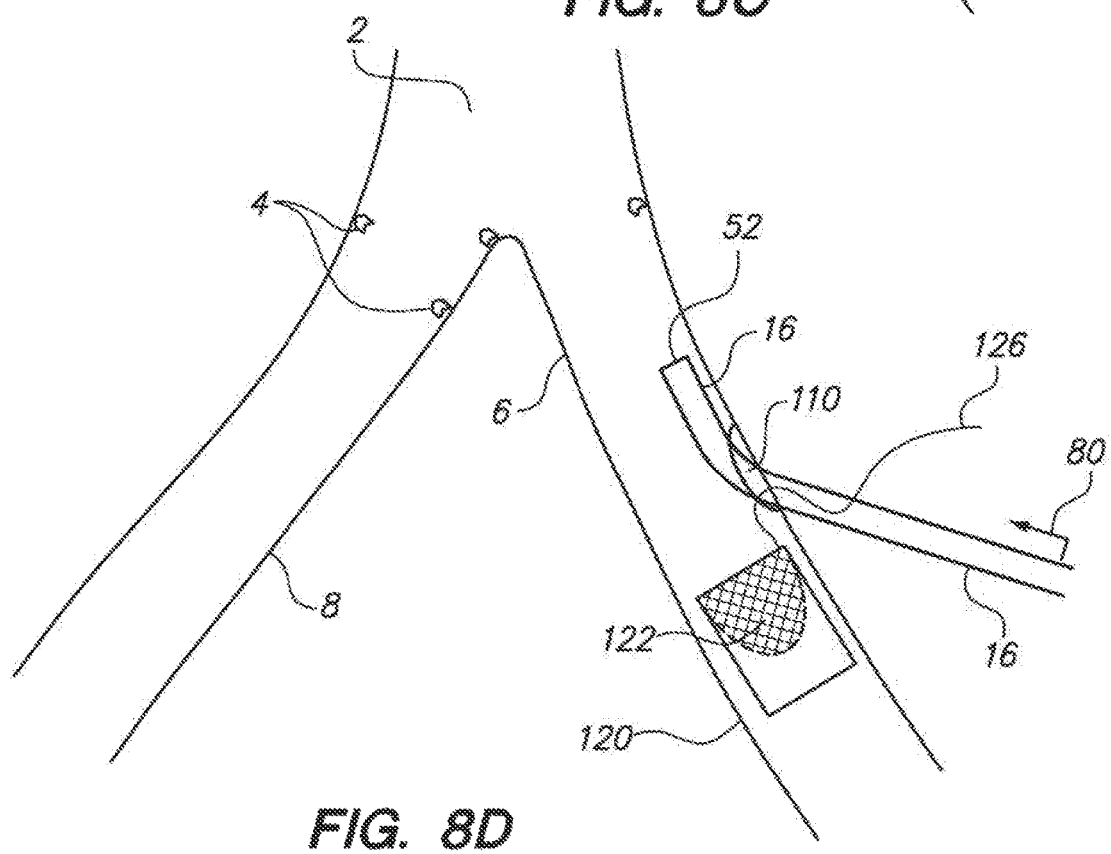
Figure 8E:
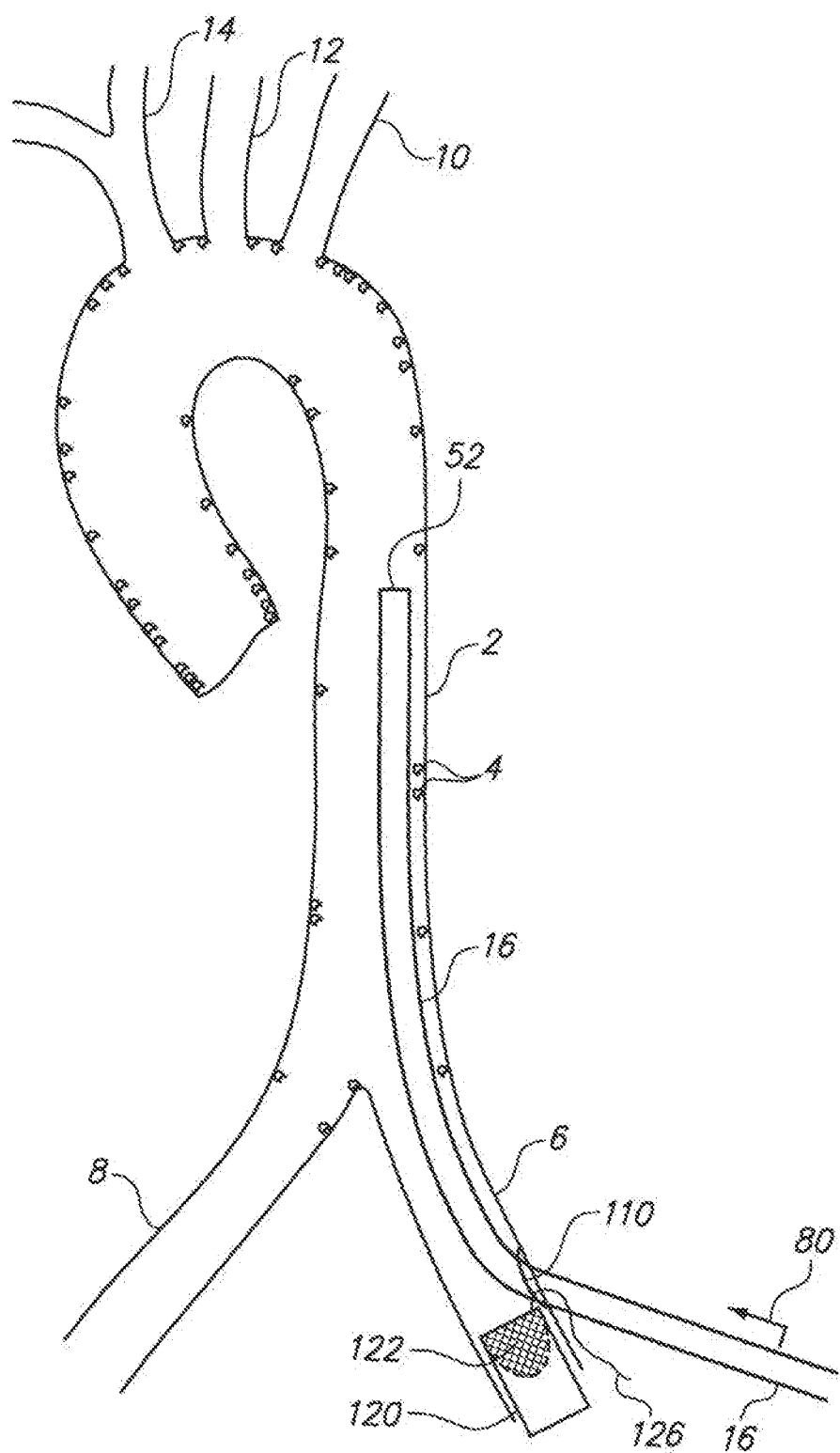
Figure 8F:
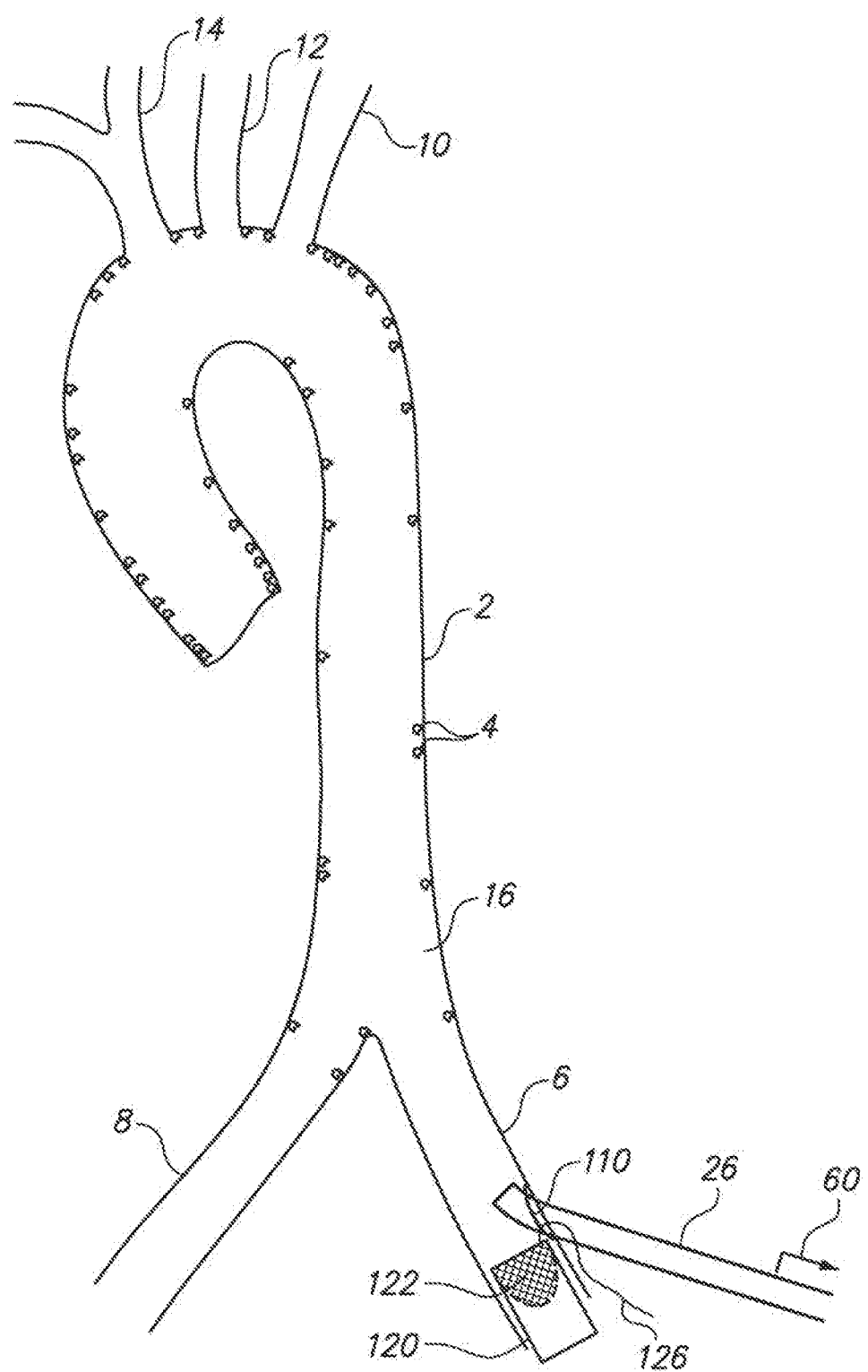
Figure 8G:
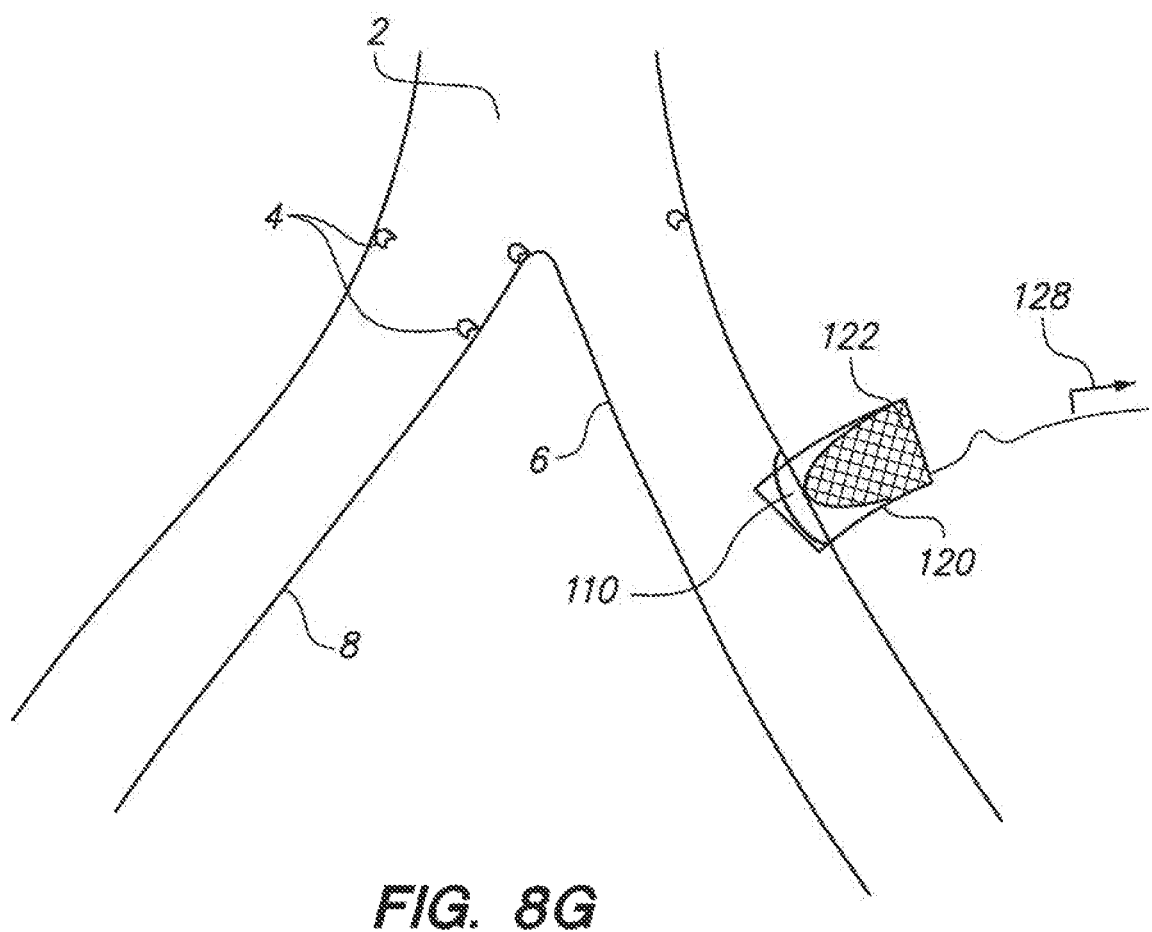

Referring to FIGS. 8A-8G, a proximal filter, or "distal protection device", may be placed proximal to the access point for the aforementioned hardware embodiments to prevent particles or emboli from flowing distally. Referring to FIG. 8A, a close up view of an access point (110, such as an arteriotomy) and associated vessels (6, 8) and deposits (4) is shown with a collapsed filtration device (112) being advanced (116) with a deployment member (114) through the access point (110). Referring to FIG. 8B, the deployment member (114) may be shaped such that the collapsed filtration device (112) can be tucked immediately proximal of the access point (110). As shown in FIG. 8C, the filtration device may be self-expanding or expandable (i.e., with a balloon) to be controllably converted into an expanded/deployed configuration (120) wherein blood flow (124) is directed across a filter mesh (112) portion of the expanded filter (120) to prevent passage of emboli, particles, and the like. Preferably the filter (120) has a tether member (126) which may be extended out of the access point (110) and used subsequently for recapture and removal of the filter. Referring to FIGS. 8D and 8E, with the expanded filter (120) in place, a collapsed railed sheath (16) may be advanced and utilized as in the embodiments described in reference to FIGS. 3A to 3Z-4, with the further benefit of the distal protection filter in place. With the procedure coming to a close, the railed sheath (26) may be retracted (60) past the still-deployed filter (120), as shown in FIG. 8F, after which the tether member (126) may be utilized to assist in retraction (128) of the filter member out of the access point (110) and completion of the procedure.

Figure 9:
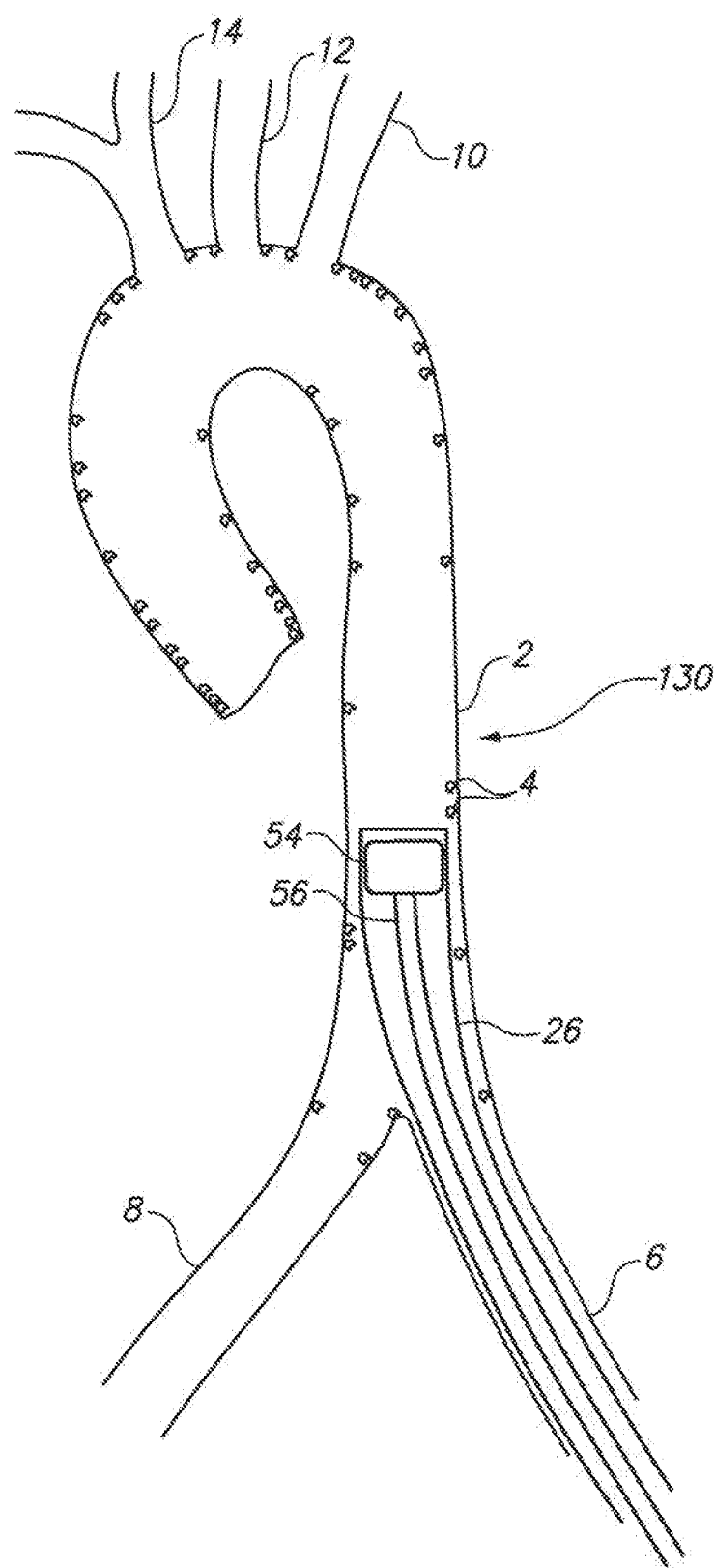
FIG. 9 illustrates aspects of a configuration similar to that of FIGS. 3A-3Z-4, wherein only a proximal portion of the main vessel is protected by an embodiment of the inventive sheath.

Referring to FIG. 9, a railed sheath may be utilized to only partially protect a route to a targeted anatomical position for a diagnostic and/or interventional instrument. For example, if the main objective is to protect the subject vessel pathway between the lower ascending aorta (130) and the access point, a railed sheath (26) may be deployed only across this length, and the instrumentation (56, 54) may be advanced across this length through the railed sheath (26), and then across the remainder of the length of the vessel to the targeted anatomy without the protection and/or mechanical guidance of the railed sheath.

Figure 10:
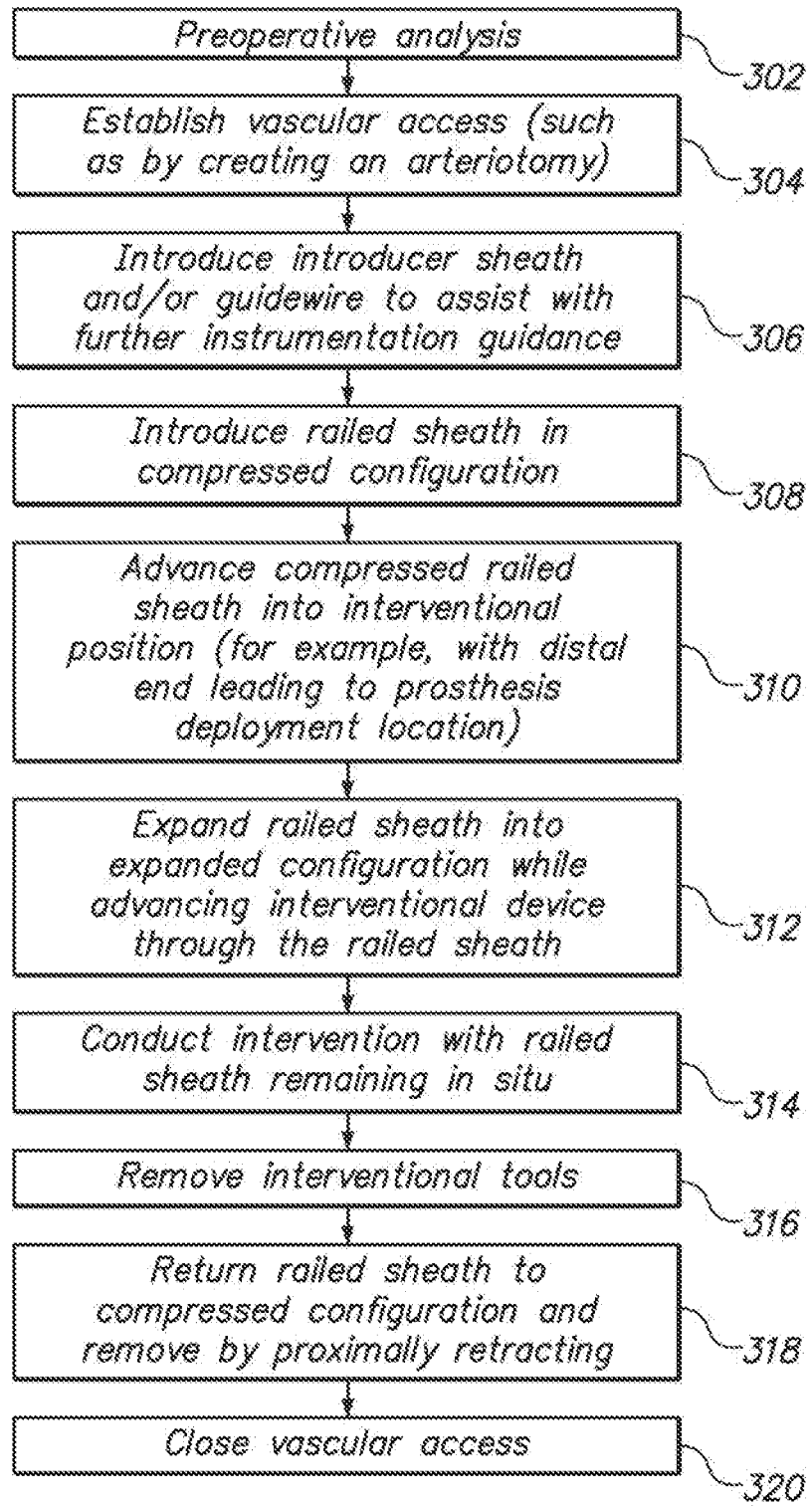
FIG. 10 illustrates various aspects of a deployment technique in accordance with the present invention.

Referring to FIG. 10, a deployment technique is illustrated wherein subsequent to preoperative analysis (302) and establishment of vascular access (304), a guidewire and/or introducer sheath may be advanced across the access location to provide for guidance and support of additional instrumentation which may be advanced (306). A compressed configuration of a railed sheath may be advanced—for example, over-the-guidewire and through the introducer sheath—in a compressed configuration (308). Once the railed sheath has reached a desired longitudinal position (310) for the interventional and/or diagnostic procedure, the railed sheath may be expanded or allowed to expand to, for example, accommodate passage of an advancing interventional device (such as a percutaneous valve deployment assembly) across the railed sheath to the anatomical location of interest (312). With the expanded configuration of the railed sheath remaining in situ, the procedure may be conducted (314), after which the tools may be retracted (316), the railed sheath returned to a collapsed or partially collapsed configuration (for example, by simple proximal tensioning to partially collapse the railed sheath, by electromagnet-induced force to fully collapse the railed sheath, etc.) (318), and vascular access closed (320) to complete the procedure.

Figure 11:
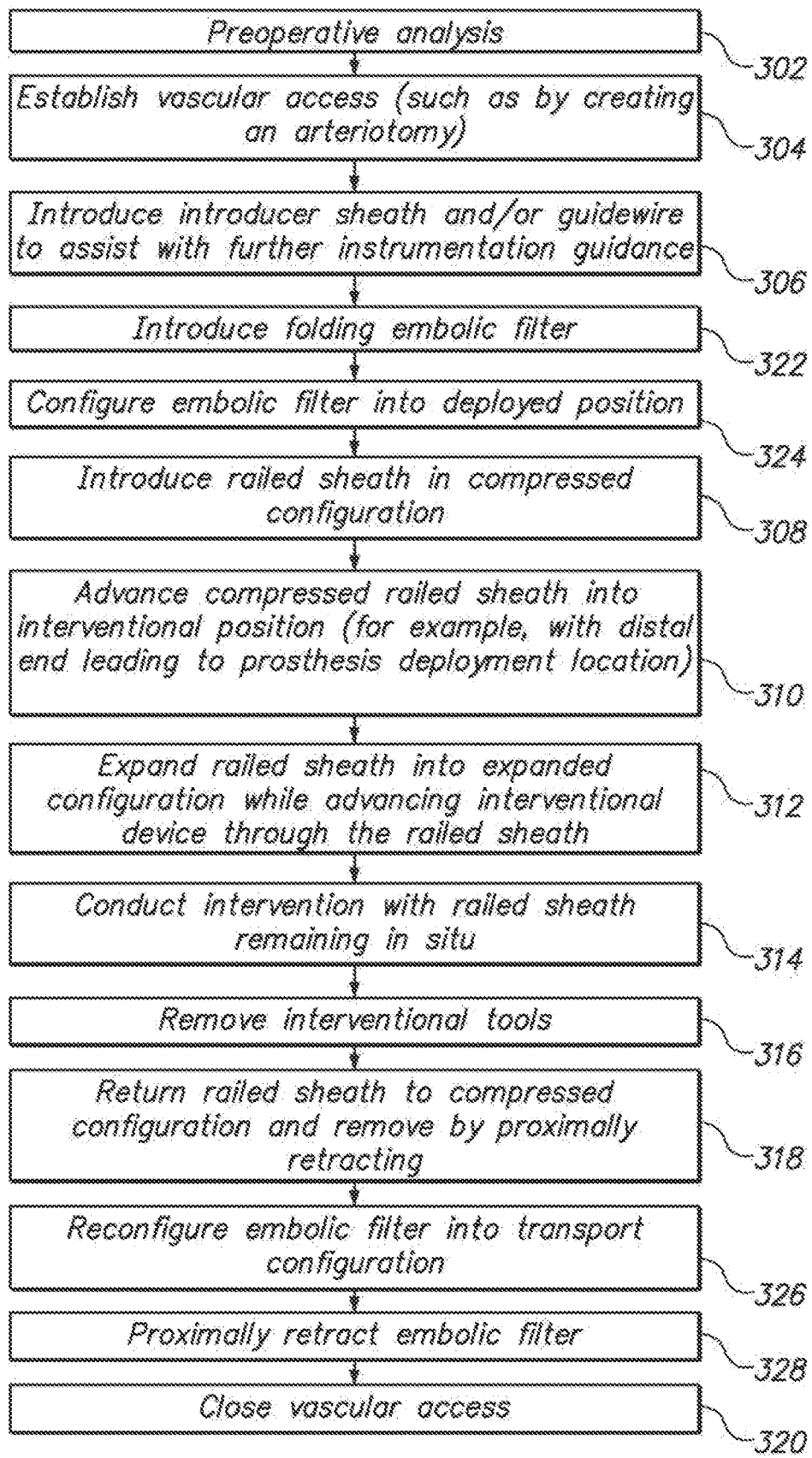
FIG. 11 illustrates various aspects of a deployment technique in accordance with the present invention.

Referring to FIG. 11, an embodiment similar to that of FIG. 10 is illustrated, with the exception that a folding embolic filter may be advanced (322) and deployed (324) prior to introduction of the railed sheath (308); this filter may be reconfigured into a collapsed transport configuration (326) and retracted (328) before final closing of the vascular access (320).

Figure 12:
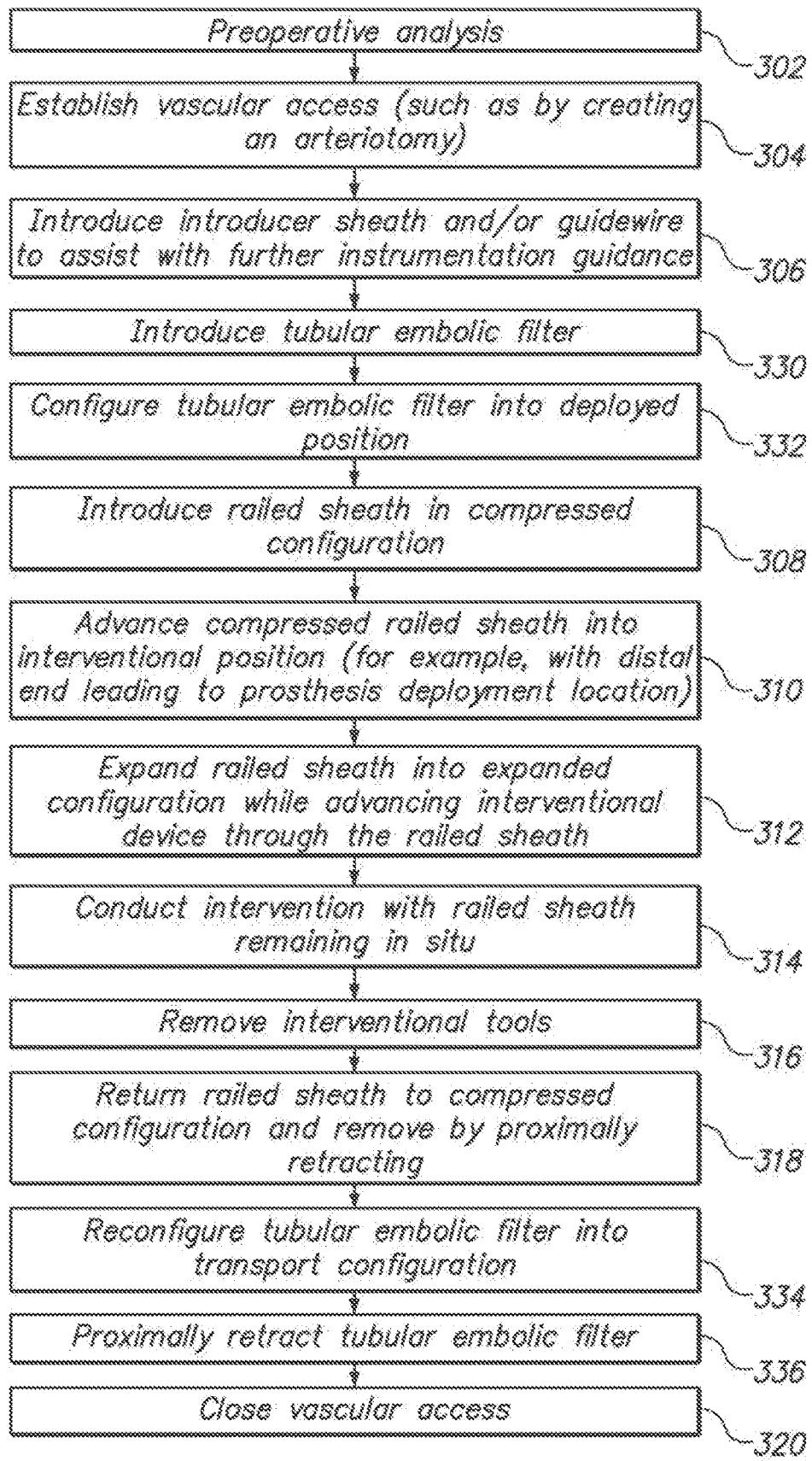
FIG. 12 illustrates various aspects of a deployment technique in accordance with the present invention.

Referring to FIG. 12, an embodiment similar to that of FIG. 10 is illustrated, with the exception that a tubular embolic filter may be advanced (330) and deployed (332) prior to introduction of the railed sheath (308); this filter may be reconfigured into a collapsed transport configuration (334) and retracted (336) before final closing of the vascular access (320).

Figure 13:
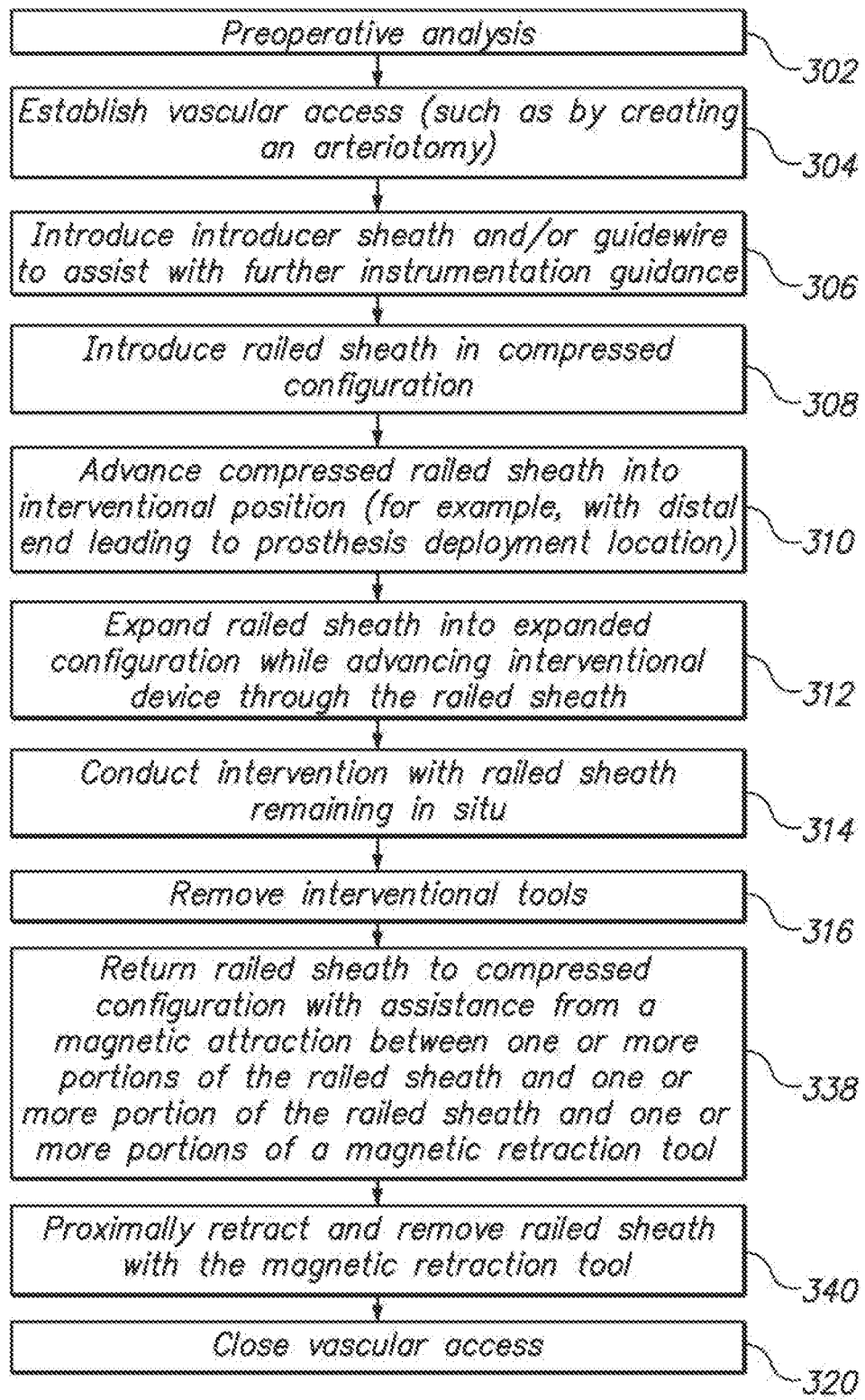
FIG. 13 illustrates various aspects of a deployment technique in accordance with the present invention.

Referring to FIG. 13, an embodiment similar to that of FIG. 10 is illustrated, with the exception that after removal of the interventional tools (316), the railed sheath may be returned to a compressed configuration with the help of magnet-induced loads from a magnetic probe or portion of a probe (338) before retraction using the probe (340).

Figure 14:
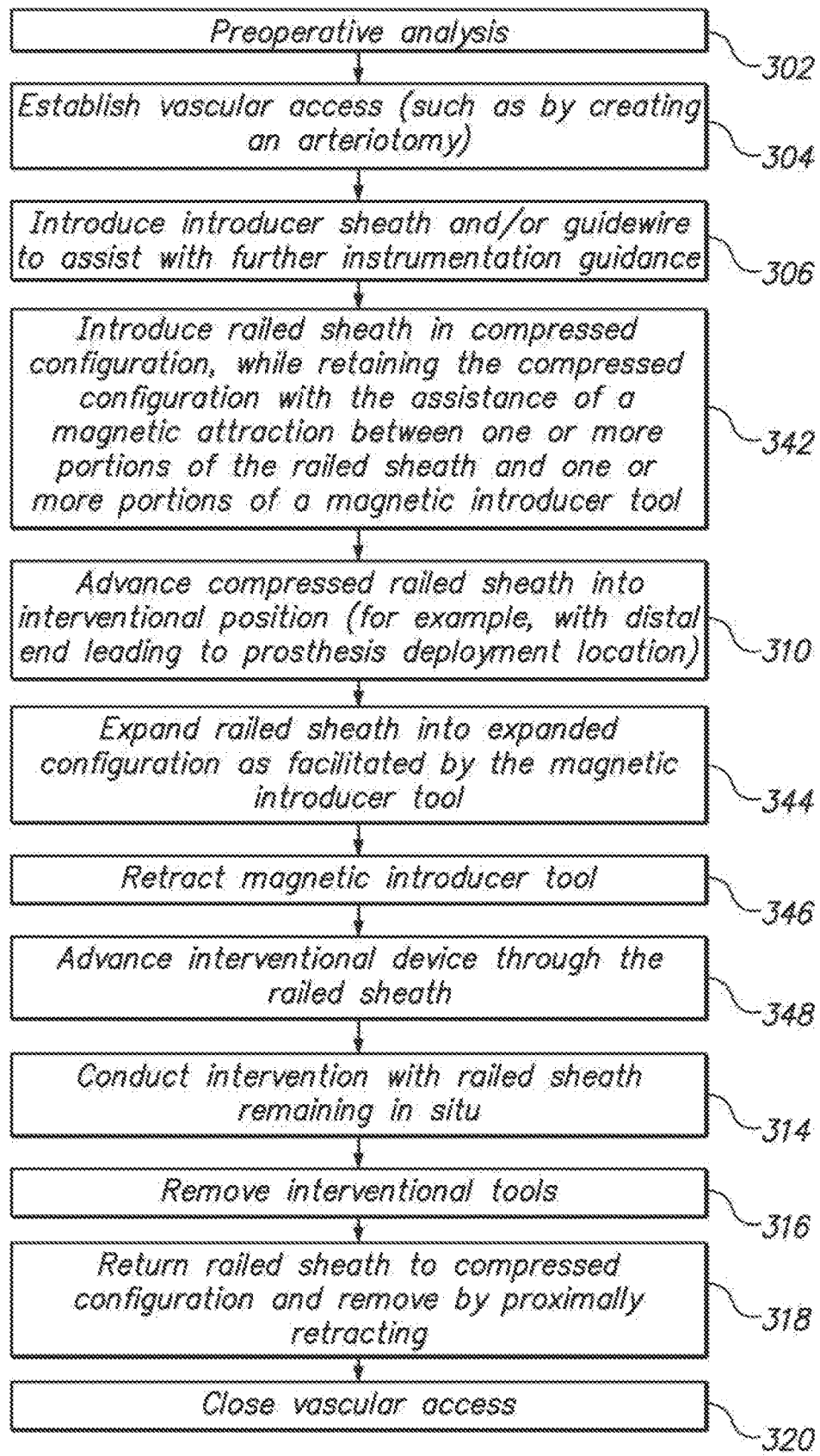
FIG. 14 illustrates various aspects of a deployment technique in accordance with the present invention.

Referring to FIG. 14, an embodiment similar to that of FIG. 10 is illustrated, with the exception that for railed sheath introduction, the collapsed configuration is actively maintained using magnetic loads (342), and expansion (344) to the expanded configuration after appropriate longitudinal advancement (310) is controllably facilitated by controllably decreasing or removing the magnetic loads, followed by retraction of the magnetic tool (346) and advancement of the interventional or diagnostic tools through the railed sheath (348).

Figure 15:
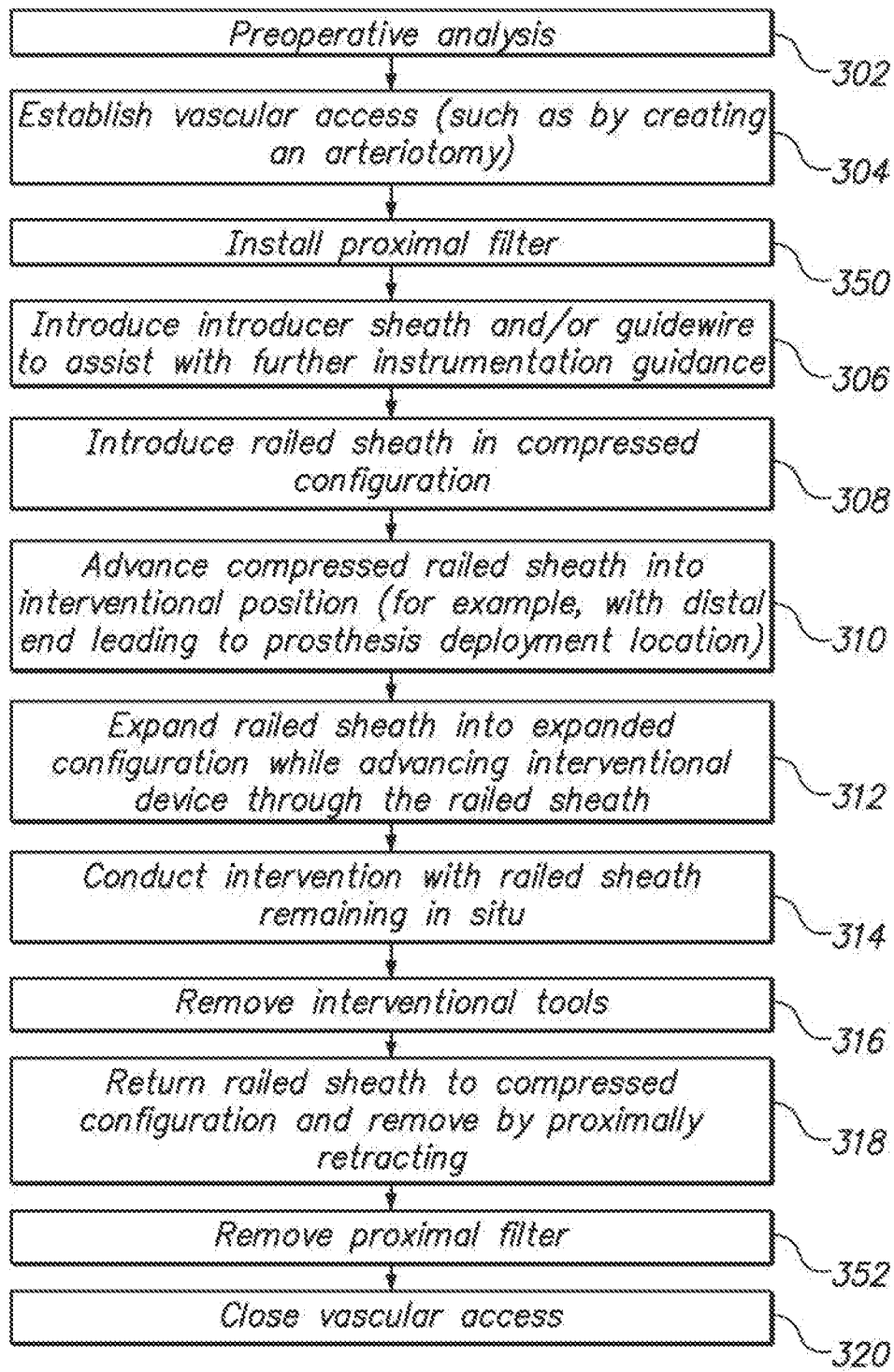
FIG. 15 illustrates various aspects of a deployment technique in accordance with the present invention.

Referring to FIG. 15, an embodiment similar to that of FIG. 10 is illustrated, with the exception that after vascular access is established (304), a proximal filter, or "distal protection device" is installed (350) proximally; this filter may be removed (352) after ultimate removal of the railed sheath (318).

Figure 16:
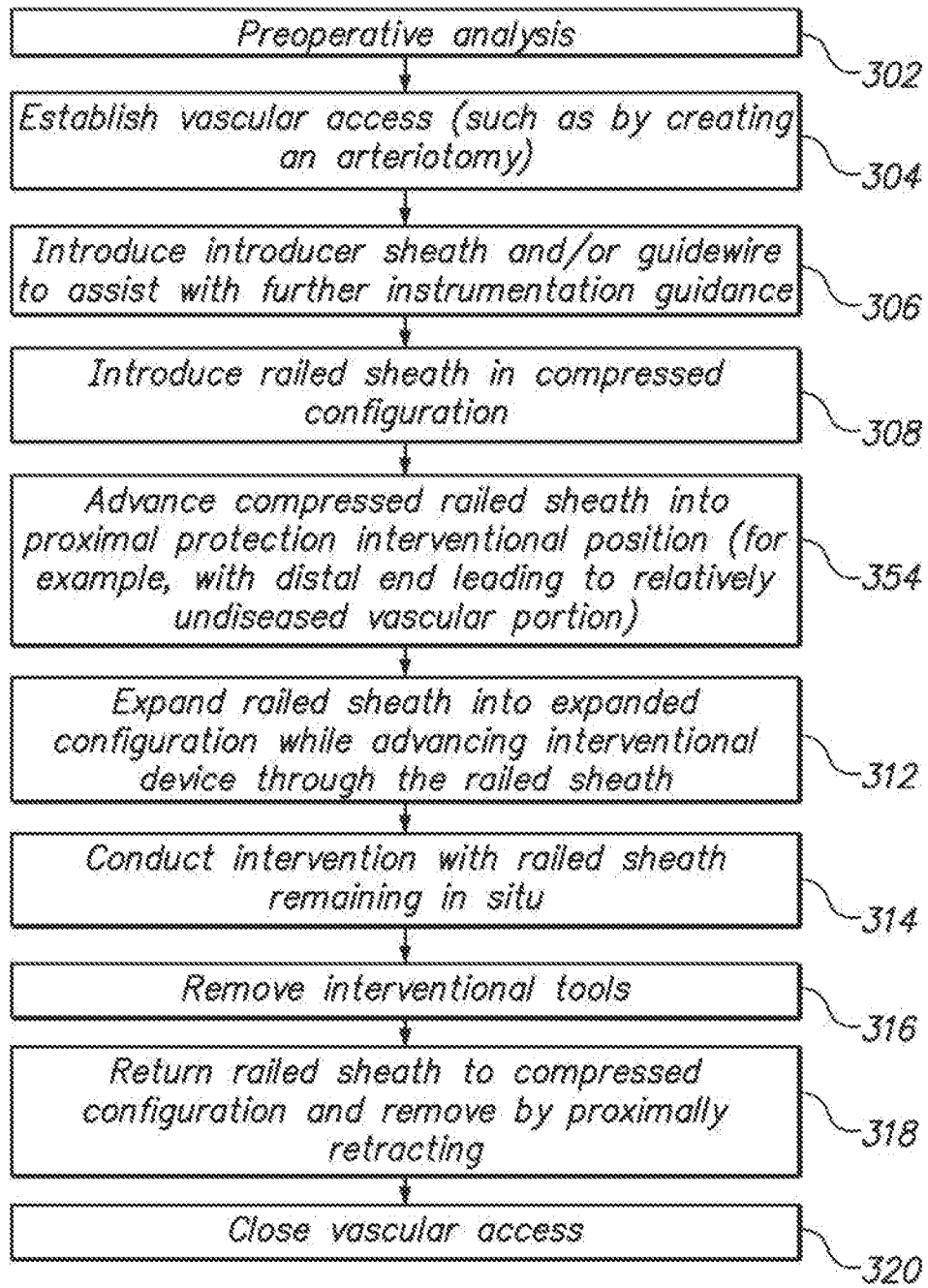
FIG. 16 illustrates various aspects of a deployment technique in accordance with the present invention.

Referring to FIG. 16, an embodiment similar to that of FIG. 10 is illustrated, with the exception that the railed sheath may be only partially positioned across the length of the vascular route to the targeted anatomy (i.e., rather than protecting the entire length with a railed sheath, only a portion, such as a proximal portion, may be protected) (354).

The rail structures may comprise various bio-compatible metals, such as titanium, alloys thereof such as Nitinol superalloy, and/or polymers such as polyethylene, ultra-high-molecular weight polyethylene, polyethylene terephthalate, polyoxymethylene, polytetrafluoroethylene, and co-polymers thereof.

The sheet-like member may comprise a material such as polyethylene, polytetrafluoroethylene, or co-polymers thereof.

In one embodiment, a vacuum device such as a syringe may be operatively coupled to the configuration (for example, coupled to or integrated into a proximal handle that forms a manual interface for inserting a railed sheath catheter), and may have an elongate distal portion that may be inserted into a deployed railed sheath catheter to vacuum away emboli that may be present.

Figure 18A:
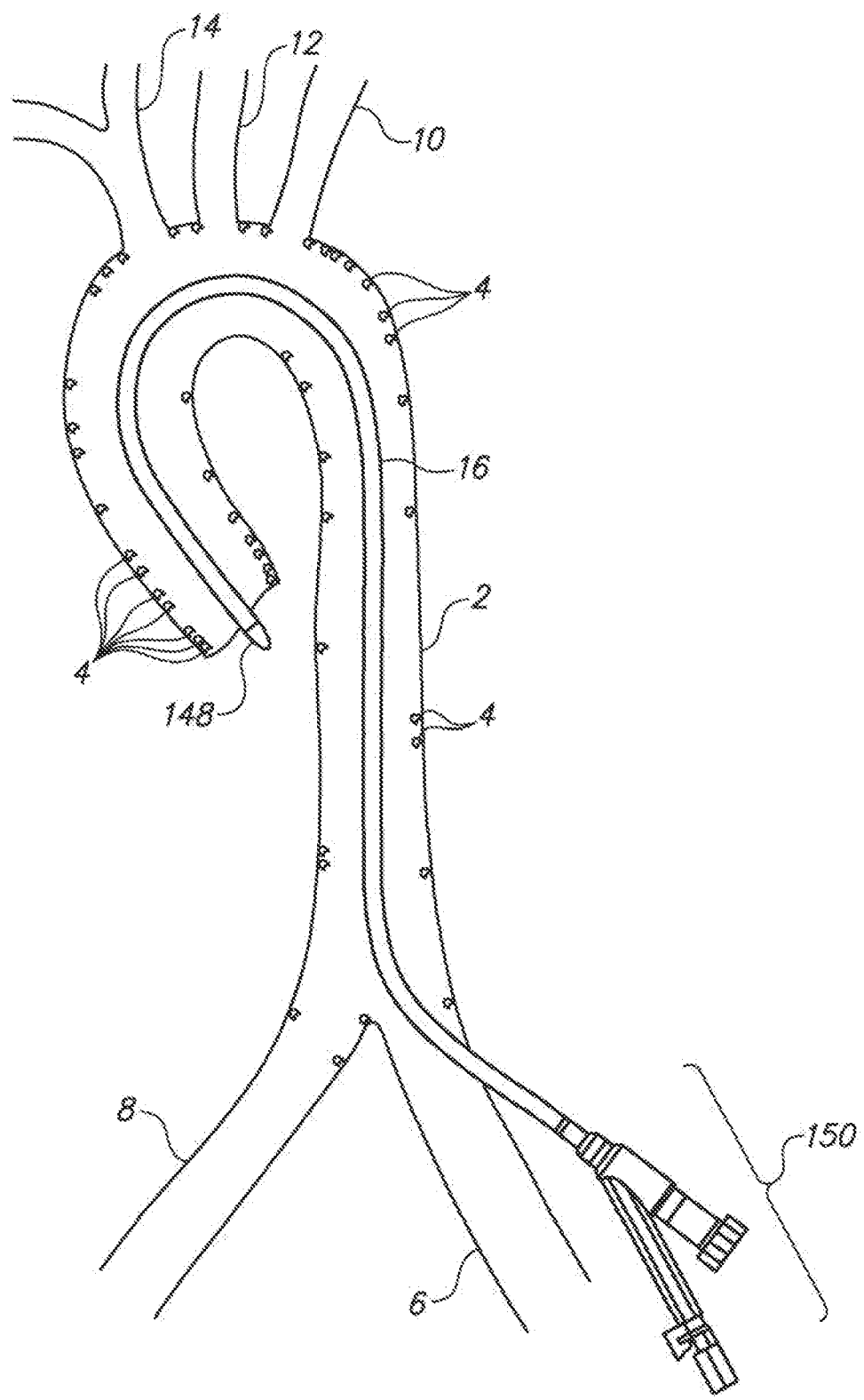
FIGS. 18A-18J illustrate various aspects of an inventive expandable railed sheath that may be used in conducting various cardiovascular procedures, such as a percutaneous aortic valve replacement procedure.
Figure 18B:
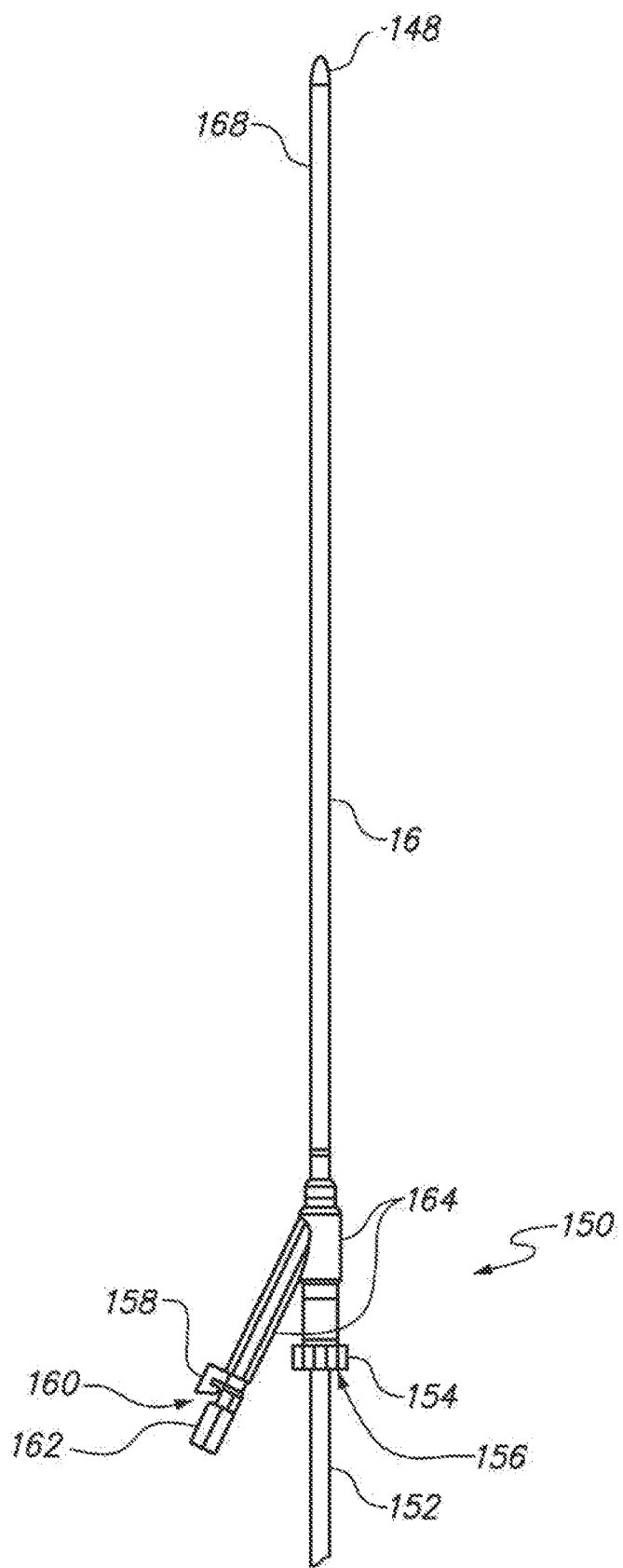
Figures 18C, 18D:
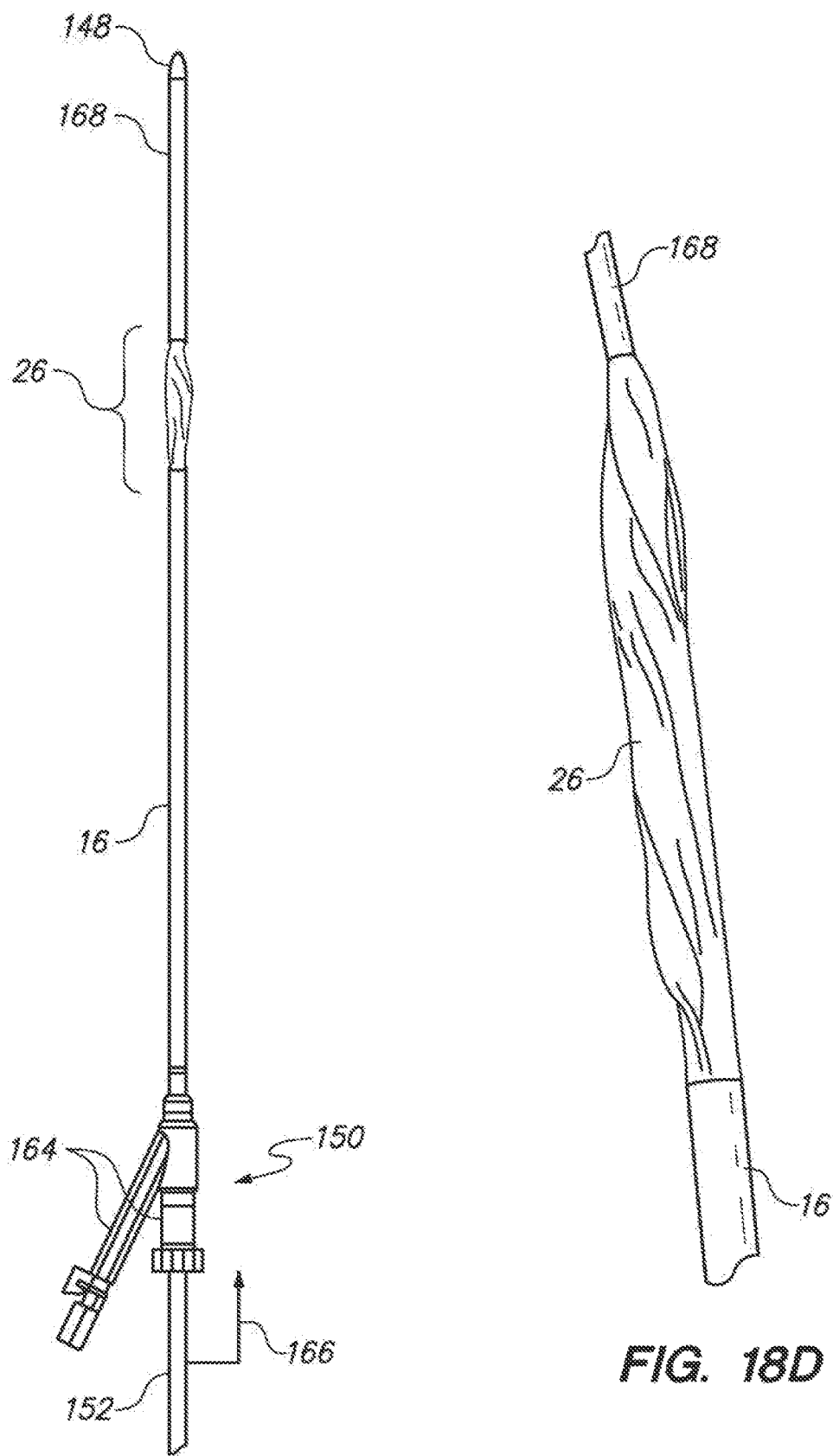
Figure 18E:
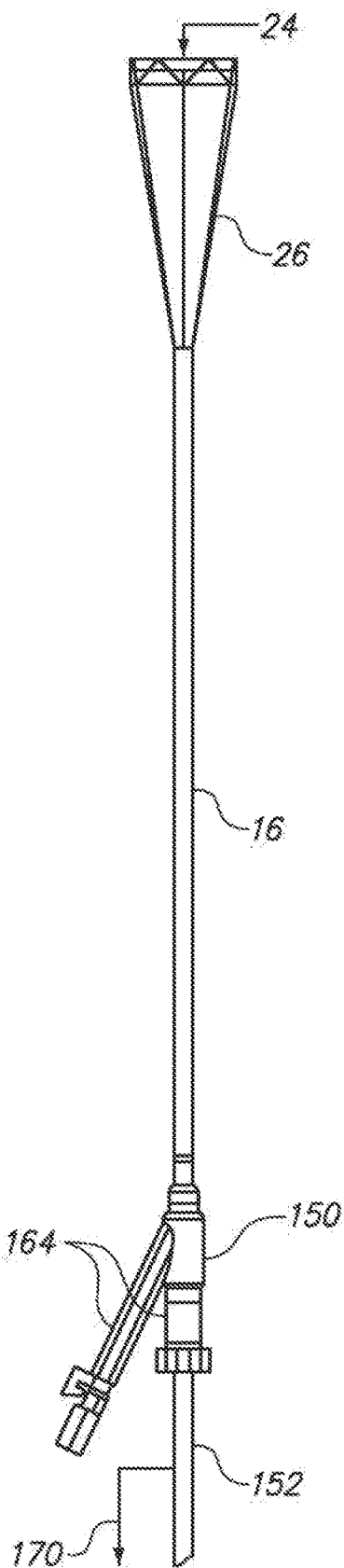

Referring to FIGS. 18A-18J, various aspects of another embodiment of an intervention protection configuration are shown, wherein a distal portion of the delivery configuration is allowed to expand relative to a more proximal portion which may remain substantially more contracted or collapsed. Referring to FIG. 18A, a railed sheath in a collapsed configuration (16) has been inserted through a diseased vessel such as aorta (2), starting with transvascular access through a portion of the associated vasculature such as the left iliac artery (6), followed by insertion of the instrument assembly into a position as shown wherein the distal tip is located in a preferred location, such as adjacent an aortic valve of the patient. A proximal portion of the instrumentation, including a proximal control assembly (150) remains external to the vascular access for manipulation and control of the procedure, along with optional external drainage or exit of fluids or emboli or other materials which may collect within the instrumentation. The depicted embodiment comprises an atraumatic obturator tip (148) selected to reduce the results of impacts that such distal instrumentation may have during insertion and placement. Referring to FIG. 18B, without the associated anatomy (i.e., from the illustration of FIG. 18A), the assembly may comprise a collapsed railed sheath portion (16) removably coupled to a distal obturator-jacket assembly (168) which has an atraumatic tip (148). The obturator-jacket assembly (168) preferably is coupled, through the lumen of the sheath and proximally out through a valved (154) port (156) defined through the tubular body assembly (164) of the proximal assembly (150), to an elongate obturator coupling member (152) which may be movably positioned through a central working lumen of the sheath (such as that referred to as element 24 above). The depicted proximal assembly (150) also comprises a second valved (158) port (160) which may be occupied by a portion of a sheath tip manipulation assembly, which may comprise a proximal manipulation structure or handle (162) which is coupled to a distal portion of the sheath using a movable tension-applying element such as a pullwire. In one embodiment, as described below, an operator may manually manipulate, or pull, the proximal manipulation structure (162) to tension the movable tension-applying element and cause closure of the distal tip of the sheath using a hoop configuration. The obturator-jacket assembly may be configured to assist in temporarily maintaining a collapsed configuration of a distal portion of the sheath, and may be configured to extend the full length of a particularly expandable portion of the sheath which may be expanded outward subsequent to removal of the obturator-jacket assembly (168) from its collapse restraint configuration as shown in FIG. 18B. For example, referring to FIG. 18C, with the sheath in a desired position relative to the associated anatomy, the obturator-jacket assembly (168) may be advanced or urged (166) distally relative to the remainder of the sheath assembly (16, 150), causing the obturator-jacket assembly (168), with its atraumatic distal tip (148), to become released from the remainder of the sheath assembly (16, 150) with such advancement. In one embodiment, such distal advancement causes a thin jacket-like wrapper portion of the obturator jacket assembly (168) to become torn or fractured along a predetermined pathway (i.e., via preexisting perforations created in the jacket-like wrapper portion) in a manner that substantially releases and decouples the underlying collapsed portions of the railed sheath assembly from the jacket-like wrapper portion (while the jacket-like wrapper portion remains firmly attached to the obturator tip 148), allowing a portion of the sheath to self-expand to an expanded configuration (26) as shown in FIG. 18C and the close-up view of FIG. 18D. Referring to FIG. 18E, with full distal advancement of the obturator assembly (168, 152), the distal portion of the railed sheath may be allowed to become fully expanded (26), and then the obturator assembly (168, 152) may be pulled proximally (170) through the lumen of the sheath (24) and through the proximal assembly (150) where it may be removed.

Figures 18F, 18G:
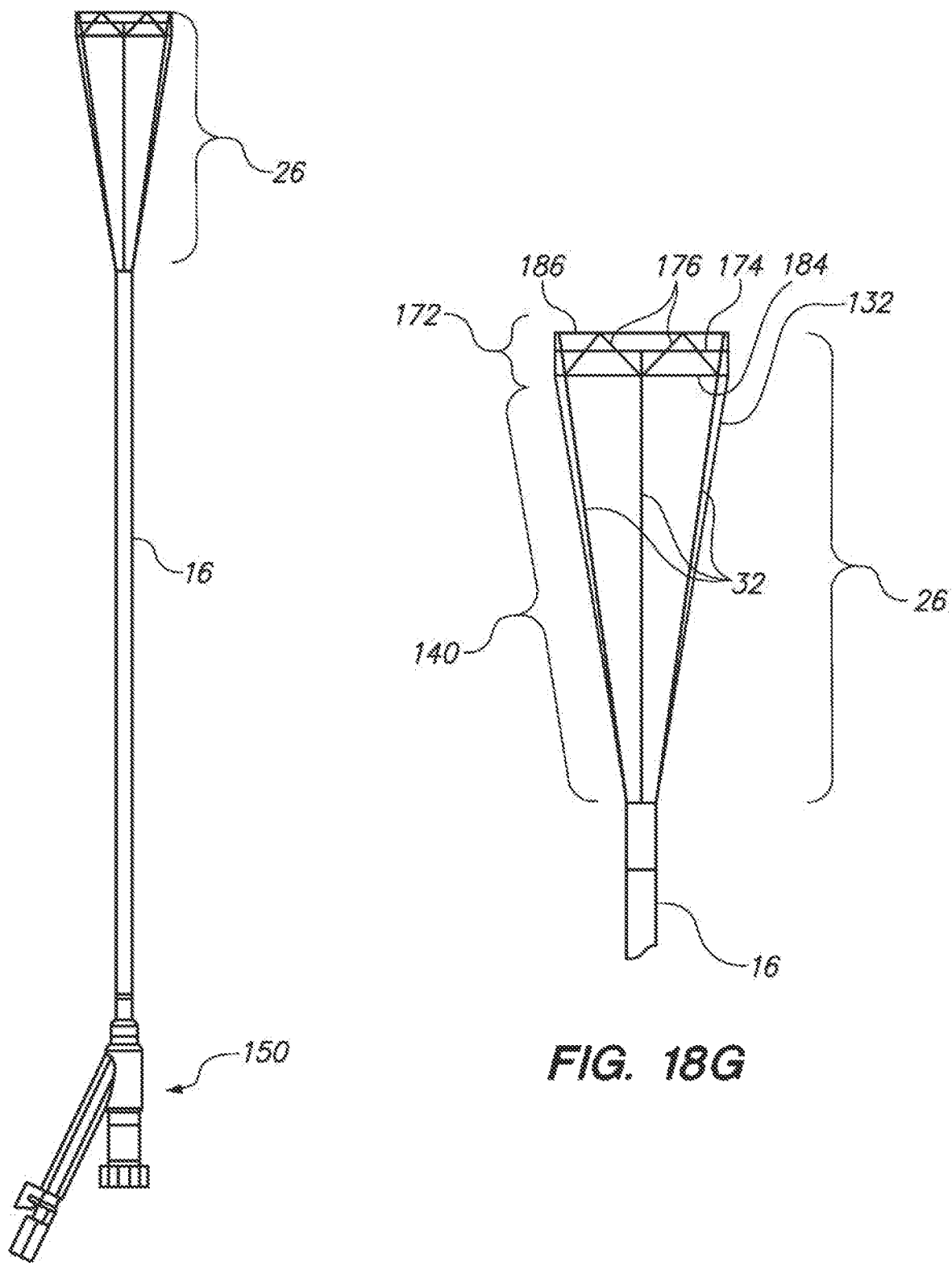
Figure 18H:
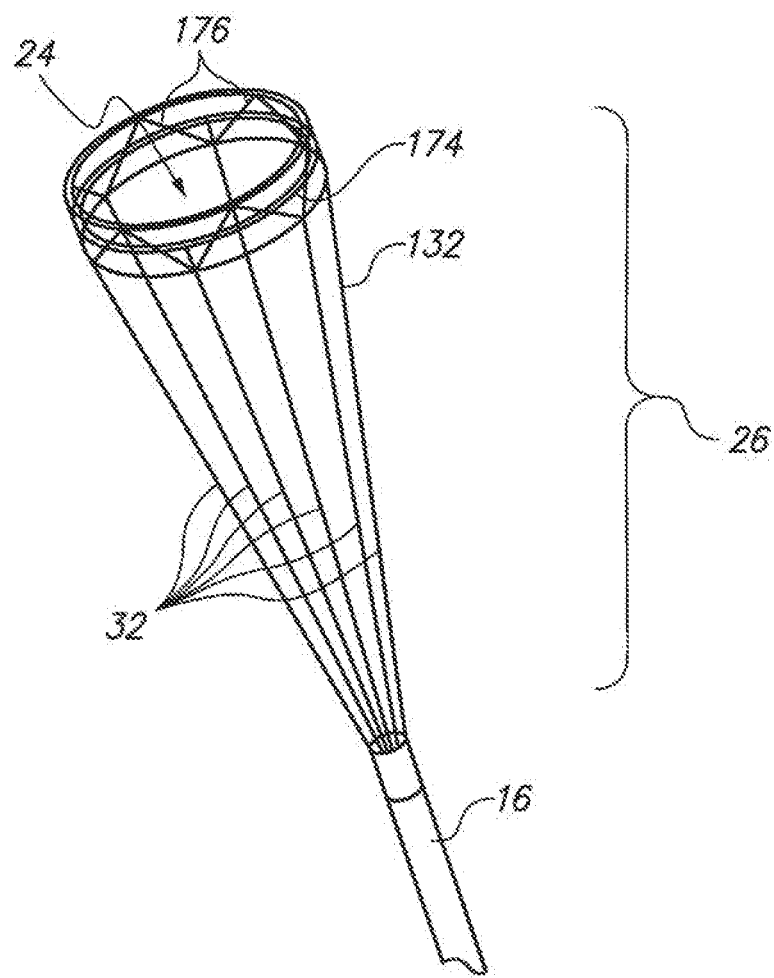
Figure 18I:
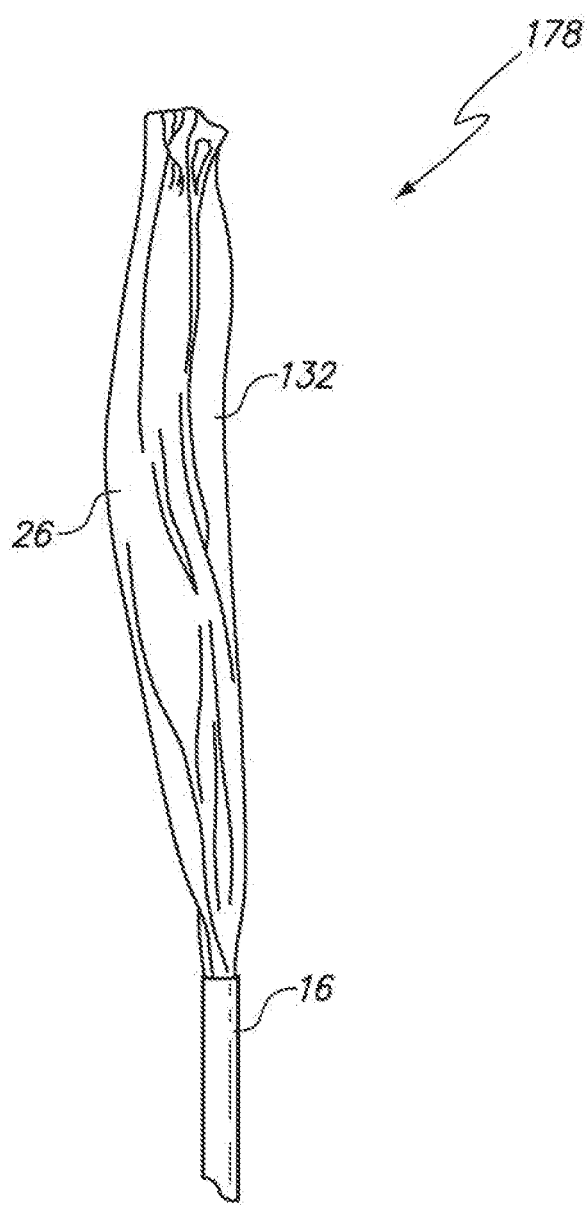
Figure 18J:
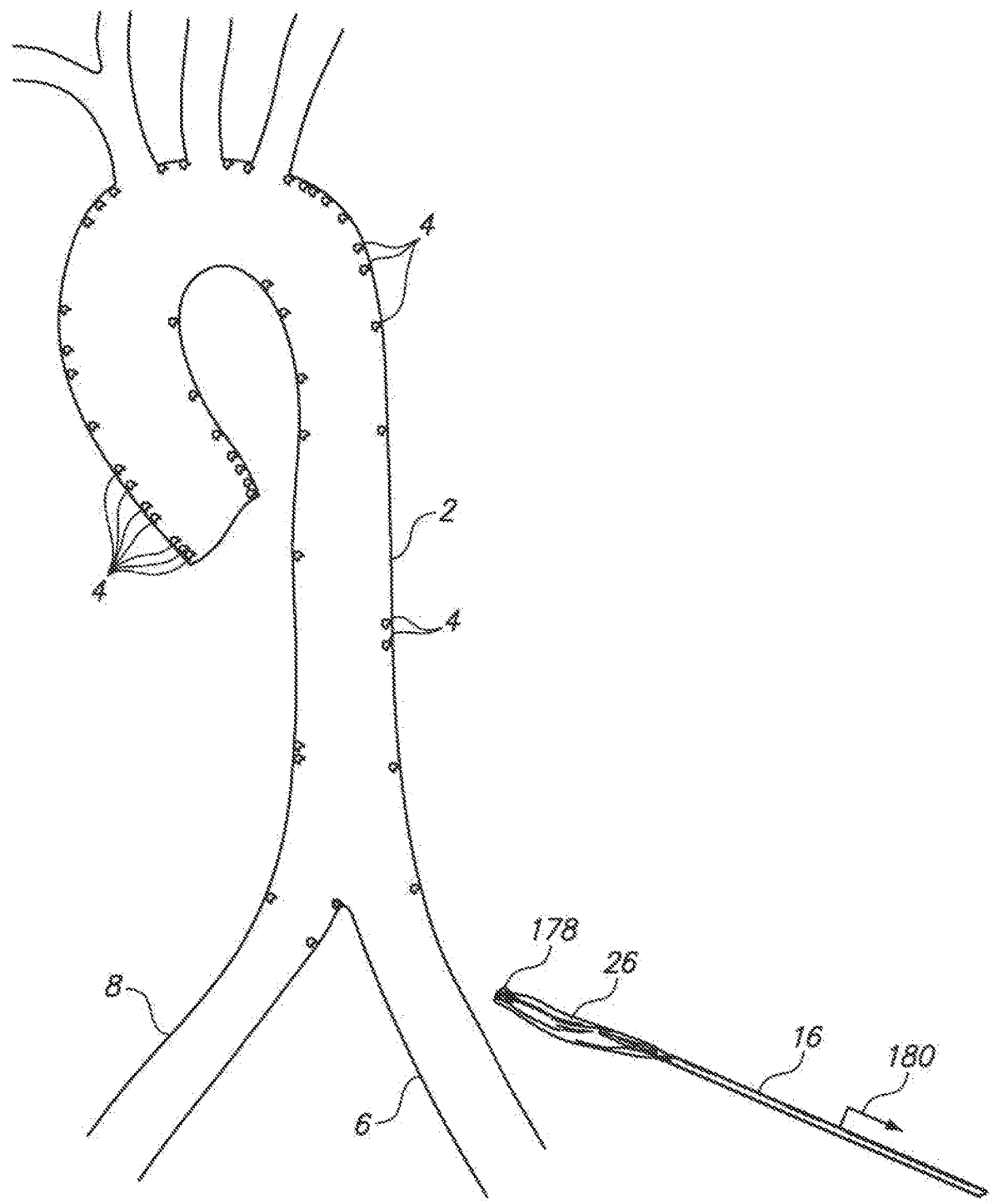

Referring to FIGS. 18F-18H, with the obturator assembly removed, this embodiment of the railed sheath is in an expanded configuration wherein a proximal portion of the railed sheath remains in a relatively collapsed or small diameter configuration (16) as compared with the expanded distal portion (26), which features a plurality of structural rail members (32) configured to self-expand and support a tubular or frustoconical porous filter mesh (132) surface configured to capture particles that may enter it, such as clots or plaque particles. In one embodiment wherein the sheath assembly is configured for aortic deployment, the expanded distal portion may be selected to have a length approximately equivalent to the arcuate length of the subject aortic arch. The embodiment depicted in close-up view in FIGS. 18G-18H features six elongate structural rail members (32) which may comprise a material such as a nickel titanium Nitinol superalloy; other embodiments may feature 4, 5, 7, 8, 9, 10, 11, 12, or more rail members (32), which may be configured to be prominent either to the inner surface or outer surface of the expanded portion (26), and may be configured to have various cross-sectional areas and/or positions, as in the embodiments described above in reference to FIGS. 3E-3Q. Referring to FIG. 18G, in one embodiment the most distal portion of the expanded sheath portion (26) may comprise a vessel engagement portion (172) selected to maximize physical accommodation of local endovascular geometry and/or terrain, so that particles moving through the pertinent vessel are biased to be captured by the railed sheath, not diverted around it. The depicted vessel engagement portion comprises a relatively low-modulus sheet-like material, which may comprise a thin biocompatible polymer, coupled in a cylindrical fashion to a relatively low-modulus zig-zag structure (176) intercoupled between two relatively low-modulus hoops (184, 186). These structures (176, 184, 186) may comprise relatively small-diameter Nitinol superalloy material, for example. A controllably collapsible hoop (174) may be intercoupled into the distal assembly and movably coupled to the proximal manipulation assembly (element 162 of FIG. 18B, for example) to allow an operator to pull upon the proximal manipulation assembly and cause increased hoop tension in the controllably collapsible hoop (174), causing such hoop to controllably collapse and close the distal assembly into a closed-distal configuration (178), as shown in FIG. 18I, after which the entire sheath assembly may be proximally (180) removed out of the subject anatomy while safely containing the contents of the sheath assembly which may have been captured during deployment, such as clots and/or plaque particles. In one embodiment, the entire expanded portion (26), such as illustrated in FIG. 18G, is a self-expanding structure, in that it is biased to expand to the expanded configuration (26) upon release of mechanical constraint such as the aforementioned obturator jacket. In another embodiment, only a tip portion is a self-expanding structure, such as a tip portion including the distal engagement portion (172) and a distal subportion of the frustoconical distal portion (140) of the sheath.

In another embodiment, the removable obturator jacket covering and restraining the underlying compressed distal portion of the sheath, such as in the assembly of FIG. 18B, may be removed directly from the outside using a tensile member coupled to the outer surface of the jacket and configured to tear the jacket away from the underlying compressed distal portion of the sheath to allow such compressed distal portion to self-expand. In other words, rather than inserting, then retracting the obturator member to detach and remove the jacket covering from the underlying compressed distal portion of the sheath by pulling the removed jacket out through the working lumen of the sheath, the jacket covering may be pulled off from the outside using a tensile member, such as a pullwire configured to be manually and controllably tensioned from a proximal location using a handle or other tensioning fixture, coupled between the jacket and a proximal location accessible using the proximal assembly (150) and pulled proximally away from the sheath in a tear-away fashion prescribed by predetermined patterning (i.e., through perforated tear-away lines or patterns). In another embodiment, a combination of release/removal from through the working lumen, and release/removal from the outside aspect of the sheath as described immediately above, may be utilized to fully release the sheath distal end and allow self-expansion.

In summary, as described above, the inventive protective configurations provide a means for conducting an intervention while also protecting the underlying tissue and related anatomy; further, the railed sheath configurations assist with delivery and alignment of tools and/or prostheses which may be related to the vascular intervention.

Figure 19:
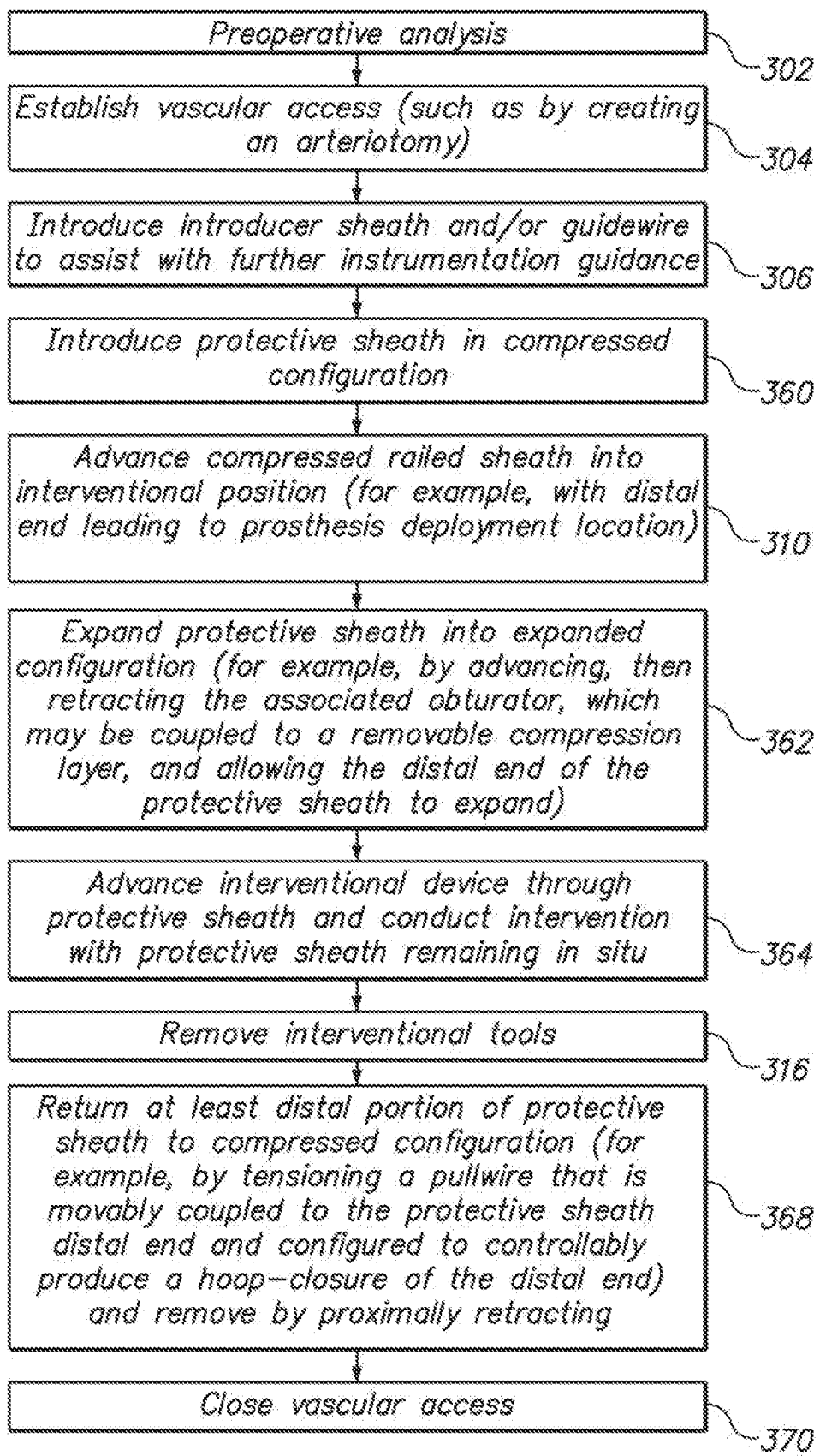
FIG. 19 illustrates various aspects of a deployment technique in accordance with the present invention.

Referring to the process flow embodiment of FIG. 19, for example, after preoperative analysis (302), vascular access may be established (304) and a guidewire and/or introducer may be advanced into the subject vessel lumen (306). A protective or railed sheath may be introduced (360) and advanced (310) in a compressed configuration to place the distal portion in a desired position relative to the subject anatomy (for example, in an aortic valve prosthesis deployment configuration, the sheath may be positioned to allow for deployment of the valve prosthesis adjacent the aortic outflow tract of the patient, as planned preoperatively). The protective or railed sheath may be converted to its expanded configuration, which may comprise advancement and then retraction of an obturator assembly, as described above in reference to FIGS. 18A-18J, which may remove a wrapper layer or compression layer coupled to the obturator, thereby allowing the underlying sheath portion to self-expand in a manner akin to that of a self-expanding stent prosthesis (362). With the protective or railed sheath in the expanded/deployed configuration, intervention steps may be conducted which involve insertion and/or retraction of one or more devices, tools, or prostheses through the working lumen defined through the sheath, with protection provided to associated tissues by virtue of such sheath deployment (364). Subsequently the tools may be removed (316), and the expanded distal portion of the sheath controllably returned to a safe removal configuration wherein at least a distal portion of the sheath is controllably collapsed or closed, such as by a hoop closure actuated by proximally pulling a tension or pullwire, as described above in reference to FIGS. 18A-18J (368). Vascular access may then be closed after removal of the sheath assembly (320).

Various exemplary embodiments of the invention are described herein. Reference is made to these examples in a non-limiting sense. They are provided to illustrate more broadly applicable aspects of the invention. Various changes may be made to the invention described and equivalents may be substituted without departing from the true spirit and scope of the invention. In addition, many modifications may be made to adapt a particular situation, material, composition of matter, process, process act(s) or step(s) to the objective(s), spirit or scope of the present invention. Further, as will be appreciated by those with skill in the art that each of the individual variations described and illustrated herein has discrete components and features which may be readily separated from or combined with the features of any of the other several embodiments without departing from the scope or spirit of the present inventions. All such modifications are intended to be within the scope of claims associated with this disclosure.

Any of the devices described for carrying out the subject diagnostic or interventional procedures may be provided in packaged combination for use in executing such interventions. These supply "kits" may further include instructions for use and be packaged in sterile trays or containers as commonly employed for such purposes.

The invention includes methods that may be performed using the subject devices. The methods may comprise the act of providing such a suitable device. Such provision may be performed by the end user. In other words, the "providing" act merely requires the end user obtain, access, approach, position, set-up, activate, power-up or otherwise act to provide the requisite device in the subject method. Methods recited herein may be carried out in any order of the recited events which is logically possible, as well as in the recited order of events.

Exemplary aspects of the invention, together with details regarding material selection and manufacture have been set forth above. As for other details of the present invention, these may be appreciated in connection with the above-referenced patents and publications as well as generally known or appreciated by those with skill in the art. For example, one with skill in the art will appreciate that one or more lubricious coatings (e.g., hydrophilic polymers such as polyvinylpyrrolidone-based compositions, fluoropolymers such as tetrafluoroethylene, hydrophilic gel or silicones) may be used in connection with various portions of the devices, such as relatively large interfacial surfaces of movably coupled parts, if desired, for example, to facilitate low friction manipulation or advancement of such objects relative to other portions of the instrumentation or nearby tissue structures. The same may hold true with respect to method-based aspects of the invention in terms of additional acts as commonly or logically employed.

In addition, though the invention has been described in reference to several examples optionally incorporating various features, the invention is not to be limited to that which is described or indicated as contemplated with respect to each variation of the invention. Various changes may be made to the invention described and equivalents (whether recited herein or not included for the sake of some brevity) may be substituted without departing from the true spirit and scope of the invention. In addition, where a range of values is provided, it is understood that every intervening value, between the upper and lower limit of that range and any other stated or intervening value in that stated range, is encompassed within the invention.

Also, it is contemplated that any optional feature of the inventive variations described may be set forth and claimed independently, or in combination with any one or more of the features described herein. Reference to a singular item, includes the possibility that there are plural of the same items present. More specifically, as used herein and in claims associated hereto, the singular forms "a," "an," "said," and "the" include plural referents unless specifically stated otherwise. In other words, use of the articles allow for "at least one" of the subject item in the description above as well as claims associated with this disclosure. It is further noted that such claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in claims associated with this disclosure shall allow for the inclusion of any additional element—irrespective of whether a given number of elements are enumerated in such claims, or the addition of a feature could be regarded as transforming the nature of an element set forth in such claims. Except as specifically defined herein, all technical and scientific terms used herein are to be given as broad a commonly understood meaning as possible while maintaining claim validity.

The breadth of the present invention is not to be limited to the examples provided and/or the subject specification, but rather only by the scope of claim language associated with this disclosure.

The invention claimed is:

1. A method for deploying a device to a distal location across a diseased vessel, comprising:
   inserting an expandable protective sheath system into a diseased vessel, wherein the expandable protective sheath system comprises an obturator assembly removably coupled to a distal portion of a sheath, wherein the sheath comprises a lumen, the lumen having a first lumen inner diameter when the sheath is in a collapsed configuration, and wherein the lumen has a second lumen inner diameter when the sheath is in an expanded configuration;
   advancing the sheath in the collapsed configuration through the diseased vessel to a desired location;
   distally advancing the obturator assembly through the lumen and releasing the obturator assembly from the sheath;
   allowing the distal portion of the sheath to expand, wherein the distal portion of the sheath comprises a tubular porous filter mesh coupled to a collapsible hoop structure;
   expanding the collapsible hoop structure to fully expand the tubular porous filter mesh to engage a wall of the diseased vessel;
   removing the obturator assembly by pulling the obturator assembly proximally through the lumen;
   capturing particles in the blood with the tubular porous filter mesh; and
   advancing and deploying a device through the sheath.

2. The method of claim 1, wherein the obturator assembly has an atraumatic distal tip.

3. The method of claim 1, wherein advancing the sheath through the diseased vessel comprises advancing the sheath through an aorta.

4. The method of claim 1, wherein advancing and deploying the device comprises implanting a prosthesis.

5. The method of claim 4, wherein the prosthesis is a cardiac valve.

6. The method of claim 1, wherein the expandable protective sheath system comprises a proximal manipulation structure coupled to a tension member coupled to the collapsible hoop structure, and wherein actuation of the proximal manipulation structure collapses the collapsible hoop structure.

7. The method of claim 6, wherein the tension member comprises a tension wire, which collapses the collapsible hoop structure upon pulling the tension wire.

8. The method of claim 1, wherein advancing and deploying the device comprises withdrawing the obturator assembly from the sheath prior to deployment of the device.

9. The method of claim 1, wherein removing the obturator assembly from the sheath comprises moving the obturator assembly proximally after moving the obturator assembly distally to remove a constraint from the distal portion of the sheath.

10. The method of claim 1, wherein the method further comprises collapsing the collapsible hoop structure and capturing particles with the tubular porous filter mesh.

11. The method of claim 1, further comprising withdrawing the sheath from the diseased vessel.

* * * * *